US012612367B2

(12) United States Patent
Ootsuki et al.

(10) Patent No.: US 12,612,367 B2
(45) Date of Patent: Apr. 28, 2026

(54) METHOD FOR PRODUCING NITROGEN-CONTAINING HETEROARYLCARBOXAMIDE ACETIC ACID DERIVATIVE

(71) Applicant: Akebia Therapeutics, Inc., Cambridge, MA (US)

(72) Inventors: Kazufumi Ootsuki, Osaka (JP); Muneki Kishida, Osaka (JP); Atsushi Moroda, Osaka (JP); Kohki Fukuhara, Osaka (JP); Hirotoshi Yagishita, Osaka (JP)

(73) Assignee: Akebia Therapeutics, Inc., Cambridge, MA (US)

( * ) Notice: Subject to any disclaimer, the term of this patent is extended or adjusted under 35 U.S.C. 154(b) by 930 days.

(21) Appl. No.: 17/783,816

(22) PCT Filed: Dec. 9, 2020

(86) PCT No.: PCT/JP2020/045871
§ 371 (c)(1),
(2) Date: Dec. 23, 2022

(87) PCT Pub. No.: WO2021/117767
PCT Pub. Date: Jun. 17, 2021

(65) Prior Publication Data

US 2023/0159462 A1 May 25, 2023

(30) Foreign Application Priority Data

Dec. 10, 2019 (JP) ................................ 2019-222845

(51) Int. Cl.
*C07D 213/81* (2006.01)
*C07D 213/65* (2006.01)

(52) U.S. Cl.
CPC ......... *C07D 213/81* (2013.01); *C07D 213/65* (2013.01); *C07B 2200/13* (2013.01)

(58) Field of Classification Search
CPC .. C07D 213/65; C07D 213/81; C07B 2200/13
See application file for complete search history.

(56) References Cited

U.S. PATENT DOCUMENTS 3,655,679 A 4/1972 Tsung-ying et al.
3,703,582 A 11/1972 Shen et al.
3,894,920 A 7/1975 Kondo et al.
4,016,287 A 4/1977 Eberhardt et al.
(Continued)

FOREIGN PATENT DOCUMENTS

CA 2098158 A1 6/1993
CA 2253282 A1 11/1997
(Continued)

OTHER PUBLICATIONS

U.S. Appl. No. 17/053,614, filed Nov. 6, 2020, Gorin et al.
"Hippuric acid sodium salt", Science Lab.com: Chemicals & Laboratory Equipment; retrieved from the internet at <http://web.archive.org/web/20041107121553/http://www.sciencelab.com/page/S/PVAR/10415/SLH2620> on Mar. 11, 2010. 1 page.
"Standards of Medical Care in Diabetes—2006", Diabetes Care, 29: s4-s42 (2006).
"Akebia closes $41 million series C—Proceeds to support phase 2b trial and phase 3 preparations for promising anemia candidate", 2013; retrieved from the internet at <http://files.shareholder.com/downloads/AMDA-2MD7AT/0x0x733748/5e5822e6-2bcd-4969-ab79-0d298fee5066/733748.pdf> on Jan. 22, 2018. 2 pages.
Acker et al., "Genetic evidence for a tumor suppressor role of HIF-2α", Cancer Cell, 8:131-141 (2005).
(Continued)

*Primary Examiner* — D Margaret M Seaman
(74) *Attorney, Agent, or Firm* — Proskauer Rose LLP

(57) ABSTRACT

The present invention provides a novel process for preparing the compound I containing the compound [I(A)] (vadadustat) and the compound [I(B)] (roxadustat) which are useful as a medicine in an industrially advantageous manner, and a process for preparing the compound I which comprises reacting the compound (a1) or the compound (b1), the compound (2) or salts of the compound (2), with carbon monoxide in the presence of a palladium catalyst, in the presence or absence of a ligand, in the presence of a base, in a solvent to prepare the compound I (wherein structure formulae of the compound (a1), the compound (b1) or the compound (2), and the definitions of groups in the formulae are defined in the description.

I

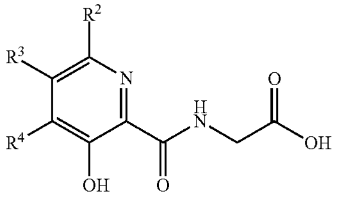

I(A)

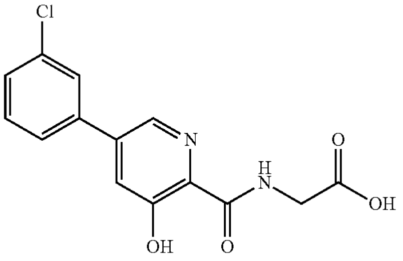

I(B)

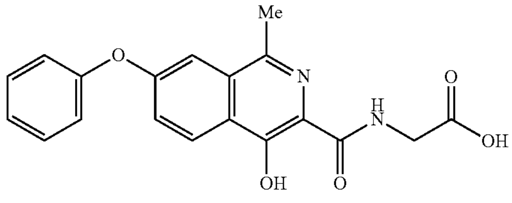

24 Claims, 3 Drawing Sheets

(56) References Cited

U.S. PATENT DOCUMENTS

| | | | |
|---|---|---|---|
| 5,397,799 | A | 3/1995 | Kress et al. |
| 5,405,613 | A | 4/1995 | Rowland et al. |
| 5,607,954 | A | 3/1997 | Weidmann et al. |
| 5,610,172 | A | 3/1997 | Weidmann et al. |
| 5,620,995 | A | 4/1997 | Weidemann et al. |
| 5,620,996 | A | 4/1997 | Weidmann et al. |
| 5,658,933 | A | 8/1997 | Weidemann et al. |
| 5,719,164 | A | 2/1998 | Weidmann et al. |
| 5,726,305 | A | 3/1998 | Weidmann et al. |
| 6,020,350 | A | 2/2000 | Wiedmann et al. |
| 6,093,730 | A | 7/2000 | Weidmann et al. |
| 6,159,379 | A | 12/2000 | Means et al. |
| 6,420,427 | B1 | 7/2002 | Takahashi et al. |
| 6,566,088 | B1 | 5/2003 | McKnight et al. |
| 6,589,758 | B1 | 7/2003 | Zhu |
| 7,183,287 | B2 | 2/2007 | Durley |
| 7,323,475 | B2 | 1/2008 | Arend et al. |
| 7,588,924 | B2 | 9/2009 | Evdokimov et al. |
| 7,811,595 | B2 * | 10/2010 | Kawamoto ............. A61P 17/02 514/346 |
| 8,050,873 | B2 | 11/2011 | Evdokimov et al. |
| 8,124,582 | B2 | 2/2012 | Guenzler-Pukall et al. |
| 8,129,376 | B2 | 3/2012 | Sundaresan et al. |
| 8,273,773 | B2 | 9/2012 | Brameld et al. |
| 8,323,671 | B2 | 12/2012 | Wu et al. |
| 8,343,952 | B2 | 1/2013 | Kawamoto et al. |
| 8,512,972 | B2 | 8/2013 | Evdokimov et al. |
| 8,530,404 | B2 | 9/2013 | Seeley et al. |
| 8,598,210 | B2 | 12/2013 | Kawamoto et al. |
| 8,722,895 | B2 | 5/2014 | Kawamoto et al. |
| 8,865,748 | B2 | 10/2014 | Shalwitz et al. |
| 8,940,773 | B2 | 1/2015 | Kawamoto et al. |
| 9,145,366 | B2 | 9/2015 | Lanthier et al. |
| 9,598,370 | B2 * | 3/2017 | Kawamoto ........... C07C 255/57 |
| 9,701,636 | B2 | 7/2017 | Copp et al. |
| 9,776,969 | B2 | 10/2017 | Lanthier et al. |
| 9,987,262 | B2 | 6/2018 | Copp et al. |
| 10,149,842 | B2 | 12/2018 | Copp et al. |
| 10,246,416 | B2 | 4/2019 | Lanthier et al. |
| RE47,437 | E | 6/2019 | Kawamoto et al. |
| 10,596,158 | B2 | 3/2020 | Copp et al. |
| 10,729,681 | B2 | 8/2020 | Kawamoto et al. |
| 10,738,010 | B2 | 8/2020 | Lanthier et al. |
| 11,267,785 | B2 | 3/2022 | Lanthier et al. |
| 11,426,393 | B2 * | 8/2022 | Kawamoto ........ C07D 295/192 |
| 11,883,386 | B2 * | 1/2024 | Kawamoto ............. A61P 31/04 |
| 2002/0192737 | A1 | 12/2002 | Kaelin, Jr. et al. |
| 2003/0153503 | A1 | 8/2003 | Klaus et al. |
| 2003/0176317 | A1 | 9/2003 | Guenzler-Pukall et al. |
| 2004/0235082 | A1 | 11/2004 | Foumey et al. |
| 2004/0254215 | A1 | 12/2004 | Arend et al. |
| 2006/0142389 | A1 | 6/2006 | Aurell et al. |
| 2006/0276477 | A1 | 12/2006 | Klaus et al. |
| 2007/0105899 | A1 | 5/2007 | Suzuki et al. |
| 2007/0154482 | A1 | 7/2007 | Sukhatme et al. |
| 2007/0203174 | A1 | 8/2007 | Klimko et al. |
| 2007/0213335 | A1 | 9/2007 | Fitch et al. |
| 2007/0299086 | A1 | 12/2007 | Kawamoto et al. |
| 2008/0124740 | A1 | 5/2008 | Evkokimov et al. |
| 2008/0213404 | A1 | 9/2008 | Johnson et al. |
| 2009/0023666 | A1 | 1/2009 | Gardiner et al. |
| 2009/0082357 | A1 | 3/2009 | Fitch et al. |
| 2009/0240475 | A1 | 9/2009 | Evdokimov et al. |
| 2010/0021423 | A1 | 1/2010 | Brameld et al. |
| 2010/0331303 | A1 | 12/2010 | Kawamoto et al. |
| 2010/0331374 | A1 | 12/2010 | Wu et al. |
| 2011/0077400 | A1 | 3/2011 | Lobben et al. |
| 2011/0305776 | A1 | 12/2011 | Ho et al. |
| 2012/0282627 | A1 | 11/2012 | Evdokimov et al. |
| 2012/0309977 | A1 | 12/2012 | Lanthier et al. |
| 2012/0316204 | A1 | 12/2012 | Shalwitz et al. |
| 2012/0329836 | A1 | 12/2012 | Marsh et al. |
| 2013/0022974 | A1 | 1/2013 | Chinnaiyan et al. |
| 2013/0203816 | A1 | 8/2013 | Kawamoto et al. |
| 2013/0245076 | A1 | 9/2013 | Kawamoto et al. |
| 2014/0045899 | A1 | 2/2014 | Kawamoto et al. |
| 2014/0057892 | A1 | 2/2014 | Kawamoto et al. |
| 2015/0119425 | A1 | 4/2015 | Kawamoto et al. |
| 2015/0141467 | A1 | 5/2015 | Copp |
| 2015/0361043 | A1 | 12/2015 | Lanthier et al. |
| 2016/0009648 | A1 | 1/2016 | Kawamoto et al. |
| 2016/0143891 | A1 | 5/2016 | Shalwitz et al. |
| 2016/0199434 | A1 | 7/2016 | Eubank et al. |
| 2016/0214939 | A1 | 7/2016 | Hanselmann et al. |
| 2016/0339005 | A1 | 11/2016 | Shalwitz et al. |
| 2017/0189387 | A1 | 7/2017 | Kawamoto et al. |
| 2017/0258773 | A1 | 9/2017 | Copp et al. |
| 2017/0362178 | A1 | 12/2017 | Lanthier et al. |
| 2018/0065933 | A1 | 3/2018 | Hanselmann et al. |
| 2018/0092892 | A1 | 4/2018 | Smith et al. |
| 2018/0280365 | A1 | 10/2018 | Copp et al. |
| 2019/0192494 | A1 | 6/2019 | Kawamoto et al. |
| 2020/0345711 | A1 | 11/2020 | Copp et al. |
| 2021/0122715 | A1 | 4/2021 | Lanthier et al. |
| 2021/0137091 | A1 | 5/2021 | Dolshun et al. |
| 2021/0206721 | A1 | 7/2021 | Ranjan et al. |

FOREIGN PATENT DOCUMENTS

| | | | |
|---|---|---|---|
| CA | 2755132 | A1 | 10/2010 |
| CN | 105837502 | A | 8/2016 |
| CN | 111320577 | A | 6/2020 |
| EP | 0650960 | A1 | 5/1995 |
| EP | 0650961 | A1 | 5/1995 |
| EP | 2044005 | B1 | 10/2010 |
| EP | 2718265 | B1 | 12/2015 |
| EP | 3000808 | B1 | 9/2017 |
| EP | 3290404 | B1 | 12/2019 |
| JP | H09221476 | A | 8/1997 |
| JP | 2001-48786 | A | 2/2001 |
| JP | 2007-194072 | A | 8/2007 |
| JP | 2010-527378 | A | 8/2010 |
| JP | A-2014-522409 | A | 9/2014 |
| JP | A-2018-111697 | A | 7/2018 |
| RU | 2145959 | C1 | 2/2000 |
| WO | WO-1996/022021 | A1 | 7/1996 |
| WO | WO-1997/041103 | A1 | 11/1997 |
| WO | WO-1997/044333 | A1 | 11/1997 |
| WO | WO-1999/048870 | A1 | 11/1999 |
| WO | WO-2002/074980 | A2 | 9/2002 |
| WO | WO-2002/074981 | A2 | 9/2002 |
| WO | WO-2002/083688 | A1 | 10/2002 |
| WO | WO-2003/028663 | A2 | 4/2003 |
| WO | WO-2003/032972 | A1 | 4/2003 |
| WO | WO-2003/049686 | A2 | 6/2003 |
| WO | WO-2003/053997 | A2 | 7/2003 |
| WO | WO-2003/097040 | A1 | 11/2003 |
| WO | WO-2004/019868 | A2 | 3/2004 |
| WO | WO-2004/035812 | A2 | 4/2004 |
| WO | WO-2004/048383 | A1 | 6/2004 |
| WO | WO-2004/108121 | A1 | 12/2004 |
| WO | WO-2005/007192 | A2 | 1/2005 |
| WO | WO-2005/115984 | A2 | 12/2005 |
| WO | WO-2005/118836 | A2 | 12/2005 |
| WO | WO-2006/019831 | A1 | 2/2006 |
| WO | WO-2006/030977 | A2 | 3/2006 |
| WO | WO-2006/114213 | A1 | 11/2006 |
| WO | WO-2006/138511 | A2 | 12/2006 |
| WO | WO-2007/038571 | A2 | 4/2007 |
| WO | WO-2007/047194 | A2 | 4/2007 |
| WO | WO-2007/070359 | A2 | 6/2007 |
| WO | WO-2007/082899 | A1 | 7/2007 |
| WO | WO-2007/084667 | A2 | 7/2007 |
| WO | WO-2007/088571 | A2 | 8/2007 |
| WO | WO-2007/103905 | A2 | 9/2007 |
| WO | WO-2007/136990 | A2 | 11/2007 |
| WO | WO-2007/150011 | A2 | 12/2007 |
| WO | WO-2008/002576 | A2 | 1/2008 |
| WO | WO-2008/089051 | A1 | 7/2008 |
| WO | WO-2008/089052 | A2 | 7/2008 |
| WO | WO-2009/020119 | A1 | 8/2008 |
| WO | WO-2008/130508 | A1 | 10/2008 |
| WO | WO-2008/130527 | A1 | 10/2008 |
| WO | WO-2008/137060 | A1 | 11/2008 |

(56) References Cited

FOREIGN PATENT DOCUMENTS

| | | | |
|---|---|---|---|
| WO | WO-2008/141731 | A2 | 11/2008 |
| WO | WO-2008/144266 | A1 | 11/2008 |
| WO | WO-2009/019656 | A1 | 2/2009 |
| WO | WO-2009/035534 | A2 | 3/2009 |
| WO | WO-2009/037570 | A2 | 3/2009 |
| WO | WO-2009/039321 | A1 | 3/2009 |
| WO | WO-2009/039323 | A1 | 3/2009 |
| WO | WO-2009/043093 | A1 | 4/2009 |
| WO | WO-2009/049112 | A1 | 4/2009 |
| WO | WO-2009/067790 | A1 | 6/2009 |
| WO | WO-2009/070644 | A1 | 6/2009 |
| WO | WO-2009/073497 | A2 | 6/2009 |
| WO | WO-2009/073669 | A1 | 6/2009 |
| WO | WO-2009/086044 | A1 | 7/2009 |
| WO | WO-2009/086592 | A1 | 7/2009 |
| WO | WO-2009/089547 | A1 | 7/2009 |
| WO | WO-2009/111337 | A1 | 9/2009 |
| WO | WO-2010/029577 | A2 | 3/2010 |
| WO | WO-2010/113942 | A1 | 10/2010 |
| WO | WO-2011/057112 | A1 | 11/2010 |
| WO | WO-2012/170377 | A1 | 12/2012 |
| WO | WO-2012/170439 | A1 | 12/2012 |
| WO | WO-2012/170442 | A1 | 12/2012 |
| WO | WO-2013/013609 | A1 | 1/2013 |
| WO | WO-2014/014834 | A1 | 1/2014 |
| WO | WO-2014/168986 | A1 | 10/2014 |
| WO | WO-2014/200773 | A2 | 12/2014 |
| WO | WO-2015/023967 | A2 | 2/2015 |
| WO | WO-2015/073779 | A1 | 5/2015 |
| WO | WO-2015/112831 | A1 | 7/2015 |
| WO | WO-2016/118858 | A1 | 7/2016 |
| WO | WO-2016/153996 | A1 | 9/2016 |
| WO | WO-2016/161094 | A1 | 10/2016 |
| WO | WO-2019/217550 | A1 | 11/2019 |
| WO | WO-2020/217733 | A1 | 10/2020 |
| WO | WO-2021/087144 | A1 | 5/2021 |
| WO | WO-2021/188936 | A1 | 9/2021 |
| WO | WO-2021/188938 | A1 | 9/2021 |
| WO | WO-2021/188944 | A1 | 9/2021 |
| WO | WO-2022/006427 | A1 | 1/2022 |

OTHER PUBLICATIONS

Alesso et al., "Improving resins for solid phase synthesis: incorporation of I-[2-(2-methoxvethoxv) ethoxv]4-vinvl-benzene" Tetrahedron: 59: 7163-7169 (2003).
Altschul et al., "Gapped BLAST and PSI-BLAST: A New Generation of Protein Database Search Programs," Nucleic Acids Res., 25(27): 3389-3402 (1997).
Anderson et al., "Antileukemic Activity of Derivatives of I,2-Dimethyl-3,4-bis(hydroxymethyl)-5-phenylpyrrole Bis(N-methylcarbamate)", J. Med. Chem., 22(8): 977-980 (1979).
Anderson et al., "Practical process research and development: a guide for organic chemists", 38 pages (2012).
Annex et al., "Growth Factor-Induced Therapeutic Angiogenesis in the Heart: Protein Therapy," Cardiovascular Research, 65(3): 649-655 (2005).
Ardelt et al., "Estradiol Regulates Angiopoietin-1 mRNA Expression Through Estrogen Receptor-a in a Rodent Experimental Stroke Model," Stroke, 36: 337-341 (2005).
Auerbach et al., "Angiogenesis Assays: A Critical Overview," Clinical Chemistry, 49: 32-40 (2003).
Barany et al., "Solid-phase Peptide Synthesis: A Silver Anniversary Report," Int. J. Peptide Protein Res., 30( 6): 705-739 (1987).
Bartlett et al., "Caveat: A Program to Facilitate the Structure-derived Design of Biologically Active Molecules", Molecular Recognition in Chemical and Biological Problems, Special Pub., Royal Chem. Soc., 78: 182-196 (Apr. 1989).
Bohm, "The Computer Program LUDI: A New Method for the Novo Design of Enzyme Inhibitors," J. Computer-Aided Molecular Design, 6: 61-78 (1992).
Branden et al., "Introduction to Protein Structure Second Edition," Garland Publishing, Inc., New York: 374-375 (1999).
Brittain et al., "Polymorphism in Pharmaceutical Solids." Drugs and the Pharmaceutical Sciences, 2nd Edition, Edited by Brittain H.G., 192: 333-335 (2009).
Burger, "Isosterism and biososterism in drug design", Progress in Drug Research, Birkhauser Verlag (1991).
Bussolino, "Molecular Mechanisms of Blood Vessel Formation," Trends Biochem. Sci., 22(7): 251-256 (1997).
Byrn et al., "Pharmaceutical Solids: A Strategic Approach to Regularity Considerations", Pharmaceutical Research, 12(7): 945-954 (1995).
Carey, FA., Organic Chemistry 6th Ed. McGraw Hill, chapter 1, p. 9, chapter 19, pp. 839-840 and chapter 27, pp. 1182-1183 (2006).
CAS Registry Nos. 1261773-17-4, 1261723-73-2. Chemcats, 2 pages (2011).
CAS Registry Nos. 1261813-98-2, 1261613-86-8, and 1261518-21-1. Chemcats, (2011).
CAS Registry Nos. 1261871-80-0, 1261813-98-2, 1261789-32-5, 1261613-86-8, 1261575-91-0, 1261518-21-1, 1261513-56-7, 1261450-55-8, 1261442-66-3, as cited in the English translation of the Office Action received for Russian Federation Application No. 2016139352, dated Jan. 27, 2020. 14 pages.
CAS Registry Nos. 1361609-40-6, 1361556-21-9, 1361555-42-1, 1361544-77-5, 1361480-63-8, 1361477-92-0. Chemcats, 6 pages (2012).
CAS Registry Nos. 1361809-77-9, 1361737-20-3, 1361721-11-0, 1361693-45-9, 1361676-79-0. Chemcats, 5 pages (2012).
Catrina et al., "Hyperglycemia Regulates Hypoxia-Inducible Factor-1α Protein Stability and Function," Diabetes 53: 3226-3232 (2004).
Cheeseright, "The Identification of Bioisosteres as Drug Development Candidates", Innovations in Pharmaceutical Technology, issue 28 (2009).
Cherng, "Synthesis of substituted pryidines by the reactions of halopyridines with sulfur, oxygen and carbon nucleophiles under focused microwave irradition", Tetrahedron, Jun. 10, 2002, 58(24): 4931-4935 (2002).
Clinicaltrials.gov: archive: NCT01235936 Nn 2012_09_30[online]. U.S. National Institute of Health, Aug. 30, 2012; retrieved from the internet at <http:clinicaltrials.gov/archive/NCT01235936/2012_09_30> (Aug. 30, 2012). 3 pages.
Costello et al., "Evidence for changes in RREB-1, ZIP3, and zinc in the early development of pancreatic adenocarcinoma", J Gastrointest Canc, 43: 570-578 (2012).
Cousins, "Retina Today", 2 pages; retrieved from the internet at http:/retinatoday.com/2009/10/1009_12.oho (Oct. 2009).
Cunliffe et al., "Novel Inhibitors of Prolyl4-Hydroxylase. 3. Inhibition by the Substrate Analogue N-Oxaloglycine and Its Derivatives," J. Med. Chem. 35: 2652-2658 (1992).
Demetriades et al., "Dynamic combinatorial chemistry employing embryonic boronic acids-boronate esters leads to potent oxygenase inhibitors", Angewandte Chemie, International Edition, Mav 25, 2012, 51(27): 6672-6675 (2012).
Designation of Inventors filed on entry into EP Regional Phase of EP Pat. No. 2044005, 2 pages (2009).
Dranoff, "GM-CSP-secreting melanoma vaccines", Oncogene, 22: 3188-3192 (2003).
Elson et al., "Induction of hypervascularity without leakage or inflammation in transgenic mice overexpressing hypoxia-inducible factor-1α," Genes & Dev., 15: 2520-2532 (2001).
Elvidge et al., "Concordant Regulation of Gene Expression by Hypoxia and 2-Oxoglutarate-dependent Dioxygenase Inhibition", J. Biol. Chem., 281(22): 15215-15226 (2006).
Enoch et al., "ABC of wound healing. Non-surgical and drug treatments", BMJ, 332(7546):332:900-3 (2006).
European Patent Office, Interlocutory Decision in Opposition Proceedings date May 3, 2013 for European Patent No. 2044005, 2 pages.
European Patent Office, Minutes of the Oral Proceedings Before the Opposition Division dated May 3, 2013 for European Patent No. 2044005, 6 pages.
Extract from USPTO patent assignment database regarding U.S. Appl. No. 11/821,936. 1 page.

(56) References Cited

OTHER PUBLICATIONS

Favier et al., "HIF2α reduces growth rate but promotes angiogenesis in a mouse model of neuroblastoma", BMC Cancer, 7:139: 1-10 (2007).
Flower, "Modelling G-protein-coupled receptors for drug design," Biochimica et Biophysica Acta, 1422: 207-234 (1999).
Folkman et al., "Tumor Angiogenesis," The Molecular Basis of Cancer, Mendelsohn et al., eds., W. B. Saunders, Chapter 10: 206-232 (1995).
Franklin et al., "Approaches to the Design of Anti-Fibrotic Drugs," Biochem. Soc. Trans., 19(4): 812-5 (Nov. 1991).
Gaunt, "Rational Design of Benzyl-Type Protecting Groups Allows Sequential Deprotection of Hvdroxyl Groups by Catalytic Hydrogenolysis", 63(13): 4172-4173 (1998).
Gavhane et al., "Solid tumors: Facts, challenges, and solutions", International Journal of Pharma Sciences and Research, 2(1): 1-12 (2011).
Goodford, "A Computational Procedure for Determining Energetically Favorable Binding Sites on Biologically Important Macromolecules," J. Med. Chem., 28(7): 849-857 (1985).
Goodsell et al., "Automated Docking of Substrates to Proteins by Simulated Annealing", Proteins: Structure, Function, and Genetics, 8: 195-202 (1990).
Greer et al., "The updated biology of hypoxia inducible factor", EMBO J. 31: 2448-2460 (2012).
Hardcastle et al., "Discovery of Potent Chromen-4-one Inhibitors of the DNA-Dependent Protein Kinase (DNA-PK) Using a Small-Molecule Library Approach", J. of Medicinal Chem., 48(24): 7829-7846 (2005).
Hoeksema et al., "Structure of Rubradirin", J. of American Chem. Society, 104(19): 5173-5181 (1982).
Hu et al., "Differential Roles of Hypoxia-Inducible Factor 1α (HIF-1α) and HIF-2α in Hypoxic Gene Regulation", Mol. Cell. Biol., 23: 9361-9374 (2003).
Ingersoll et al. "Hippuric Acid", Organic Syntheses, CV 2, 328; retrieved from the internet at <http:web.archive.org/web20020724135719/http://orgsyn.org/orgsyn/prepContent.asp?prep=cv 2p032 8> on Mar. 11, 2010. 4 pages.
International Preliminary Report on Patentability dated Dec. 10, 2013 for PCT/US2012/40833. 7 pages.
International Preliminary Report on Patentability dated Nov. 10, 2020 for PCT/US2019/031310. 6 pages.
International Search Report and Written Opinion dated Apr. 20, 2015 for PCT/US2015/12634. 9 pages.
International Search Report and Written Opinion dated Aug. 29, 2012 for PCT/US2012/40833. 9 pages.
International Search Report dated Apr. 14, 2008 for PCT/US2007/014832. 3 pages.
International Search Report and Written Opinion, dated Aug. 7, 2019 for PCT/US2019/031310. 10 pages.
International Search Report and Written Opinion, dated Nov. 16, 2021 for PCT/US2021/040138. 20 pages.
International Union of Pure and Applied Chemistry, Glossary of Class Names of Organic Compounds and Reactive Intermediates Based on Structure, Pure & D Annl. Chem., 67(8-9): 1307-1375 (1995).
Ivan et al., "Biochemical purification and pharmacological inhibition of a mammalian prolyl hydroxylase acting on hypoxia-inducible factor," Proceedings of the National Academy of Science, 99(21): 13459-13464 (2002).
Ivan et al., "HIFα Targeted for VHL-Mediated Destruction by Proline Hydroxylation: Implications for 02 Sensing", Science, 292: 464-468 (2001).
Ivanisevic et al., "Uses of X-Ray Powder Diffraction in the Pharmaceutical Industry." Pharmaceutical Formulation & Quality. Aug.-Sep. 2011: 30-33 (2011).
Iyoda et al., "Homocoupling of aryl halides using nickel(II) complex and zinc in the presence of Et4NI. An efficient method for the synthesis of biaryls and bipyridines", Bull. Chem. Soc. Jpn., 63(1): 80-87 (1990).
Jaakkola et al., "Targeting of HIF-α to the von Rippel-Lindau Ubiquitylation Complex by O2-Regulated Prolyl Hydroxylation," Science, 292: 468-472 (2001).
Jones et al., "Molecular Recognition of Receptor Sites Using a Genetic Algorithm with a Description of Desolvation", J. Mol. Biol., 245: 43-53 (1995).
Kabachnik et al.: "Synthesis of new quaternary phosphonium salts," Russian Journal of Organic Chemistry, vol. 35, 1999, pp. 26-27, XP009529980, p. 26, left column, paragraph 2: compound le; p. 27, table: compound le, mp. 104C. 2 pages.
Kaelin, "Proline Hydroxylation and Gene Expression," Annual Rev. Biochem., 74: 115-125 (2005).
Karuppagounder et. al., "Hypoxia-inducible factor prolyl hydroxylase inhibition: robust new target or another big bust for stroke therapeutics?", J. Cereb. Blood F. Met., 32: 1347-1361 (2012).
Kawashima et al., "Suppressive effect of quinolinic acid and hippuric acid on bone marrow erythroid growth and lymphocyte blast formation in uremia", Advances in Experimental Medicine and Biology, 223: 69-72 (1987).
Ke and Costa, "Hypoxia-Inducible Factor-I (HIF-1)", Molecular Pharmacology, 70(5): 1469-1480 (2006).
Khandhadia et al., "Neurodegenerative Diseases", edited by Shamim I. Alnned, Published by Landes Biosciences and Springer Science+ Business Media, Chapter 2: 15-36 (2012).
Kietzmann et al., "Perivenous expression of the mRNA of the three hypoxia-inducible factor a-subunits, HIF1α, HIF2α and HIF3α, in rat liver", Biochem. J., 354: 531-537 (2001).
Kim et al., "Recent advances in developing inhibitors for hypoxia-inducible factor prolyl hydroxylases and their therapeutic implications", Molecules, 20: 20551-20568 (2015).
Krantz, "Erythropoietin," Blood, 77: 419-434 (1991).
Kuntz et al., "A Geometric Approach to Macromolecule—Ligand Interactions," J. Mol. Biol., 161: 269-288 (1982).
Kurti et al., "Strategic applications of named reactions in organic synthesis", El Sevior: 448-449 and 484-485 (2005).
Langsetmo et al., "Inhibition of HIF-Prolyl Hydroxylases with FG-4539 Is Neuroprotective in a Mouse Model of Permanent Focal Ischemia", International Stroke Conference, Kissimmee Florida, Presentation No. 427 (2006).
Lee et al., "Structure of Human FIH-1 Reveals a Unique Active Site Pocket and Interaction Sites for HIF-1 and von Hippel Lindau", JBC, 278: 7558-7563 (2003).
Li et al., "PR39, A Peptide Regulator of Angiogenesis," Nat Med., 6(1): 49-55 (2000).
Lima and Barreiro, "Bioisosterism: A Useful Strategy for Molecular Modification and Drug Design", Current Medicinal Chemistry, 12: 23-49 (2005).
Liu et al., "Hypoxia Induces Genomic DNA Demethylation through the Activation of HIF-1alpha and Transcriptional Upregulation of MAT2A in Hepatoma Cells", Mol. Cancer Ther., 10: 1113-1123 (Jun. 2011).
Mancini et al., "Effect of Erythropoietin on Exercise Capacity in Patients with Moderate to Severe Chronic Heart Failure", Circulation, 107: 294-299 (2003).
McDonough et al., "Cellular Oxygen Sensing: Crystal Structure of Hypoxia-Inducible Factor Prolyl Hydroxylase (PHD2)", PNAS, 103(26): 9814-9819 (2006).
Miranker et al., "Functionality Maps of Binding Sites: A Multiple Copy Simultaneous Search Method", Proteins: Structure, Function and Genetics, 11: 29-34 (1991).
Morissette et al., "High-throughput crystallization: polymorphs, salts, co-crystals and solvates of pharmaceutical solids", Advanced Drug Delivery Reviews, 56: 275-300 (2004).
Myerson, Handbook of Industrial Crystallization, p. 249 (2002).
Nguyen et al., "Cellular Interactions in Vascular Growth and Differentiation", Int. Review of Cytology, 204: 1-48 (2001).
Nielsen et al., "Antiangiogenic therapy for Breast Cancer", Breast Cancer Res. 12: 209-227 (2010).
Nishibata et al., "Automatic Creation of Drug Candidate Structures Based on Receptor Structure. Starting Point for Artificial Lead Generation", Tetrahedron, 47(43): 8985-8990 (1991).
Nowak et al., "Age-related macular degeneration (AMD): pathogenesis and therapy", Pharmacological Reports, 58: 353-363 (2006).

(56) References Cited

OTHER PUBLICATIONS

Online Abstract showing publication date of McDonough et al. as Jun. 16, 2006 (2006). 4 pages.
O'Reilly et al., "Angiostatin: A Novel Angiogenesis Inhibitor that Mediates the Suppression of Metastases by a Lewis Lung Carcinoma", Cell, 79: 315-328 (1994).
O'Reilly et al., "Endostatin: An Endogenous Inhibitor of Angiogenesis and Tumor Growth", Cell, 88: 277-285 (1997).
Pasqualetti et al., "Circadian rhythm of serum erythropoietin in myelodysplastic syndromes", European Review for Medical and Pharmacological Sciences, 4: 111-115 (2000).
PCT Request Form dated Jun. 26, 2007 for PCT/US2007/014832. 5 pages.
Pergola et al., "Vadadustat, a novel oral HIF stabilizer, provides effective anemia treatment in nondialysis-dependent chronic kidney disease", 90: 1115-1122 (2016).
Peyssonnaux et al., "HIF-1α Expression Regulates the Bactericidal Capacity of Phagocytes", J. Clinical Invest., 115(7): 1806-1815 (2005).
Piyamongkol et al., "Amido-3-hydroxypyridin-4-ones as Iron (III) Ligands", Chemistry A European Journal, 16: 6374-6381 (2010).
Prabhakar et. al., "Adaptive and Maladaptive Cardiorespiratory Responses to Continuous and Intermittent Hypoxia Mediated by Hypoxia-Inducible Factors 1 and 2", Physiol. Rev., 92: 967-1003 (2012).
PubChem Open Chemistry Database Compound Name: SCHEMBL3484399 (CID 49848485); Retrieved on from the internet: <https://pubchem.ncbi.nlm.nih.gov/compound/49848485> on Mar. 15, 2016. 13 pages.
PubChem Open Chemistry Database Compound Name: Zeadcohjerwfoi-Uhfffaoysa-M (CID 71491828); retrieved from the internet: <https://pubchem.ncbi.nlm.nih.gov/compound/71491828> on Mar. 21, 2016. 12 pages.
Qian et al., "A Randomized, Double-Blind, Placebo Controlled Trial of FG-4592 for Correction of Anemia in Subjects with Chronic Kidney Disease in China," Oral Abstract FR-ORO11, J. Am. Soc. Nephrol., 24: 38A (2013). 1 page.
Qunibi et al., "A randomized controlled trial comparing intravenous ferric carboxymaltose with oral iron for treatment of iron deficiency of non-dialysis-dependent chronic kidney disease patients", Nephrol Dial Transplant, 26(5): 1599-1607 (2011).
Rahtu-Korpela et al., "HIF Prolyl 4-Hydroxylase-2 Inhibition Improves Glucose and Lipid Metabolism and Protects Against Obesity and Metabolic Dysfunction," Diabetes 63: 3324-3333 (2014).
Rankin et al., "Hypoxia-inducible factor-2 (HIF-2) regulates hepatic erythropoietin in vivo" J. Clin. Invest. 117:1069-1076 (2007).
Ratcliffe et al., "HIF-1 and HIF-2: working alone or together in hypoxia?" J. Clin. Inv., 117(4):862-865 (2007).
Redondo et al., "Vascular endothelial growth factor (VEGF) and melanoma. N-Acetylcysteine downregulates VEGF production in vitro", Cytokine, 12(4):374-378 (2000).
Request for Correction of Inventorship at USPTO regarding U.S. Appl. No. 11/821,936, dated Jan. 16, 2009. 1 page.
Roda et al., "Stabilization of HIF-2α induces sVEGFR-1 production from tumor-associated macrophages and decreases tumor growth in a murine melanoma model", J. Immunology, 189: 3168-3177 (2012).
Schelhass and Waldmann, "Protecting Group Strategies in Organic Synthesis", Chem. Int. Ed. Engl., 36: 2056-2083 (1996).
Schmidt et al., "Synthesis of Alkoxy-Substituted Pyridines from Mono-and Triacationic Pyridinium Salts," Synthesis, vol. 2005, No. 05, Apr. 22, 2005, pp. 781-786, XP055840901, Stuttgart, DE. ISSN:0039-7881, DOI: 10.1055/s-2005-861827 p. 781, scheme 1: compounds 1, 2; p. 782, scheme 2 and table 1. 6 pages.
Schoneberg et al., "Structural Basis of G Protein-Coupled Receptor Function," Molecular and Cellular Endocrinology, 151: 181-193 (1999).
Search Report dated Mar. 18, 2011 for European Pat. App. No. 11000872.9. 3 pages.
Semenza et al., "Regulation of Erythropoietin Production: New Insights into Molecular Mechanisms of Oxygen Homeostasis", Hematol. Oncol. Clin. North Am., 8: 863-884 (1994).
Semenza et al., "Transcriptional Regulation of Genes Encoding Glycolytic Enzymes by Hypoxia-Inducible Factor I", J. Biol. Chem., 269: 23757-23763 (1994).
Semenza, "HIF-1 and human disease: one highly involved factor", Genes & Development, 14: 1983-1991 (2000).
Semenza, "Signal Transduction to Hypoxia-inducible Factor I ", Biochem. Pharrnacol, 64: 993-998 (2002).
Sexton, "Recent advances in our understanding of peptide hormone receptors and RAMPS", Current Opinion in Drug Discovery and Development, 2(5): 440-448 (1999).
Seymour et al., "Decision T 0777-08 of the Boards of Appeal of the European Patent Office", retrieved from the internet: <http://www.epo.org/law-practice/case-law-appeals/pdf/1080777exl.pdf> on Dec. 19, 2017 (2011).
Sheehan, "3-Hydroxypicolinic Acid and Some of its Derivatives", J. Organic Chemistry 31(3): 636-638 (1996).
Siddiq, "Hypoxia-inducible factor prolyl 4-hydroxylase inhibition", J. of Biological Chemistry, 280(50):41732-41743 (2005).
Sowter et al., "Predominant Role of Hypoxia-Inducible Transcription Factor (Hif)-1α versus (Hif)-2α in Regulation of the Transcriptional Response to Hypoxia", Cancer Res. 63: 6130-6134 (2003).
Sporn and Suh, "Chemoprevention of cancer", Carcinogenesis, 21(3): 525-530( 2000).
Stille, J. K., Angew. Chem., Int. ED. Engl., vol. 25: 508 (1986).
Stohlawetz et al., "Effects of erythropoietin on platelet reactivity and thrombopoiesis in humans", Blood, 95(9): 2983-2989 (2000).
Sutter, "Hypoxia-inducible factor 1 alpha protein expression is controlled by oxygen-regulated ubiquitination that is disrupted by deletions and missense mutations", PNAS, 97(9): 4748-4753 (2000).
Teicher et al., "Potentiation of Cytotoxic Cancer Therapies by TNP-470 Alone and with Other Anti-Angiogenic Agents", Int. J. Cancer, 57: 920-925 (1994).
Thoppil and Bishayee, "Terpenoids as potential chemopreventive and therapeutic agents in liver cancer", World J. Hepatol., 3(9): 228-249 (2011).
Thornber, "Isosterism and Molecular Modification in Drug Design", Progress Drug Res., vol. 37: 563-580 (1979).
Tzschucke et al., "Fluorous-Silica-Supported Perfluoro-Tagged Palladium Complexes Catalyze Suzuki Coupling in Water", Helvetica Chimica Acta; 87: 2882-2889 (2004).
Ullmann F., J. Bielecki, Ber. Deutsch. Chem. Ges. 1901, p2174, 34. (1901) 12 pages.
Variankaval et al., "From form to function: crystallization of active pharmaceutical ingredients", AICHE Journal, Jul. 2008, 54(7): 1682-1688 (2008).
Vickerstaffe et al., "Fully Automated Polymer-Assisted Synthesis of 1,5-Biaryl Pvrazoles", J. Comb. Chem., 6:332-33 (2004).
Vincent et al., "Angiogenesis is Induced in a Rabbit Model of Hindlimb Ischemia by Naked DNA Encoding an HIF-1α-VP16 Hybrid Transcription Factor", Circulation, 102: 2255-2261 (2000).
Vippagunta et al., "Crystalline solids", Adv. Drug Deliv. Rev., 48(1): 3-26 (2001).
Wade et al., "Organic Chemistry", 6th ED., Pearson Prentice Hall, US: 780-781 (2006).
Warnecke et al., "Activation of the Hypoxia-Inducible Factor Pathway and Stimulation of Angiogenesis by Application of Prolyl Hydroxylase Inhibitors", FASEB Journal, 17: 1186-1188 (2003).
Warshakoon et al., "Design and synthesis of substituted pyridine derivatives as HIF-1alpha prolyl hydroxylase inhibitors", Bioorganic & Medicinal Chemistry Letters, 16: 5616-5620 (2006).
Wax et al., "SM-20 is a Novel20-kd Protein Whose Expression in the Arterial Wall is Restricted to Smooth Muscle", Lab. Invest., 74(4): 797-808 (1996).
Weidner et al., "Tumor Angiogenesis and Metastasis—Correlation in Invasive Breast Carcinoma", New Eng. J. Med., 324(1): 1-8 (1991).
Wiesener et al., "Widespread hypoxia-inducible expression of HIF-2alpha in distinct cell populations of different organs." FASEB J. 17(2): 271-3 (2003).

(56) References Cited

OTHER PUBLICATIONS

Wright et al., "Activation of the Prolyl Hydroxylase Oxygen-Sensor Results in Induction of GLUTI, Heme Oxygenase-1, and Nitric-Oxide Synthase Proteins and Confers Protection from Metabolic Inhibition to Cardiomyocytes", J. Bio. Chem., 278(22): 20235-20239 (2003).
Wu et al., "A systems biology perspective on sVEGFR1: its biological function, pathogenic role and therapeutic use", J. Cell. Mol. Med. 14:528-552 (2010).
Yang et al., "Desmoplakin acts as a tumor suppressor by inhibition of the Wnt-beta-catenin signaling pathway in human lung cancer", Carcinogenesis, 33(10): 1863-1870 (2012).

* cited by examiner

METHOD FOR PRODUCING NITROGEN-CONTAINING HETEROARYLCARBOXAMIDE ACETIC ACID DERIVATIVE

CROSS-REFERENCE TO RELATED APPLICATIONS

The present application is a 35 U.S.C. § 371 National Stage Application of International Application No. PCT/JP2020/045871, filed on Dec. 9, 2020, which claims benefit of and priority to Japanese Application No. 2019-222845, filed Dec. 10, 2019, the contents of which are each herein incorporated by reference in their entirety.

TECHNICAL FIELD

The present invention relates to a process for preparing a nitrogen-containing heteroarylcarboxamide acetic acid derivative.

BACKGROUND ART

It is reported that a [5-(3-chlorophenyl)-3-hydroxypyridine-2-carboxamide]acetic acid (hereinafter, referred to as "compound [I(A)]" or "Vadadustat") as one kind of a nitrogen-containing heteroarylcarboxamide acetic acid derivative shows HIF-1α prolyl hydrolase inhibitory activity, and improves a blood flow, an oxygen delivery, and an energy utilization in ischemic tissue, or -upregulate a production of erythropoietin for treatment of anemia (see Patent Literature 1).

[Chemical Formula 1]

I(A)

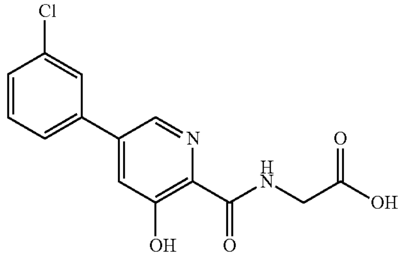

According to the disclosure of the Patent Literature 1, the compound [I(A)] can be prepared according to the Reaction scheme (I) below.

Reaction Scheme (1)

[Chemical Formula 2]

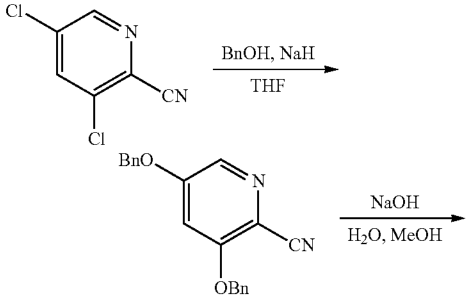

-continued

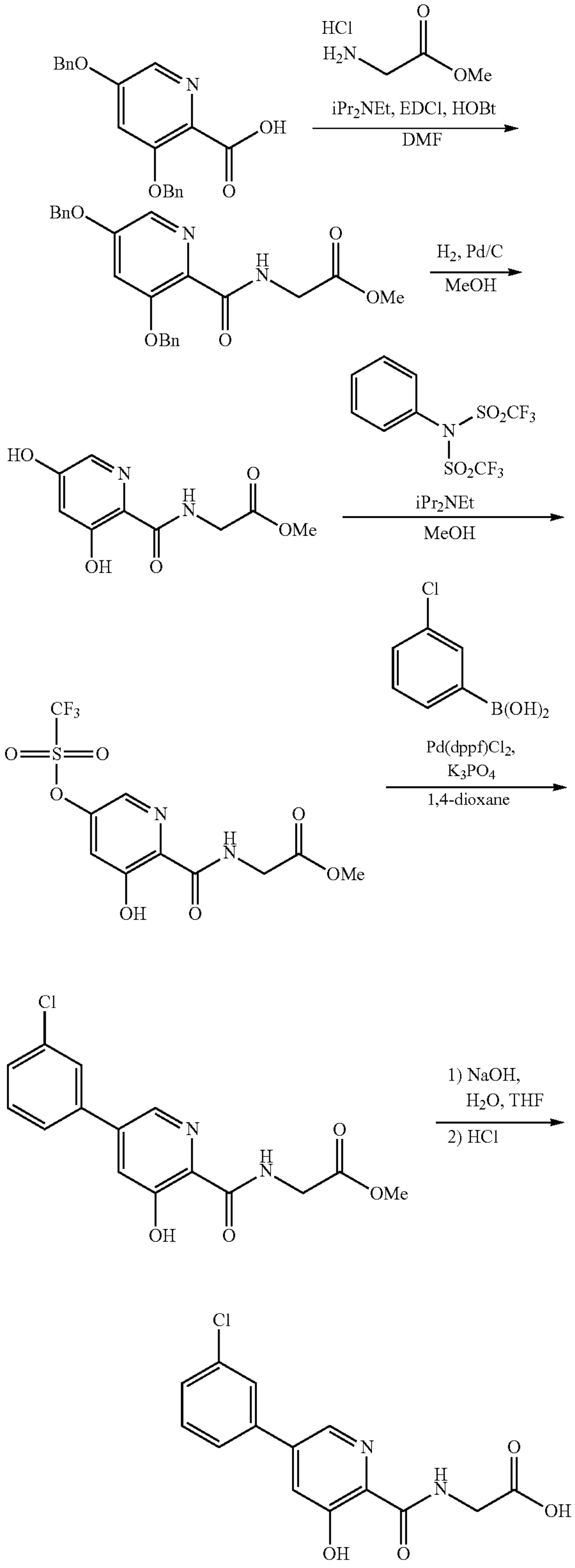

In the Patent Literature 2, some other processes for preparing the compound [I(A)] are disclosed. According to the descriptions of this patent literature, the compound [I(A)] can be prepared according to the Reaction Scheme (2) below.

Reaction Scheme (2)

[Chemical Formula 3]

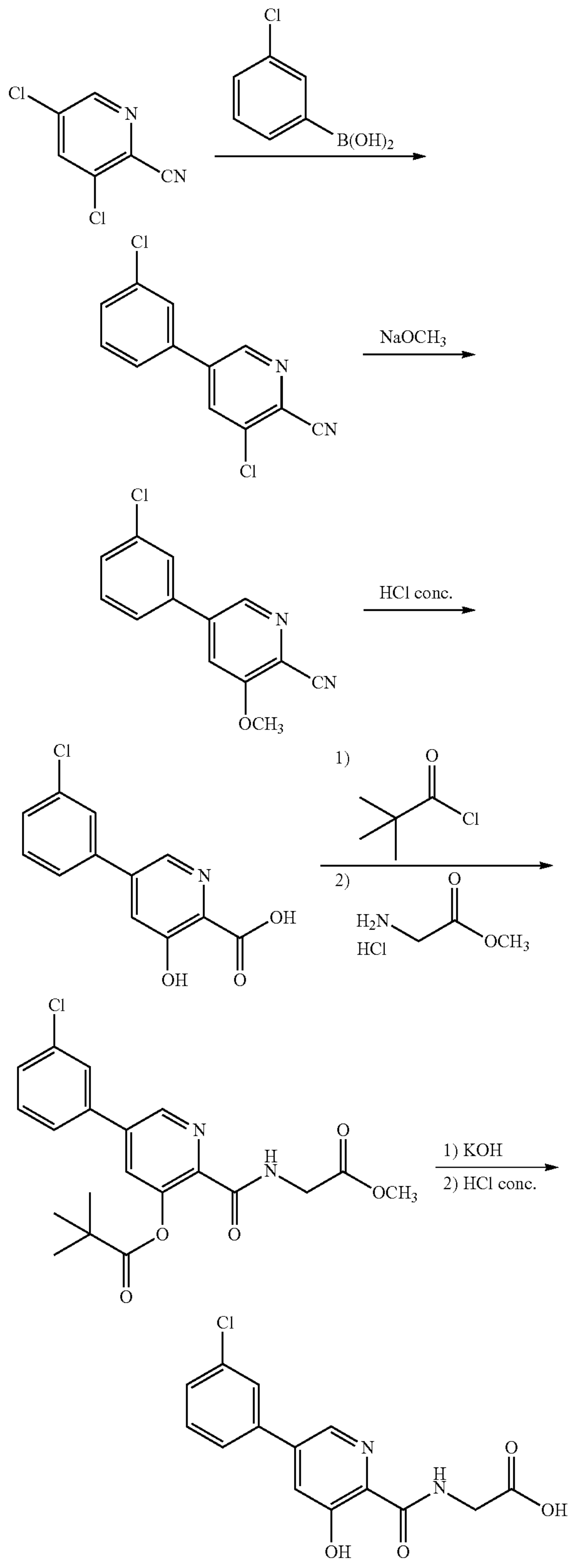

I(A)

However, the production steps in these Reaction Schemes of starting with 2-cyano-3,5-dichloropyridine used as a starting material and ending with the compound [I(A)] are long, and the starting materials are expensive, and the production scheme is thus not said to be an optimal process for conducting on industrial scale.

In the Patent Literature 3, further other some processes for preparing the compound [I(A)] are disclosed. According to the descriptions of the Patent Literature, the compound [I(A)] can be prepared according to the Reaction Scheme (3) below.

Reaction Scheme (3)

[Chemical Formula 4]

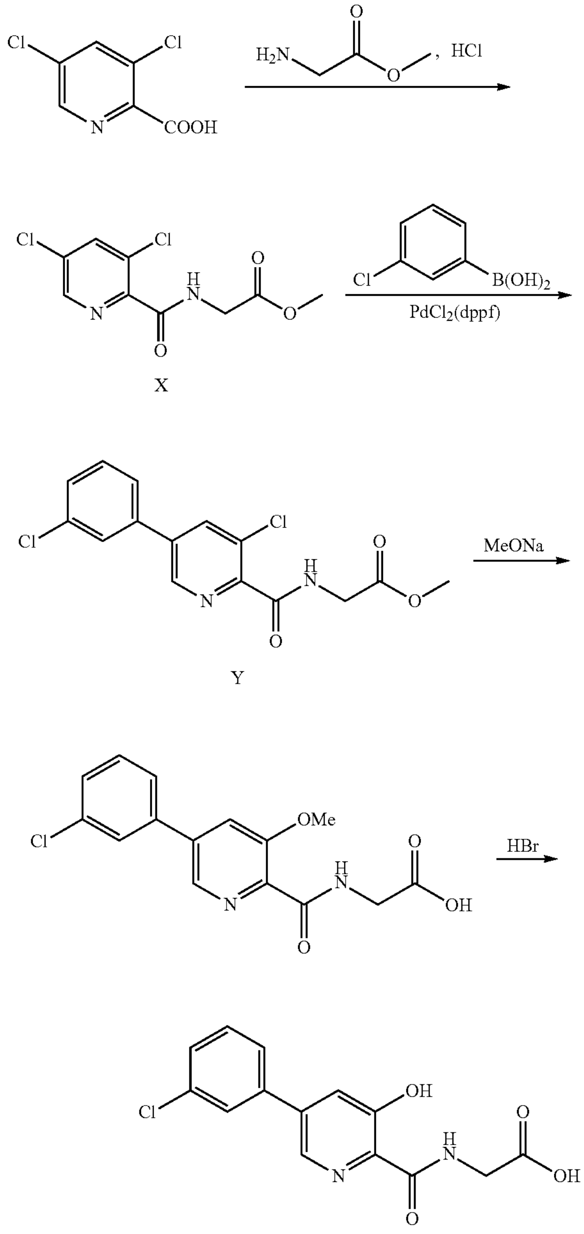

X

Y

I

However, 3,5-dichlopyridine-2-carboxylic acid used as a starting material in the Reaction Scheme is expensive, and the production scheme is thus not said to be an optimal process for conducting on industrial scale.

Further, in the Patent Literature 4, which was published after the filing of JP 2019-222845 as the basis of the priority of the present application, the process for preparing the intermediate compound (3×) and the intermediate compound (4) for the compound [I(A)] as shown in Reaction Scheme (4) below are disclosed. According to the descriptions of the Patent Literature, the compound (X) and the compound (2×) can be reacted in the presence of carbon monoxide to prepare the intermediate compound (3×). Further, the intermediate compound (3×) and a 3-chlorophenyl boronic acid are reacted according to the Suzuki coupling reaction to prepare the intermediate compound (4×).

Reaction Scheme (4)

[Chemical Formula 5]

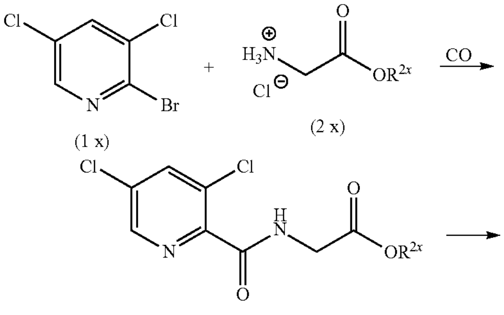

(1 x) (2 x) (3 x)

-continued

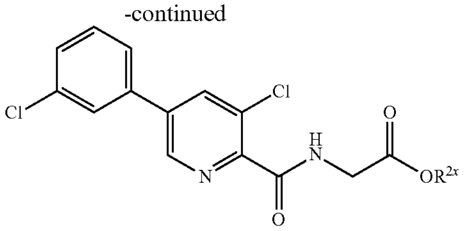

(4 x)

However, in the Working Examples of this application describing the preparation of the intermediate compound (4×), it is just confirmed a reaction efficiency by analyzing the reaction solution of the reaction. The patent literature neither disclose that the intermediate compound (4×) is isolated and purified and is then subjected to an instrumental analysis, nor disclose any grounds for the fact where the reaction can progress with high regioselectivity at the 5-position chlorine atom among two chlorine atoms at the 3-position and 5-position in the intermediate compound (3×) to produce the intermediate compound (4×).

Also as one kind of the nitrogen-containing heteroarylcarboxamide acetic acid derivative, 2-(4-hydroxy-1-methyl-7-phenoxyisoquinoline-3-carboxamide)acetic acid (hereinafter, referred to as "Compound [I(B)] or Roxadustat") is reported. According to the Patent Literature 5, the compound [I(B)] can be prepared according to the Reaction Scheme (5) below.

Reaction Scheme (5)

[Chemical Formula 6]

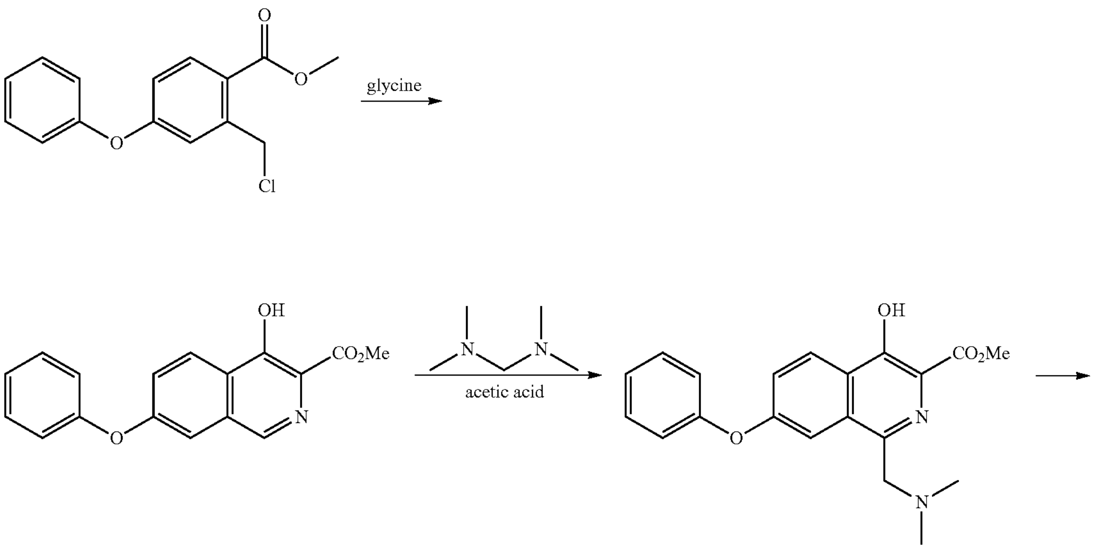

-continued

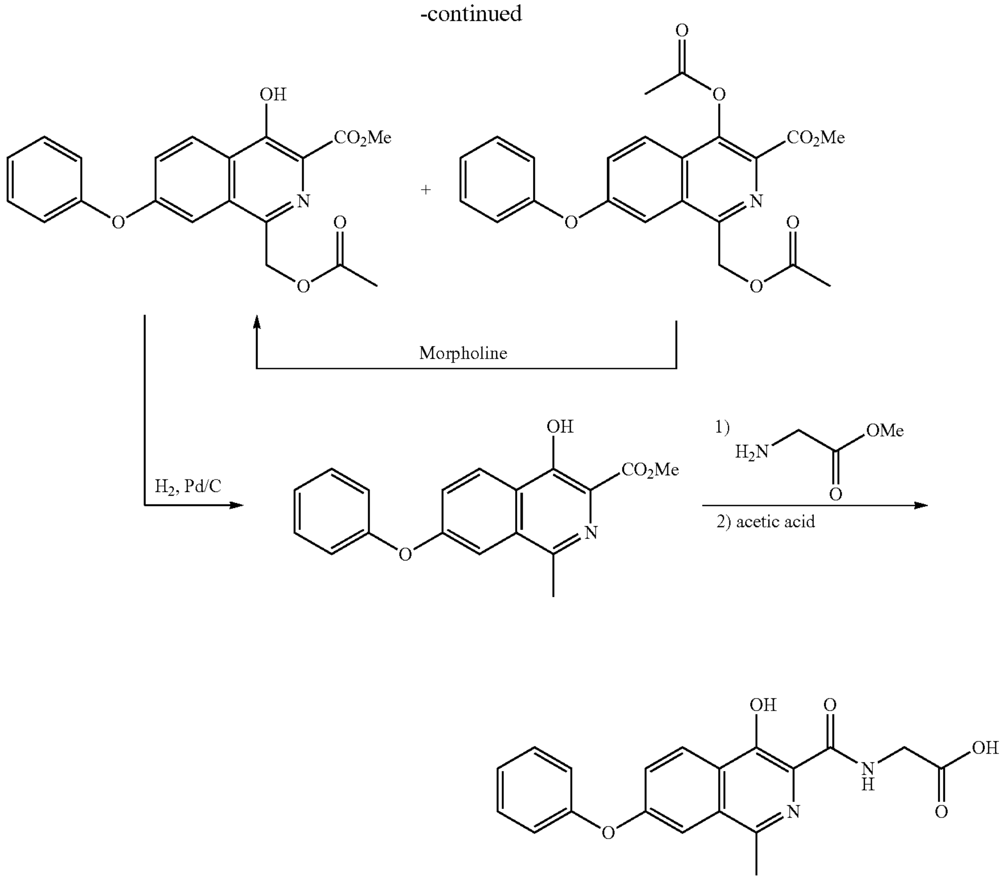

I(B)

However, the production steps of starting with methyl 2-chloromethyl-4-phenoxy benzoate used as a starting material and ending with the compound [I(B)] are long, and the production scheme is not said to be optimal process for conducting on industrial scale.

CITATION LIST

Patent Literature

Patent Literature 1: WO 2008/002576
Patent Literature 2: WO 2012/170377
Patent Literature 3: CN 105837502A
Patent Literature 4: WO 2020/217733
Patent Literature 5: WO 2014/014834

SUMMARY OF THE INVENTION

Problems to be Solved by Invention

The present invention provides a novel process for preparing compound [I] including the above-mentioned compound [I(A)] and compound [I(B)] each compound being useful as a medicament in an industrially advantageous manner.

Here the present inventors etc. tried a method for converting the compound (X) described in the above Patent Literature 3 into the compound (Y), the Suzuki coupling reaction hardly progressed, and the coupling products slightly obtained was a regioisomer which was reacted at the pyridine group at the 3-position, and accordingly, the desired product (Y) could not been prepared. Also, in the above Patent Literature 4, a reaction was conducted according to a similar method to that of the Patent Literature 3 as a reference and it can be presumed in this case that the regioisomer produced by the reaction at the pyridine group at the 3-position was produced similarly, considering the additional test results described in the Patent Literature 3 filed by the above-mentioned same inventors etc. as those of the present application.

Means to Solve Problems

The present inventors have intensively studied to solve the above problems, and a result, found out that according to the processes consisting of the below-mentioned Reaction Schemes (I) {(I-I) to (I-VII)}, (II) {(II-I) to (I-III)}, and (III), in contrast to the processes of the Patent Literatures 1 and 2 in which 2-cyano-3,5-dichlopyridine is used as a starting material, 2-halogeno-pyridine was subjected to an aminocarbonyl reaction to prepare the desired compound [I(A)] in more shorten steps starting with lower cost starting material, and then completed the present invention. Further, the present inventors etc. found that the desired compound (I) containing [(4-hydroxy-1-methyl-7-phenoxyisoquinoline)-3-carboxamide]acetic acid (hereinafter, referred to as "compound [I(B)]" or "Roxadustat") can be also prepared, and then completed the present invention.

[Chemical Formula 7]

I

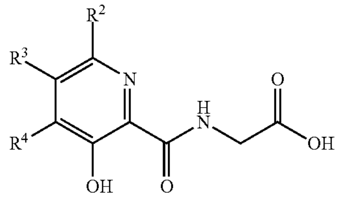

I(A)

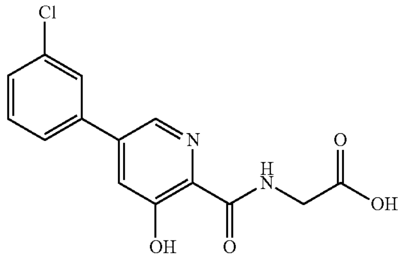

I(B)

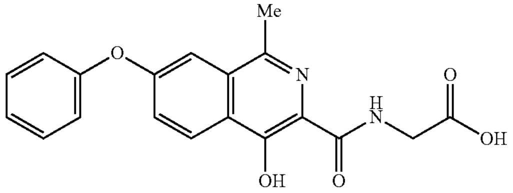

Also, though the compound (a3-1-A) below is disclosed in the Patent Literature 1, the Patent Literature 1 neither describes the solid state, the physical properties and the crystal form of the compound (a3-1-A) therein, nor suggests the presence of the crystal form of the same.

[Chemical Formula 8]

a3-1-A

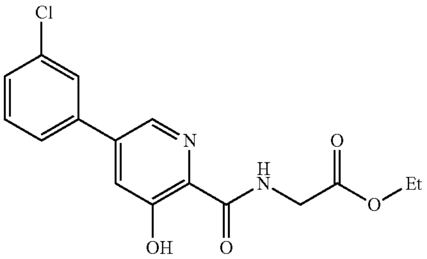

The present inventors etc. can have some findings that the residual of impurity materials becomes any problems in the preparation of the compound [I(A)]. As the results of various studies on purification method, it is possible to remove impurity materials more effectively by crystalizing the intermediate compound of the compound (a3-1-A) and then purifying the same compound to prepare the compound [I(A)] with high quality. That is, two kinds of crystal forms are existed in the compound (a3-1-A), and these two kinds of crystals can be purified to remove impurity materials effectively. Particularly, the II type crystal is better to remove impurity materials effectively. Whilst, the I type crystal is a crystal having most high thermodynamical stability, which is preferred in terms of the robustness of the process.

That is, the present invention includes the followings, however, which are not limited thereto.

[1]A process for preparing a compound (a3) below which comprises reacting a compound (a1) represented by formula:

[Chemical Formula 9]

a1

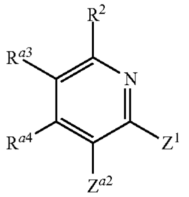

{wherein $R^2$ represents a hydrogen atom or an optionally substituted methyl group, $R^{a3}$ represents a phenyl group which may be optionally substituted with halogen atom, $R^{a4}$ represents a hydrogen atom, or alternatively, $R^{a3}$ and $R^{a4}$ bind to each other and combine together with a pyridine group to which they are adjacent to form an isoquinoline group which may be optionally substituted with phenyloxy group, $Z^1$ represents a chlorine atom, a bromine atom, or an iodine atom, $Z^{a2}$ represents a hydroxy group or a substituent represented by formula:

[Chemical Formula 10]

(wherein $P^1$ represents a protecting group for hydroxy group)} or a compound (2) represented by formula:

[Chemical Formula 11]

2

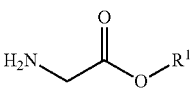

(wherein $R^1$ represents an optionally substituted alkyl group, a hydrogen atom, or a resin residue)

or a salt of the compound (2), with a carbon monoxide, in the presence of a palladium catalyst, in the presence or absence of a ligand, in the presence of a base, in a solvent, to obtain the compound (a3) represented by formula:

[Chemical Formula 12]

a3

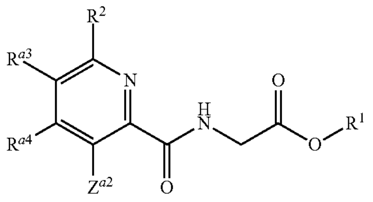

(wherein the symbols are the same as defined above).

[2] The process according to [1] wherein a pressure of a carbon monoxide during the reaction is 0.01 MPa to 1 MPa.

[3] The process according to [1] or [2] wherein the molar ratio of the compound (a1) used in the reaction to the compound (2) used in the reaction is 2:1 to 1:2.

[4] The process according to any one of [1] to [3] wherein the reaction is conducted in nitriles as the solvent and at 20 to 150° C. as a reaction temperature.

[5]A compound as claimed in any one of [1] to [4] wherein the compound (a1) represents a compound (a1-5-a) represented by formula:

[Chemical Formula 13]

a1-5-a

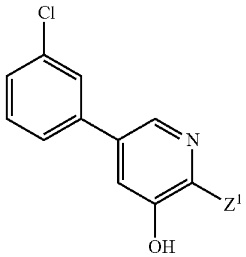

(wherein $Z^1$ represents a chlorine atom, a bromine atom or an iodine atom), and the compound (a3) represents a compound (a3-3-a) represented by formula:

[Chemical Formula 14]

a3-3-a

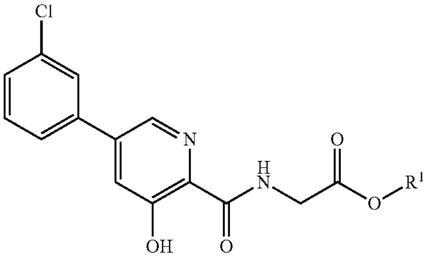

(wherein $R^1$ represents an optionally substituted alkyl group, a hydrogen atom or a resin residue).

[6]A process which comprises conducting a reaction according to any one of [1] to [4] to prepare a compound (a3-1):

[Chemical Formula 15]

a3-1

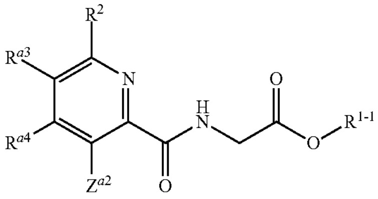

(wherein $R^{1-1}$ represents an optionally substituted alkyl group or a resin residue, $R^2$ represents a hydrogen atom or an optionally substituted methyl group, $R^{a3}$ represents a phenyl group which may be optionally substituted with halogen atom, and $R^{a4}$ represents a hydrogen atom, or alternatively, $R^{a3}$ and $R^{a4}$ bind to each other and combine together with a pyridine group to which they are adjacent to form an isoquinoline group which may be optionally substituted with phenyloxy group, $Z^{a2}$ represents a hydroxy group or a substituent represented by formula:

[Chemical Formula 16]

(wherein $P^1$ represents a protecting group for hydroxy group)} and converting the compound (a3-1) into the compound (aI) represented by formula:

[Chemical Formula 17]

aI

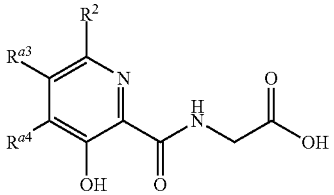

{wherein the symbols are the same as defined above}.

[7] The process according to any one of [1] to [4] and [6], wherein (i) $R^2$ represents a hydrogen atom, $R^{a3}$ represents a 3-chlorophenyl group, and $R^{a4}$ represents a hydrogen atom, or alternatively, (ii) $R^2$ represents a methyl group, and $R^{a3}$ and $R^{a4}$ bind to each other and combine together with a pyridine group to which they are adjacent to form a 7-phenyloxy-isoquinoline group.

[8] The process according to [6] wherein the compound (a3-1) represents a compound (a3-2-a) represented by formula: [Chemical Formula 18]

[Chemical Formula 18]

a3-2-a

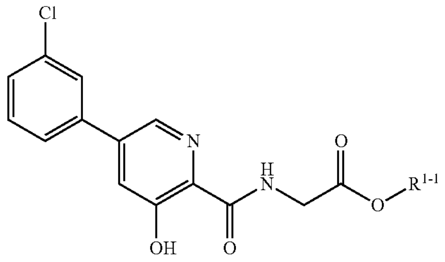

(wherein $R^{1-1}$ represents an optionally substituted alkyl group or a resin residue), and the compound (a1) represents a compound [I(A)] represented by formula:

[Chemical Formula 19]

I(A)

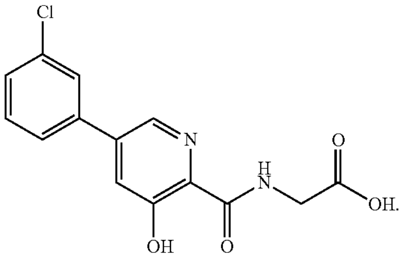

[9] The process according to any one of [1] to [4] and [6] wherein the compound (a1) represents a compound (a1-1-a) represented by formula:

[Chemical Formula 20]

a1-1-a

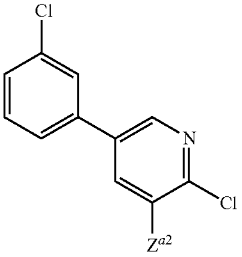

{wherein $Z^{a2}$ represents a hydroxy group or a substituent represented by formula:

[Chemical Formula 21]

(wherein $P^1$ represents a protecting group for hydroxy group)} and the compound (a1-1-a) is the compound (a1-1-a) prepared by reacting a compound (a4) represented by formula:

[Chemical Formula 22]

a4

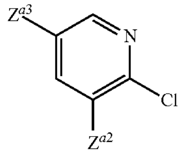

(wherein $Z^{a3}$ represents a bromine atom, an iodine atom, or a trifluoromethanesulfoxy group, and $Z^{a2}$ is the same as defined as above.)

with a compound (a5) represented by formula:

[Chemical Formula 23]

a5

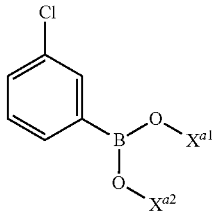

(wherein $X^{a1}$ and $X^{a2}$ each independently represents a hydrogen atom or an alkyl group, or alternatively both of them bind to each other to form an alkylene group), or an equivalent compound to the compound (a5) in the presence or absence of a base, in the presence or absence of a palladium catalyst, in the presence or absence of a ligand, in a solvent or in the absence of a solvent.

[10] The process according to [9] wherein the compound (a1-1-a) represents a compound (a1-4-a) represented by formula:

[Chemical Formula 24]

a1-4-a

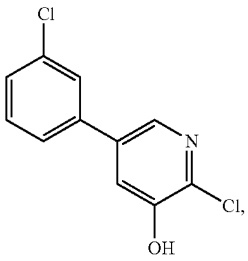

and the compound (a4) represents a compound (a4-2) represented by formula:

[Chemical Formula 25]

a4-2

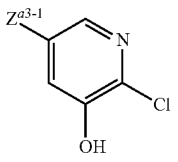

(wherein $Z^{a3}$ represents a bromine atom or an iodine atom). [11]A process for processing a compound [I(A)] represented by formula:

[Chemical Formula 26]

I(A)

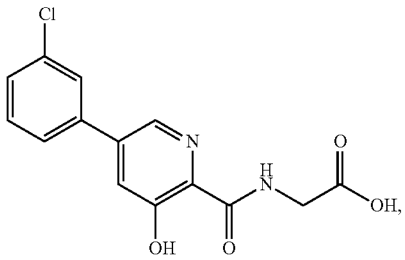

which comprises (i) a step of reacting a compound (a4) represented by formula:

[Chemical Formula 27]

a4

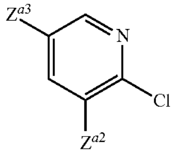

{wherein $Z^{a2}$ represents a hydroxy group or a substituent represented by formula:

[Chemical Formula 28]

(wherein $P^{a1}$ represents a protecting group for hydroxy group), $Z^{a3}$ represents a bromine atom, an iodine atom or a trifluoromethanesulfoxy group}, and a compound (a5) represented by formula:

[Chemical Formula 29]

a5

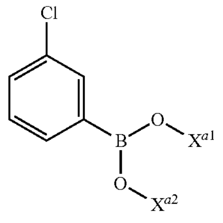

(wherein $X^{a1}$ and $X^{a2}$ each independently represents a hydrogen atom or an alkyl group, or alternatively, both of them bind to each other to form an alkylene group)

or an equivalent compound to the compound (a5), in the presence or absence of a base, in the presence or absence of a palladium catalyst, in a solvent or in the absence of a solvent to prepare a compound (a1-1-a) represented by formula:

[Chemical Formula 30]

a1-1-a

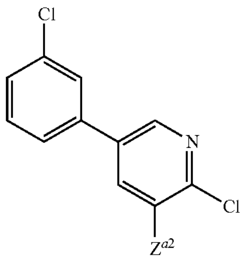

(wherein, $Z^{a2}$ is the same as defined above.):

(ii) a step of reacting the compound (a1-1-a), a compound (2-1) represented by formula:

[Chemical Formula 31]

2-1

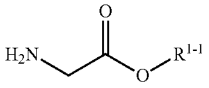

(wherein $R^{1-1}$ represents an optionally substituted alkyl group or a resin residue) or a salt of the compound (2-1), with a carbon monoxide in the presence or absence of a palladium catalyst, in the presence or absence of a ligand, in the presence or absence of a base, in a solvent or in the absence of a solvent to obtain a compound (a3-1-a) represented by formula:

[Chemical Formula 32]

a3-1-a

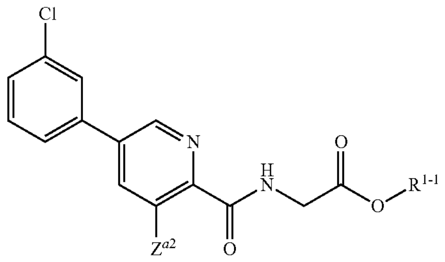

(wherein $R^{1-1}$ and $Z^{a2}$ are the same defined above.); and (iii) a step of converting the compound (a3-1-a) into the compound [I(A)] represented by formula:

[Chemical Formula 33]

I(A)

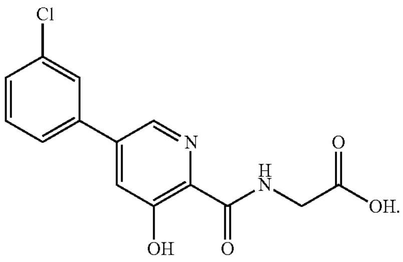

[12] The process according to [11] wherein

The compound (a4) represents a compound (a4-2) represented by formula:

[Chemical Formula 34]

a4-2

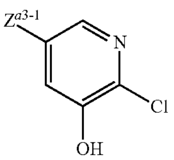

(wherein $Z^{a3}$-1 represents a bromine atom or an iodine atom), the compound (a1-1-a) represents a compound represented by formula (a1-4-a):

[Chemical Formula 35]

a1-4-a

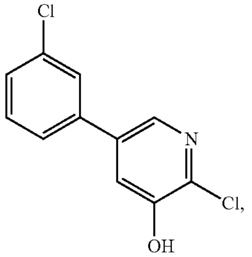

and the compound (a3-1-a) represents a compound (a3-2-a) represented by formula:

[Chemical Formula 36]

a3-2-a

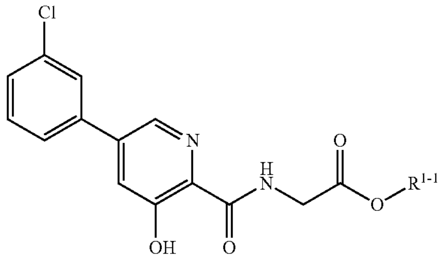

(wherein $R^{1-1}$ represents an optionally substituted alkyl group or a resin residue).

[13]A process for preparing a compound [I(A)] represented by formula:

[Chemical Formula 37]

I(A)

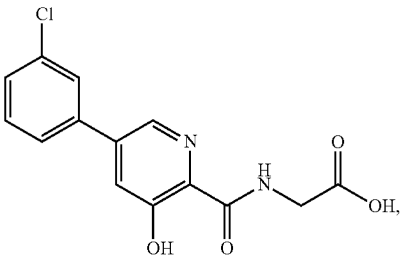

which comprises (i) a step of compound (a4-1) represented by formula:

[Chemical Formula 38]

a4-1

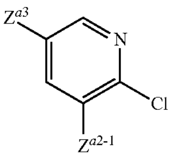

(wherein $Z^{a2}$-1 represents a substituent represented by formula:

[Chemical Formula 39]

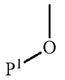

(wherein $P^1$ represents a protecting group for hydroxy group), and $Z^{a3}$ represents a bromine atom, an iodine atom, or a trifluoromethanesulfoxy group}, with a compound (a5) represented by formula:

[Chemical Formula 40]

a5

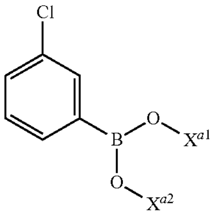

(wherein, $X^{a1}$ and $X^{a2}$ each independently represents a hydrogen atom, or an alkyl group, or alternatively both of them bind to each other to form an alkylene group), or an equivalent compound of the compound (a5), in the presence of absence of a base, in the presence of absence of a palladium catalyst, in a solvent or in the absence of a solvent, to prepare a compound (a1-3-a) represented by formula:

[Chemical Formula 41]

a1-3-a

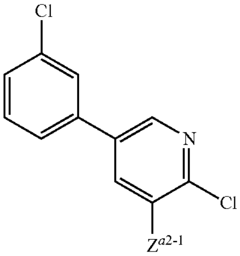

(wherein $Z^{a2}$-1 is the same as defined above.);

(ii) a step of converting the compound (a1-3-a) into the compound (a1-4-a) represented by formula:

[Chemical Formula 42]

a1-4-a

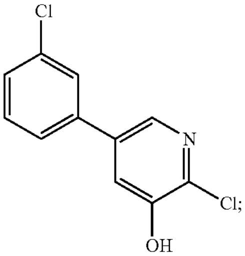

(iii) a step of reacting the compound (a1-4-a), a compound (2-1) represented by formula:

[Chemical Formula 43]

2-1

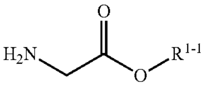

(wherein, $R^{1-1}$ represents an optionally substituted alkyl group or a resin residue), or salts of the compound (2-1), with a carbon monoxide in the presence or absence of a palladium catalyst, in the presence or absence of a ligand, in the presence or absence of a base, and in a solvent or in the absence of a solvent to prepare the compound (a3-2-a) represented by formula:

[Chemical Formula 44]

a3-2-a

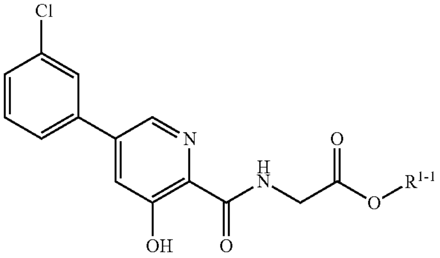

(wherein $R^{1-1}$ is the same as defined above); and (iv) a step of converting the compound (a3-2-a) into the compound [(I(A)] represented by formula:

[Chemical Formula 45]

I(A)

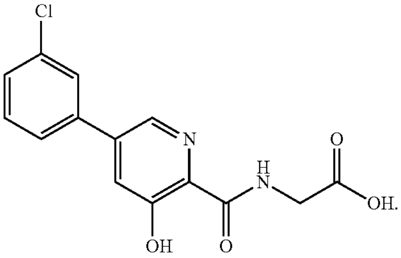

[14]A process for preparing a compound (b3-1) represented by formula:

[Chemical Formula 46]

b3-1

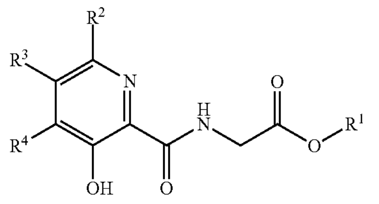

(wherein $R^1$ represents an optionally substituted alkyl group, a hydrogen atom, or a resin residue, $R^2$ represents a hydrogen atom, or an optionally substituted methyl group, $R^3$ represents a phenyl group which may be optionally substituted with halogen atom, a chlorine atom, a bromine atom, an iodine atom, or a trifluoromethanesulfoxy group, and $R^4$ represents a hydrogen atom, or alternatively, $R^3$ and $R^4$ bind to each other and combine together with a pyridine group to which they are adjacent to form an isoquinoline group which may be optionally substituted with phenyloxy group), (i) a step of reacting a compound (b1) represented by formula:

[Chemical Formula 47]

b1

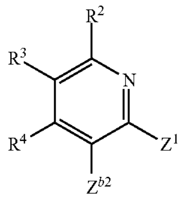

(wherein $Z^1$ represents a chlorine atom, a bromine atom, or an iodine atom, $Z^{b2}$ represents a chlorine atom, a bromine atom or an iodine atom, and $R^2$, $R^3$, and $R^4$ are the same as defined above), a compound represented by formula (2):

[Chemical Formula 48]

2

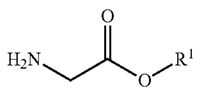

(wherein $R^1$ represents an optionally substituted alkyl group, a hydrogen atom or a resin residue), or a salt of the compound (2), with a carbon monoxide in the presence of a palladium catalyst, in the presence or absence of a ligand, in the presence of a base, in a solvent to obtain a compound (b3) represented by formula:

[Chemical Formula 49]

b3

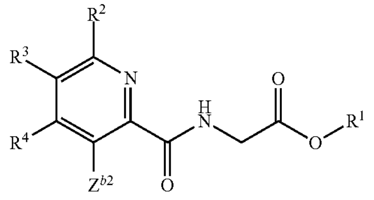

(wherein the symbols are the same as defined above); and (ii) a step of reacting the compound (b3) with the compound (b4) represented by formula;

[Chemical Formula 50]

b4

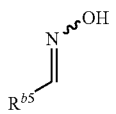

(wherein $R^{b5}$ represents an optionally substituted aryl group, or an optionally substituted alkyl group)

in the presence of a palladium catalyst, in the presence or absence of a ligand, in the presence of a base, in a solvent to prepare a compound represented by formula (b3-1):

[Chemical Formula 51]

b3-1

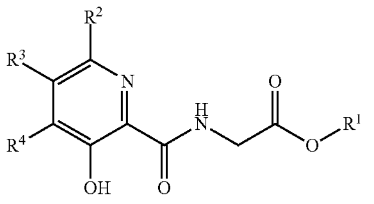

(wherein the symbols are the same as defined above).

[15] The process according to [14] wherein a pressure of carbon monoxide during a reaction is 0.01 MPa to 1 MPa.

[16] The process according to [14] or [15] wherein a molar ratio of the compound (b1) used in the reaction to the compound (2) used in the reaction is 2:1 to 1:2.

[17] The process according to any one of [14] to [16] wherein the reaction is conducted in nitriles as a solvent, and at 20° C. to 150° C. as a reaction temperature.

[18]A process which comprises conducting a reaction according to the process according to any one of [14] to

[17] to obtain a compound (b3-2-2) represented by formula:

[Chemical Formula 52]

b3-2-2

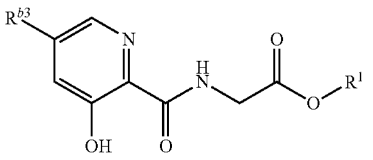

(wherein $R^1$ represents an optionally substituted alkyl group, a hydrogen atom, or a resin residue, $R^{b3}$ represents a chlorine atom, a bromine atom, an iodine atom, or a trifluoromethanesulfoxy group), and reacting the compound (b-3-2-2) with a compound (b6) represented by formula:

[Chemical Formula 53]

b6

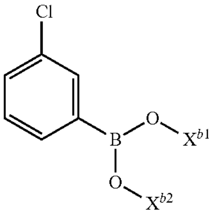

(wherein $X^{b1}$ and $X^{b2}$ each independently represents a hydrogen atom or an alkyl group, or alternatively, both of them bind to each other to form an alkylene group), or an equivalent compound of the compound (b6), in the presence or absence of a base, in the presence or absence of a palladium catalyst, in a solvent or in the absence of a solvent to obtain a compound (b3-2-a) represented by formula:

[Chemical Formula 54]

b3-2-a

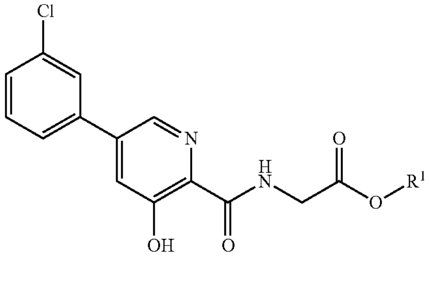

(wherein the symbols are the same as defined above).

[19]A process which comprises conducting a reaction according to the process of any one of [14] to [18] to obtain a compound (b3-1-1) represented by formula:

[Chemical Formula 55]

b3-1-1

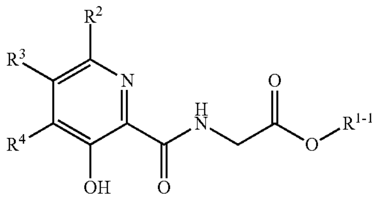

(wherein $R^{1-1}$ represents an optionally substituted alkyl group or a resin residue, $R^2$ represents a hydrogen atom or an optionally substituted methyl group, $R^3$ represents a phenyl group which may be optionally substituted with halogen atom, a chlorine atom, a bromine atom, an iodine atom, or a trifluoromethanesulfoxy group, and $R^4$ represents a hydrogen atom, or alternatively $R^3$ and $R^4$ bind to each other and combine together with a pyridine group to which they are adjacent to form an isoquinoline group which may be optionally substituted with phenyloxy group), and converting the compound (b3-1-1) into the compound (I) represented by formula:

[Chemical Formula 56]

I

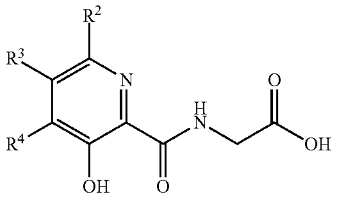

(wherein the symbols are the same as defined above).

[20] The process according to any one of [14] to [17] and [19] wherein (i) $R^2$ represents a hydrogen atom, $R^3$ represents a 3-chlorophenyl group, and $R^4$ represents a hydrogen atom, or alternatively, (ii) $R^2$ represents a methyl group, and $R^3$ and $R^4$ bind to each other and combine together with a pyridine group to which they are adjacent to form a 7-phenyloxy-isoquinoline group.

[21]A process for preparing a compound (bI-1) represented by formula:

[Chemical Formula 57]

bI-1

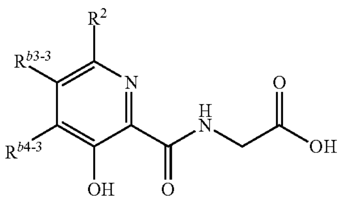

(wherein $R^2$ represents a hydrogen atom or an optionally substituted methyl group, $R^{b3-3}$ represents a 3-chlorophenyl group, a chlorine atom, a bromine atom, an iodine atom, or a trifluoromethanesulfoxy group, $R^{b4-3}$ represents a hydrogen atom, or alternatively $R^{b3-3}$ and $R^{b4-3}$ bind to each other and combine together with a pyridine group to which they are adjacent to form a 7-phenyloxy-isoquinoline group), which comprises (i) a step of reacting a compound (b1-2) represented by formula:

[Chemical Formula 58]

b1-2

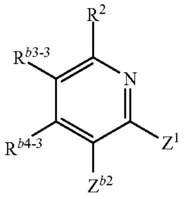

(wherein $Z^1$ represents a chlorine atom, a bromine atom, or an iodine atom, $Z^{b2}$ represents a chlorine atom, a bromine atom, or an iodine atom, and $R^2$, $R^{b3-3}$ and $R^{b4-3}$ are the same as defined above), or a compound (2-1) represented by formula:

[Chemical Formula 59]

2-1

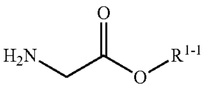

(wherein $R^{1-1}$ represents an optionally substituted alkyl group or a resin residue), or a salt of the compound (2-1), with a carbon monoxide in the presence or absence of a palladium catalyst, in the presence or absence of a ligand, in the presence or absence of a base, and in a solvent or in the absence of a solvent to obtain a compound (b3-4) represented by formula:

[Chemical Formula 60]

b3-4

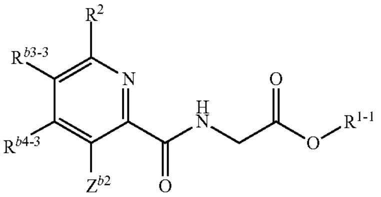

(wherein the symbols are the same as defined above), and (ii) a step of reacting the compound (b3-4) and a compound represented by formula (b4):

[Chemical Formula 61]

b4

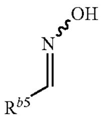

(wherein $R^{b5}$ represents an optionally substituted aryl group or an optionally substituted alkyl group)

in the presence of a palladium catalyst, in the presence or absence of a ligand, in the presence of a base, in a solvent to obtain a compound (b3-5) represented by formula:

[Chemical Formula 62]

b3-5

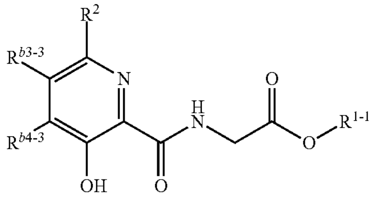

(wherein the symbols are the same as defined above); and (iii) converting the compound (b3-5) into a compound (bI-1) represented by formula:

[Chemical Formula 63]

bI-1

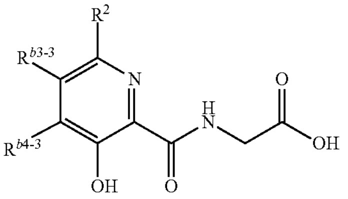

(wherein the symbols are the same as defined above).

[22]A compound (a1-a) represented by formula:

[Chemical Formula 64]

a1-a

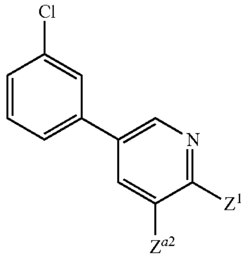

{wherein $Z^1$ represents a chlorine atom, a bromine atom, or an iodine atom, and $Z^{a2}$ represents a hydroxy group, or a substituent represented by formula:

[Chemical Formula 65]

(wherein $P^1$ represents a protecting group for hydroxy group)}.

[23]A crystal of the compound (a3-1-A) represented by formula:

[Chemical Formula 66]

a3-1-A

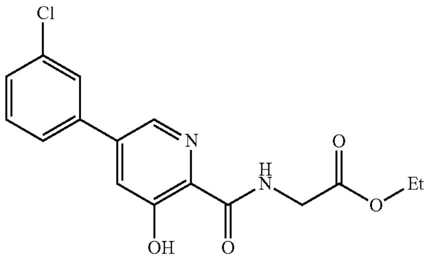

(wherein Et represents an ethyl group).

[24] The crystal according to [23] wherein the crystal of the compound (a3-1-A) is a I type crystal of the compound (a3-1-A).

[25] The crystal according to [23] wherein the crystal of the compound (a3-1-A) is a II type crystal of the compound (a3-1-A).

Effect of Invention

The process of the present invention can prepare a compound [I(A)] which is a nitrogen-containing heteroarylcarboxamide acetic acid and is useful as a medicine in more shorten steps, and may become an industrially advantageous process.

MODE FOR CARRYING OUT THE INVENTION

Figure 1:
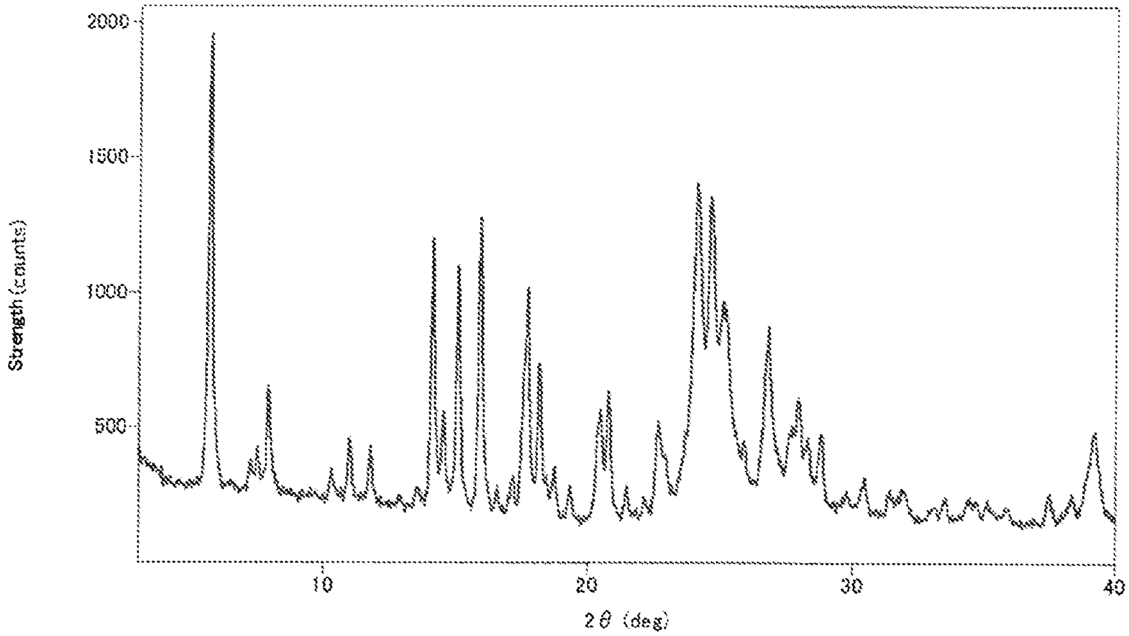
FIG. 1 shows a powder X-ray diffraction pattern of the I type crystal of the compound [I(A)] of the present invention.

The definition of each group used herein is described below.

The term of "alkyl group" represents a straight chain or branched chain of saturated hydrocarbon chain having 1 to 6 carbon atom(s). Examples of the alkyl group include a methyl group, an ethyl group, a propyl group, an isopropyl group, a butyl group, a t-butyl group, an isobutyl group, a pentyl group, a hexyl group, and various branched chain isomers thereof, and preferably a straight chain or branched chain of saturated hydrocarbon chain having 1 to 4 carbon atoms.

The term of "alkylene group" represents a straight chain or branched chain of divalent saturated hydrocarbon chain having 1 to 8 carbon atom(s). Examples of the alkylene group include a methylene group, a 1,2-ethylene group, a 1,3-propylene group, a 1,1,2,2-tetramethyl-1,2-ethylene group, and various branched chain isomers thereof.

The term of "aryl group" represents a monocyclic or bicyclic of aromatic hydrocarbon group having 6 to 11 carbon atoms as a ring-constitute carbon atom, and includes the monocyclic aromatic hydrocarbon group such as a phenyl group; and the bicyclic aromatic hydrocarbon group having 9 to 11 carbon atoms as a ring-constitute carbon atom such as a naphthyl group, a tetrahydronaphthyl group, an indenyl group, an indanyl group and an azulenyl group.

The number of the substituent(s) for the terms of "Optionally substituted aryl group" and "Optionally substituted phenyl group" may be one (1) or more (such as one(1) to three(3)), and the substituents may be identical to or different from each other. Examples of the substituent include an alkyl group, a cycloalkyl group, an alkoxy group, a cyano group, a halogen atom, a hydroxy group, and a nitro group, and preferably a halogen atom (such as a chlorine atom, a bromine atom, and an iodine atom).

The number of the substituent(s) for the terms of "Optionally substituted alkyl group" may be one (1) or more (such as one (1) to seven (7)), and the substituents may be identical to or different from each other. Examples of the substituent include a cycloalkyl group, an alkoxy group, a halogen atom, an oxo group, and a hydroxy group.

The term of "cycloalkyl group" represents a cyclic saturated hydrocarbon ring having 3 to 8 carbon atoms. Examples of the cycloalkyl group include a cyclopropyl group, a cyclobutyl group, a cyclopentyl group, a cyclohexyl group, a cycloheptyl group, a cyclooctyl group and the others. When the cycloalkyl group is referred to as herein, a fused ring and a spiro ring may be also included.

The term of "alkoxy group" represents a group wherein the alkyl group binds to an oxygen atom, and includes, for example, a methoxy group, an ethoxy group, a propoxy group, a butoxy group, a pentyloxy group, a hexyloxy group, and the others.

The term of "alkanoyl group" represents a group wherein the alkyl group binds to a carbonyl group, and includes, for example, an acetyl group, a propanoyl group, a butyryl group, a pentanoyl group, a hexanoyl group, and a heptanoyl group.

The term of "alkanoic acid" represents a compound wherein the alkyl group binds to a carboxy group, and includes, for example, an acetic acid, a propionic acid, a butanoic acid, a pentanoic acid, a hexanoic acid, a heptanoic acid, and the others.

The term of "isoquinoline group which may be optionally substituted with phenyloxy group" represents an isoquinoline group which may be optionally substituted with one (1) or more (such as one (1) to three (3)) phenyloxy group(s), and includes, for example, a 7-phenyloxy-isoquinoline group. Here the phenyloxy group may include an optionally substituted phenyloxy group, and the number of the substituent(s) may be one (1) or more (such as one (1) to three (3)), and the substituents may be identical to or different from each other. Examples of the substituent include an alkyl group, a cycloalkyl group, and an alkoxy group.

Examples of the term of "halogen" include a fluorine atom, a chlorine atom, a bromine atom, and an iodine atom.

Examples of the term of "ligand" include a phosphine ligand, as well as a nitrogen-containing heterocyclic carbene ligand, the corresponding azorium salt ligand precursors, and the others, which is not limited thereto.

Examples of the term of "phosphine ligand" may include a monodentate phosphine ligand, and a bidentate phosphine ligand, which is not limited thereto.

The term of "monodentate phosphine ligand" represents a compound wherein one (1) phosphine atom is contained in the molecule, and includes, for example, a tricyclohexylphosphine, a triphenylphosphine, a 2-di-tertbutylphosphino-3-methoxy-6-methyl-2',4',6'-triisopropyl-1,1'-biphenyl (RockPhos), a 2-di-tert-butylphosphino-3,4,5,6-tetramethyl-2',4',6'-triisopropyl-1,1'-biphenyl (Me4tBuXPhos), a 2-di-tert-butylphosphino-3,6-dimethoxy-2',4',6'-triisopropyl-1,1'-biphenyl (tBuBrettPhos), a 2-di-tert-butylphosphino-2',4',6'-triisopropyl-1,1'-biphenyl (tBuXPhos), and a 2-(di-1-adamanthylphoshino)-2',4',6'-triisopropyl-3,6-dimethoxybiphenyl (AdBrettPhos).

The term of "bidentate phosphine ligand" represents a compound wherein two (2) phosphine atoms are contained in the molecule, and includes, for example, a 1,3-bis(diphenylphosphino)propane (dppp), a 1,4-bis(diphenylphosphino)butane (dppb), a 1,5-bis(dipheylphoshino)pentane (dpppe), a 2,4-bis(diphenylphosphino)pentane (BDPP), a 1,1'-bis(diphenylphoshino)ferrocene (dppf), a 2,2'-bis(diphenylphoshino)-1,1'-binapthyl (BINAP) (rac-BINAP, (S)-BINAP, (R)-BINAP), a 2,2'-bis(di-p-tolylphoshino)-1,1'-binapthyl (tolBINAP) (rac-tolBINAP, (S)-tolBINAP, (R)-tolBINAP), and a 4,5-bis(diphenylphoshino)-9,9-dimethyl Xanthene (Xantphos).

The term of "nitrogen-containing heterocyclic carbene ligand" represents a ligand wherein a nitrogen-containing monocyclic five membered ring backbone having 2 to 4 nitrogen atoms as a ring-constitute atom, and the carbon atom carbene composed of the five membered ring is sandwiched between two ring-constitute nitrogen atoms, and include, for example, a 1,3-bis(2,6-diisopropylphenyl)imidazol-2-ylidene, a 1,3-bis(2,4,5-trimethylphanyl)imidazol-2-ylidene, and a 1,3-bis(2.6-bis(diphenylmethyl)-4-methylphenyl]-2-imidazolilidene.

Examples of the term of "azorium salt ligand precursor" include an imidazolium salt ligand precursor, a thiazolium salt ligand precursor, and a triazolium ligand precursor, and preferably an imidazolium salt ligand precursor.

The term of "resin residue" represents a resin used in a solid phase peptide synthesis, and includes, for example, a trityl resin (such as 2-chlorotrityl resin), a Merrifield resin (such as 4-chloromethyl polystyrene resin), a Wang resin (such as 4-benzyloxy benzyl alcohol resin), a hydroxy methyl polystyrene resin (such as 4-hydroxymethyl polystyrene resin), an aminomethyl polystyrene resin (such as 4-aminomethyl polystyrene resin), and a thiol resin.

The process for preparing a compound (I) of the present invention is specifically described below.

Reaction Scheme (I-I)

[Chemical Formula 67]

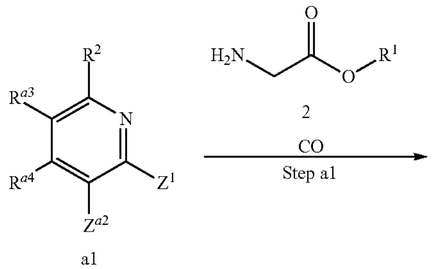

a1

-continued

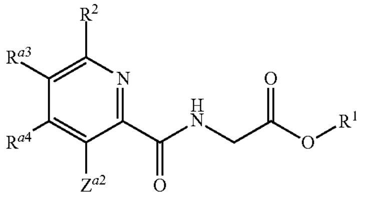

a3

Reaction Scheme (I-I-I)

[Chemical Formula 68]

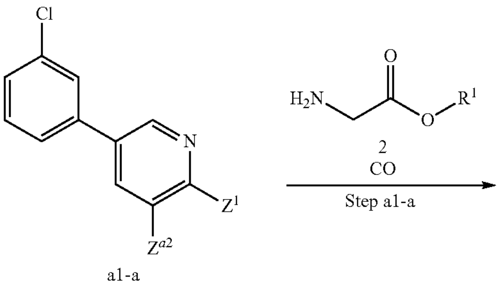

a1-a

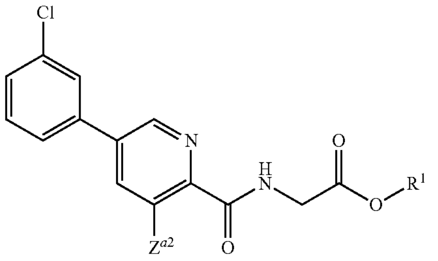

a3-a

Reaction Scheme (I-I-II)

[Chemical Formula 69]

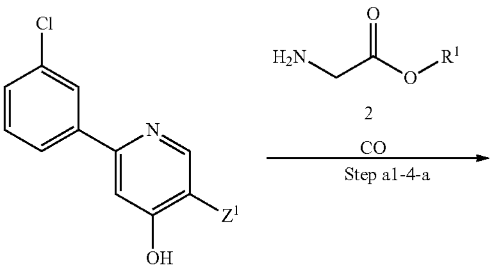

a1-5-a

-continued
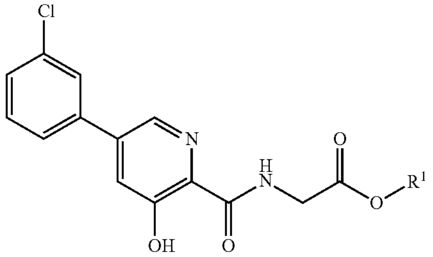
a3-3-a
Reaction Scheme (I-II)
[Chemical Formula 70]
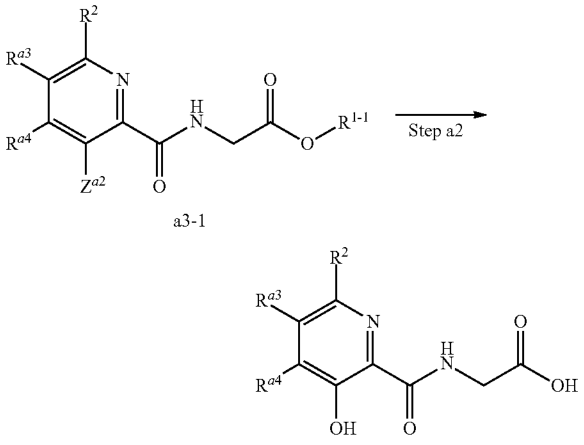
a3-1
aI
Reaction Scheme (I-II-I)
[Chemical Formula 71]
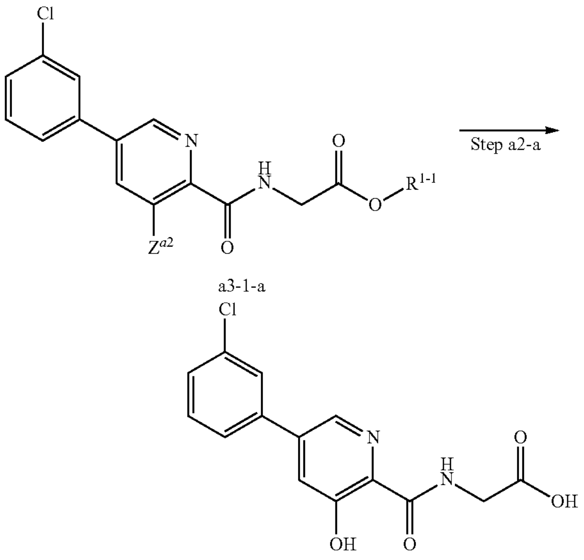
a3-1-a
I(A)
Reaction Scheme (I-II-II)
[Chemical Formula 72]
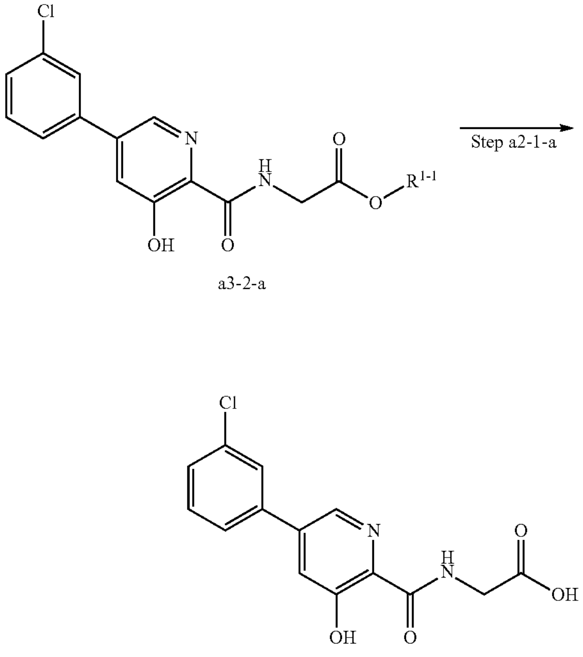
a3-2-a
I(A)
Reaction Scheme (I-III)
[Chemical Formula 73]
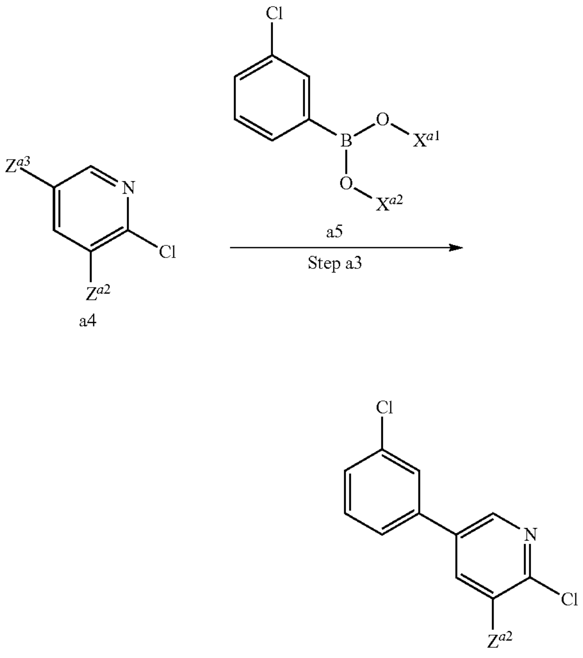
a4
a5
a1-1-a Reaction Scheme (I-III-I)
[Chemical Formula 74]
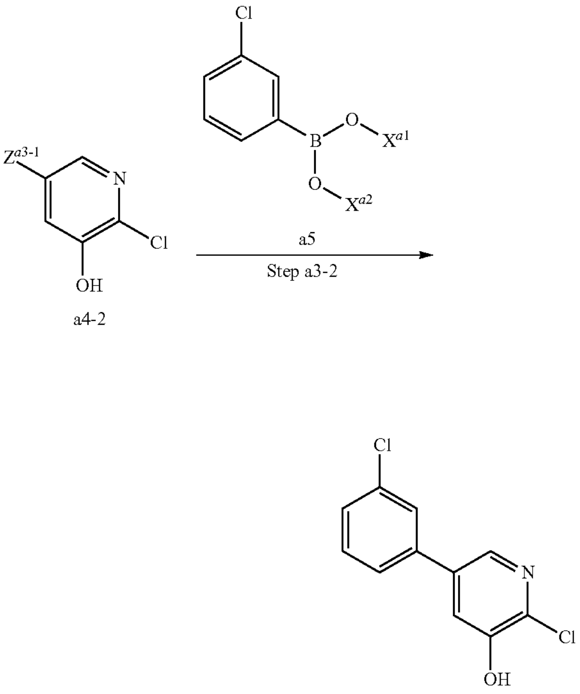
a1-4-a
Reaction Scheme (I-IV)
[Chemical Formula 75]
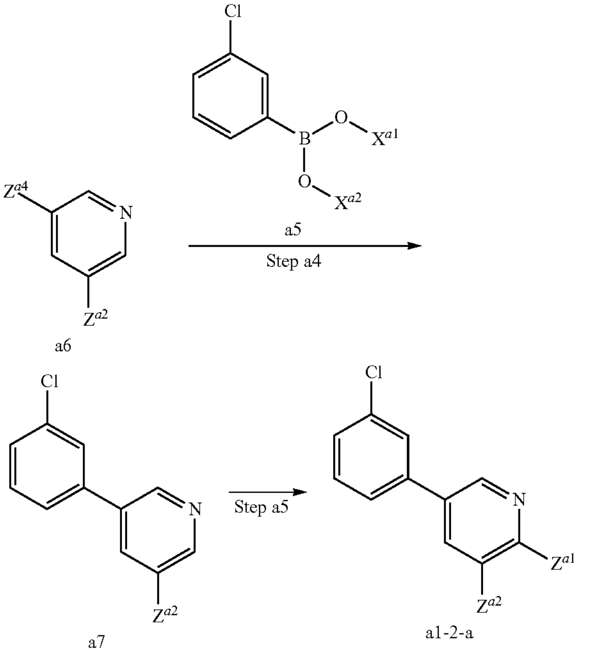
a7 a1-2-a
Reaction Scheme (I-V)
[Chemical Formula 76]
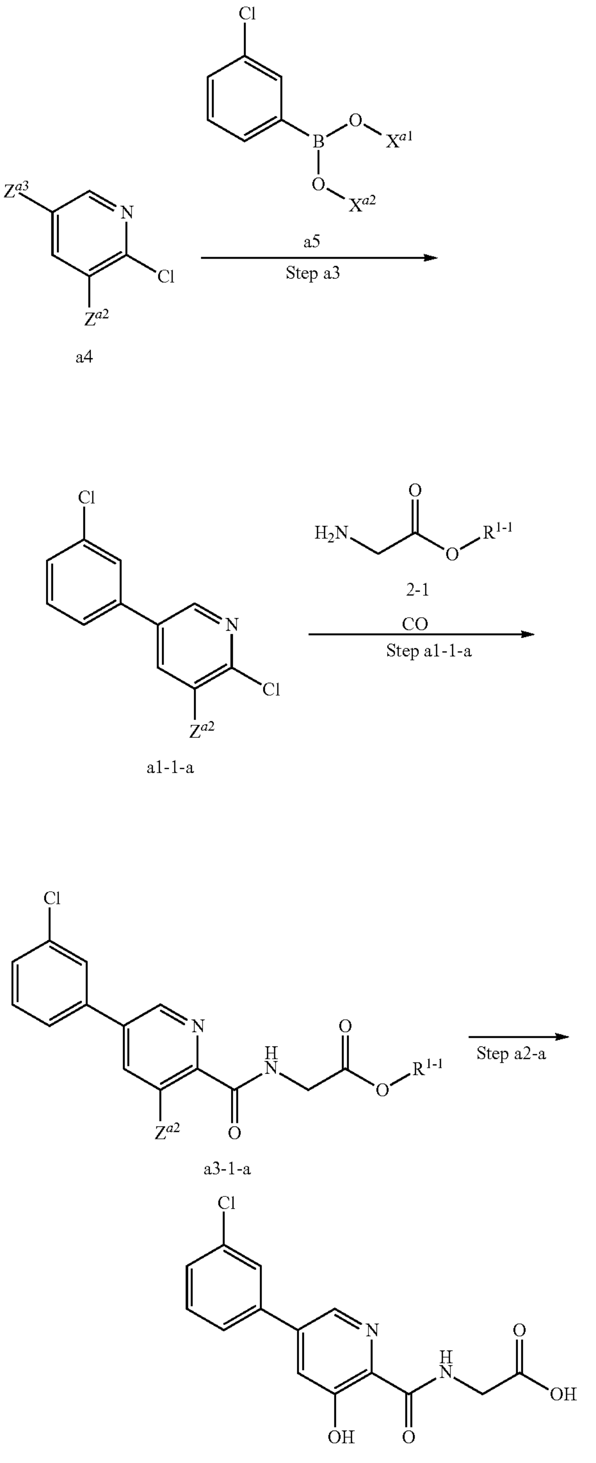
I(A)

Reaction Scheme (I-V-I)
[Chemical Formula 77]
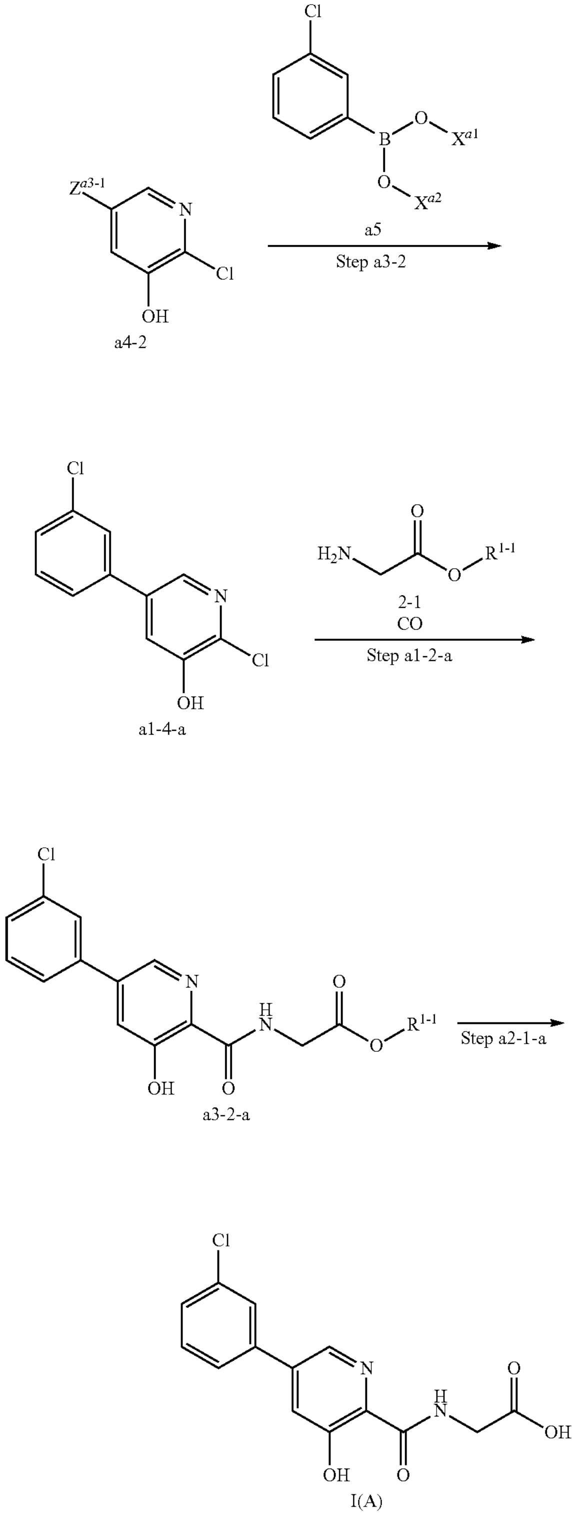
Reaction Scheme (I-VI)
[Chemical Formula 78]
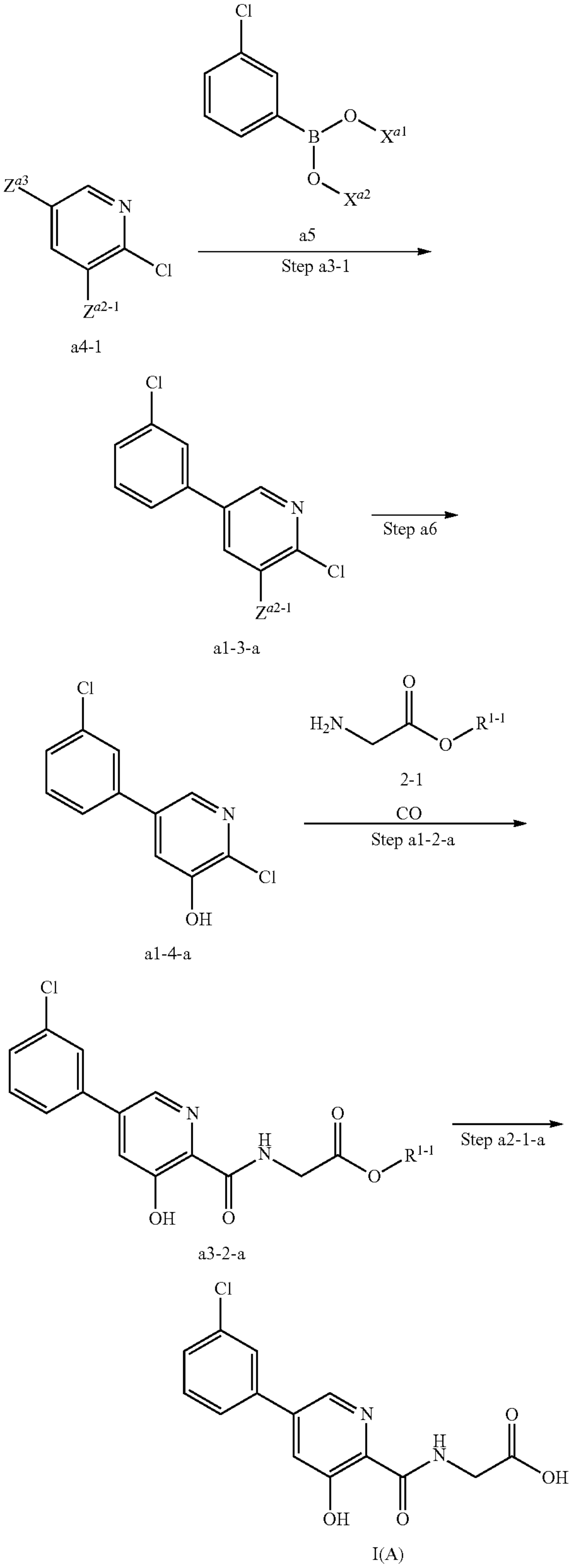

Reaction Scheme (I-VII)

[Chemical Formula 79]

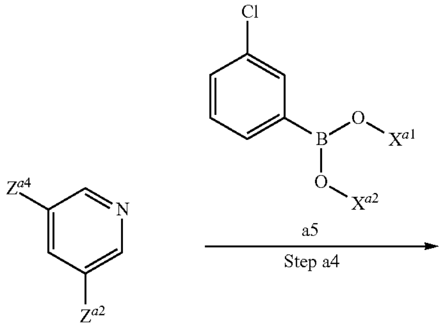

a6

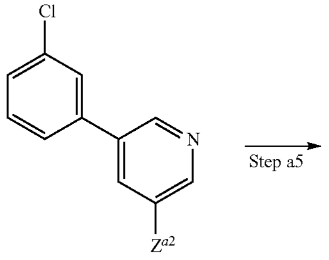

a7

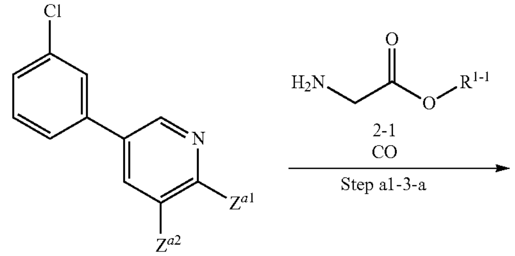

a1-2-a

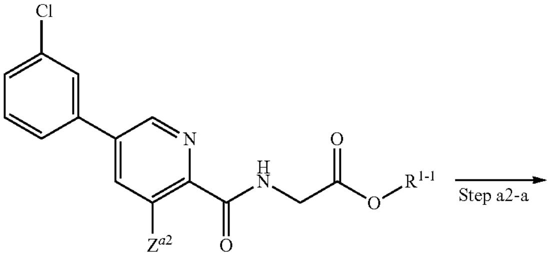

a3-1-a

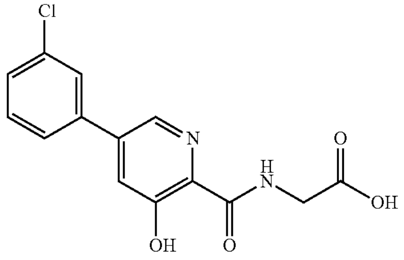

I(A)

(in the above Reaction Schemes (I-I) to (I-VII), $R^1$ represents an optionally substituted alkyl group, a hydrogen atom, or a resin residue, preferably an optionally substituted alkyl group, and more preferably an alkyl group. $R^{1-1}$ represents an optionally substituted alkyl group or a resin residue, preferably an optionally substituted alkyl group, and more preferably an alkyl group.

$R^2$ represents a hydrogen atom, or an optionally substituted methyl group.

$R^{a3}$ represents a phenyl group which may be optionally substituted with halogen atom, and $R^{a4}$ represents a hydrogen atom, or alternatively, $R^{a3}$ and $R^{a4}$ bind to each other and combine together with a pyridine group to which they are adjacent to form an isoquinoline group which may be optionally substituted with phenyloxy group.

$Z^1$ represents a chlorine atom, a bromine atom, or an iodine atom, and preferably a chlorine atom. $Z^{a1}$ represents a chlorine atom, a bromine atom, or an iodine atom, and preferably a chlorine atom or an iodine atom.

$Z^{a2}$ represents a hydroxy group or a substituent represented by formula:

[Chemical Formula 80]

(wherein $P^1$ represents a protecting group for hydroxy group), and preferably a hydroxy group.

$Z^{a2-1}$ represents a substituent represented by formula;

[Chemical Formula 81]

(wherein $P^1$ represents a protecting group for hydroxy group).

$Z^{a3}$ represents a bromine atom, an iodine atom, or a trifluoromethanesulfoxy group, and preferably a bromine atom.

$Z^{a4}$ represents a chlorine atom, a bromine atom, an iodine atom or a trifluoromethanesulfoxy group, and preferably a bromine atom.

$X^{a1}$ and $X^{a2}$ each independently represents a hydrogen atom or an alkyl group, or alternatively, both of them bind to each other to form an alkylene group, and preferably, each represents a hydrogen atom.

Here examples of the substituent for the optionally substituted methyl group expressed as $R^2$ is not particularly limited as long as it is any substituent that can be converted into an unsubstituted methyl group. Examples of the optionally substituted methyl group include a methyl group which may be optionally substituted with dialkylamino group or alkanoyloxy group.

Examples of the phenyl group which may be optionally substituted with halogen atom expressed by $R^{a3}$ include preferably a 3-chlorophenyl group.

Examples of $R^2$, $R^{a3}$ and $R^{a4}$ include preferably (i) $R^2$ represents a hydrogen atom, and $R^{a3}$ represents a 3-chlorophenyl group, and $R^{a4}$ represents a hydrogen atom, or alternatively, (ii) $R^2$ represents a methyl group, and $R^{a3}$ and $R^{a4}$ binds to each other and combine together with a pyridine group to which they are adjacent to form a 7-phenyloxy-isoquinolinone group, more preferably, (i) $R^2$ represents a hydrogen atom, $R^{a3}$ represents a 3-chlorophenyl group, and $R^{a4}$ represents a hydrogen atom.

A protecting group for hydroxy group expressed by $P^1$ is not particularly limited, and preferably include a methyl group which may be optionally substituted with phenyl group which may be optionally, substituted with one or two methoxy group(s) (such as a methyl, a benzyl, or a p-methoxybenzyl); an alkoxymethyl group which may be optionally substituted with trialkyl silyl group (such as a methoxy methyl, a triethylsilyl ethoxy methyl); an alkanoyl group (such as an acetyl or a pivaloyl); a sulfonyl group which may be optionally substituted with an optionally substituted methyl group or an optionally substituted phenyl group (such as a methanesulfonyl, a benzenesulfonyl, a p-toluenesulfonyl, a o-nitrobenzenesulfonyl); an optionally substituted alkyloxy carbonyl group (such as a t-butyloxy-carbonyl, a benzyloxycarbonyl); a silyl group which is substituted with three groups selected from an alkyl group and an optionally substituted phenyl group (such as a triethyl silyl, a triisopropyl silyl, a tert-butyldimethyl silyl, a tert-butyldiphenyl silyl); and an aminocarbonyl group which is substituted with an optionally substituted alkyl group and an optionally substituted phenyl group (such as a dimethylaminocarbonyl, a methylphenylaminocarbonyl). More preferably, examples of the above protecting group include a methyl group which is substituted with phenyl which may be optionally substituted with one (1) or two (2) methoxy group(s) (such as a benzyl, a p-methoxybenzyl); an alkanoyl group (such as a pivaloyl); and a sulfonyl group which is substituted with optionally substituted methyl group or optionally substituted phenyl group (such as a methanesulfonyl, a benzenesulfonyl, a p-toluenesulfonyl, a o-nitrobenzesulfonyl).

Step a1, Step a1-a, Step a1-1-a, Step a1-2-a, Step a1-3-a, and Step a1-4-a

The compound (a1), the compound (a1-a), the compound (a1-1-a), the compound (a1-2-a), the compound (a1-4-a), or the compound (a1-5-a) (hereinafter, these compounds may be collectively referred to as "compound (a1) etc."), the compound (2) or the compound (2-1) (hereinafter, these compounds may be collectively referred to as "compound (2) etc."), or salts thereof, are reacted with a carbon monoxide in the presence of a palladium catalyst (here, it is referred to as "palladium catalyst (1)") and in the presence of a base, in the presence or absence of a ligand, in a solvent to prepare the compound (a3), the compound (a3-a), the compound (a3-1-a), or the compound (a3-2-a) (hereinafter, these compounds may be collectively referred to as "compound (a3) etc.").

When the compound (2) etc. wherein $R^1$ represents a resin residue, or salts thereof are used in the present reaction, the resin residue represents a resin which is used in a solid phase peptide synthesis, and includes, for example, trityl resin (such as a 2-chlorotrityl resin), a Merrifield resin (such as a 4-chloromethyl polystyrene resin), a Wang resin (such as a 4-benzyloxy benzyl alcohol resin), a hydroxymethyl polystyrene resin (such as a 4-hydroxymethyl polystyrene resin), an aminomethyl polystyrene resin (such as a 4-aminomethyl polystyrene resin), and a thiol resin. The particle size and the loading capacity (mole number at reaction point per 1 g resin: mmol/g) is not particularly limited as long as they does not affect any adverse effects on the reaction. In general, the particle size is preferably 35 to 500 μm, and the loading capacity is preferably 0.1 to 4 mmol/g.

Among the compound (2) etc. and salts thereof, examples of the salts of the compound (2) etc. are not particularly limited, and include, for example, a hydrochloride salt, a sulphate salt, a p-toluenesulfonate salt, a sodium salt, and a potassium salt, and preferably a hydrochloride salt. Examples of the compound (2) etc., or salts thereof include preferably salts of the compound (2) etc. The equivalent amount of the compound (2) etc., or salts thereof used in the present reaction may be varied depending on the used reagent or the reaction condition, and they are usually appropriately 1 mole equivalent amount relative to the compound (a1) etc., which is, for example, 0.5 to 2.0 mole equivalent amounts, preferably 0.8 to 1.25 mole equivalents amounts, and more preferably 1 to 1.1 mole equivalent amount(s).

Examples of the carbon monoxide include carbon monoxide gas. The carbon monoxide gas may be used singly, or may be used in admixture with inert gas (such as nitrogen gas or argon gas). When the carbon monoxide gas is used in the present reaction, the pressure of the carbon monoxide gas during the reaction may be varied depending on the used reagent or the reaction condition, it is usually 0.01 to 1 MPa, preferably 0.02 to 0.8 MPa, and more preferably 0.05 to 0.6 MPa. Here the pressure of the carbon monoxide during the reaction as used herein represents a partial pressure in the case of a reaction system where it is used in admixture with an inert gas, and/or the case of a reaction system where the reaction solvent is made a gas state under a high temperature condition.

The palladium catalyst (1) can be used in the presence or absence of a ligand in the present reaction. The palladium catalyst (1) is not particularly limited as long as it is a general palladium catalyst, and include, for example, tetrakis (triphenylphosphine)palladium (0), palladium (II) acetate, bis(acetonitrile) dichloropalladium (II), dichlorobis (triphenylphosphine)palladium (II), dichloro[1,3-bis(diphenylphosphino)propane]palladium (II), [1,1'-bis(diphenylphosphino)ferrocene]dichloropalladium (II), dichloro(4,5-bis(diphenylphosphino)-9,9-dimethylxanthene)palladium (II), (4,5-bis(diphenylphosphino)-9,9-dimethylxanthene) [2-(2'-amino-1,1'-biphenyl)]palladium (II) methanesulfonate (Xantphos Pd G3), tris(dibenzylideneacetone)dipalladium (0), and palladium (II) chloride. The ligand is not particularly limited as long as it is a general ligand, and include, for example, a bidentate phosphine ligand and a monodentate phosphine ligand.

When the palladium catalyst (1) is used in the presence or absence of a ligand in the present reaction, preferably a palladium catalyst having one or more bidentate phosphine ligand(s), which is selected from dichloro[1,3-bis(diphenylphosphino)propane]palladium (II) and [1,1'-bis(diphenylphosphino)ferrocene]dichloropalladium (II) can be used in the absence of any ligand, or alternatively a palladium catalyst not having any ligand, which is selected from palladium (II) acetate, bis(acetonitrile)dichloropalladium (II), tris(dibenzylideneacetone)dipalladium (0), and palladium (II) chloride can be used in the presence of one or more bidentate phosphine ligand(s); and more preferably, a palladium catalyst not having any phosphine ligand, which is selected from palladium (II) acetate, bis(acetonitrile)dichloropalladium (II), tris(dibenzylideneacetone)dipalladium (0), and palladium (II) chloride can be used in the presence of one or more bidentate phosphine ligand(s); and more preferably, palladium (II) acetate can be used in the presence of one or more bidentate phosphine ligand(s).

Examples of the bidentate phosphine ligand include 1,3-bis(diphenylphosphino)propane (dppp), 1,4-bis(diphenylphosphino)butane (dppb), 1,5-bis(diphenylphosphino)pentane (dpppe), 2,4-bis(diphenylphosphino)pentane (BDPP), 1,1'-bis(diphenylphosphino)ferrocene (dppf), 2,2'-bis(diphenylphosphino)-1,1'-binapthyl (BINAP) (rac-BINAP, (S)-BINAP, (R)-BINAP), 2,2'-bis(di-p-tolylphosphino)-1,1'-binapthyl (tolBINAP) (rac-tolBINAP, (S)-tolBINAP, (R)-tolBINAP), and 4,5-bis(diphenylphosphino)-9,9-dimethylxanthene (Xantphos), and include preferably dppp, dppb, and dppf, more preferably dppp, and further preferably dppb. The equivalent amount of the palladium catalyst (1) used in the present reaction may be varied depending on the used reagent or the reaction condition, a catalytic amount of the compound (a1) etc. is usually preferred, which is for example, 0.001 to 0.1 mole equivalent amounts, and preferably 0.01 to 0.05 mole equivalent amounts, relative to the compound (a1) etc. When the reaction is carried out in the presence of a ligand, the equivalent amounts of the ligand may be varied depending on the used reagent or the reaction condition, and is usually 1 to 5 mole equivalent amount(s), and preferably 1.5 to 3 mole equivalent amounts, relative to the palladium catalyst (1).

The base is not particularly limited as long as it is a general base, and includes, for example, a trialkyl amine (such as triethylamine, N,N-diisopropylethylamine, tripropylamine, tributylamine), a cyclic tertiary amines (such as 4-methylmorpholine, 1,4-diazabicyclo[2.2.2]octane triethylenediamine (DABCO), 4-dimethylaminopyridine (DMAP)), a dialkylamine (such as diisopropylamine, dibutylamine, tert-butylethylamine), an alkali metal alkanoate (such as alkali metal acetate (such as sodium acetate, potassium acetate, cesium acetate, etc.), sodium propionate, sodium butanoate, sodium valerate), an optionally substituted phenylcalboxylic acid alkali metal (such as sodium salicylate, disodium terephthalate), an alkali metal carbonate (such as sodium carbonate, potassium carbonate, cesium carbonate, sodium hydrogen carbonate, potassium hydrogen carbonate), and an alkali metal phosphate (such as trisodium phosphate, tripotassium phosphate). A trialkylamine, alkali metal alkanoate, and an optionally substituted phenyl carboxylic acid alkali metal are preferably included, and trialkylamine is more preferably included. Examples of the trialkylamine include preferably triethylamine, tripropylamine, and tributylamine, and more preferably tripropylamine. The equivalent amount of a base used in the present reaction may be varied depending on the used reagent and the reaction condition, and is usually 1 to 10 mole equivalent amount(s), and preferably 2 to 5 mole equivalent amounts, relative to the compound (a1) etc.

The solvent is not particularly limited as long as it is a reaction-inactive solvent, and includes, for example, nitriles (such as acetonitrile, propionitrile, benzonitrile), esters (such as ethyl acetate, isopropyl acetate), aromatic hydrocarbons (such as toluene, xylene), aprotic polar solvents (such as N,N-dimethylformamide, N,N-dimethylacetamide, N-methylpyrrolidone), sulfoxides (such as dimethyl sulfoxides), ethers (such as 1,2-dimethoxyethane, 1,2-diethoxyethane, 1,3-dimethoxypropane, diglyme, cyclopentylmethyl ether, 1,4-dioxane, tetrahydrofuran, 2-methyltetrahydrofuran, diphenyl ether). Nitriles and ethers are preferably included, and nitriles is more preferably included. When nitriles are used, a production ratio of the desired compound (a3) etc. relative to the byproducts are increased. Examples of nitriles include preferably acetonitrile. Examples of ethers include preferably tetrahydrofuran.

The reaction temperature of the present reaction may be varied depending on the used reagent or the reaction condition, and it is usually under heating. The reaction temperature is preferably 20° C. to 150° C., more preferably 40° C. to 130° C., and further preferably 105° C. to 115° C.

The reaction time of the present reaction may be varied depending on the used reagent or the reaction condition, and is usually the time until the compound (a1) etc. or the compound (2) etc. has been disappeared from the reaction mixture. The reaction time is preferably 1 hour to 72 hours, more preferably 1 hour to 48 hours, and further preferably 18 hours to 48 hours.

Step a2, Step a2-a, and Step a2-1-a

The compound (a3-1), the compound (a3-1-a) or the compound (a3-2-a) (hereinafter, these compounds may be collectively referred to as "compound (a3-1) etc.") is subjected to a deprotection, reaction according to the process described in the Patent Literature 1 or the Patent Literature 2, to prepare the compound (a1) or the compound [I(A)] (hereinafter, these compounds may be collectively referred to as "compound (a1) etc.").

As the deprotection reaction of the $R^{1-1}$, commonly-used reactions can be applied depending on the $R^{1-1}$ of the used compound to conduct a deprotection reaction. For example, the compound (a3-1) etc. can be used in the presence of a base in a solvent to prepare the compound (a1) etc. The base is not particularly limited, and includes, for example, alkali metal hydroxides (such as sodium hydroxide, potassium hydroxide), alkali metal acetates (such as sodium acetate, potassium acetate, cesium acetate), and alkali metal carbonates (such as sodium carbonate, potassium carbonate, cesium carbonate, sodium hydrogen carbonate, potassium hydrogen carbonate). The base is preferably alkali metal hydroxides and alkali metal carbonates, and more preferably alkali metal hydroxides. Examples of the alkali metal hydroxides include preferably sodium hydroxide. Examples of the alkali metal carbonates include preferably potassium carbonate.

When $R^{1-1}$ represents a tert-butyl group, the compound (a3-1) etc. can be subjected to the reaction in the presence of an acid in a solvent to prepare the compound (a1) etc. The acid is not particularly limited, and includes, for example, sulfonic acids (such as methanesulfonic acid, p-toluenesulfonic acid), carboxylic acid (such as trifluoroacetic acid), and hydrogen chloride.

As the deprotection reaction of $P^1$, commonly-used method can be applied depending on the $P^1$ of the used compound to conduct the deprotection reaction. Examples of the deprotection reaction include a treatment with acid (such as a treatment with hydrochloric acid), a treatment with base (such as a treatment with aqueous sodium hydroxide solution), and a hydrogenation (such as a method using a palladium catalyst under hydrogen molecule atmosphere).

Step a3, Step a3-1, and Step a3-2

The compound (a4), the compound (a4-1), or the compound (a4-2) (hereinafter, these compounds may be collectively referred to as "compound (a4) etc.") and the compound (a5) or an equivalent compound of the compound (a5) can be reacted in the presence of a palladium catalyst (here the palladium catalyst is referred to as "palladium catalyst (2)$^{1}$"") in the presence or absence of a ligand, in the presence of a base in a solvent to prepare the compound (a1-1-a) or the compound (a1-3-a) (hereinafter, these compounds may be collectively referred to as "compound (a1-1-a) etc.").

The equivalent amount of the compound (a5) used in the present reaction may be varied depending on the used reagent or the reaction condition, and is usually 1 mole equivalent amount to small excess amounts, relative to the compound (a4) etc., which is for example, 1 to 1.5 mole equivalent amount(s), and preferably 1 to 1.1 mole equivalent amount (s)

The equivalent compound of the compound (a5) used in the present reaction includes the boroxine compound which is a compound represented by formula:

[Chemical Formula 82]

a5-a

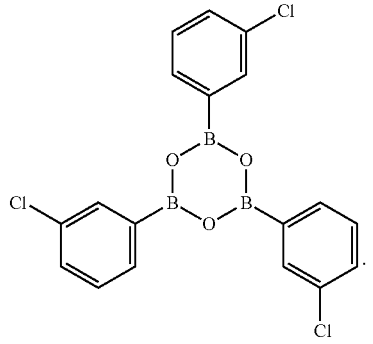

The equivalent amounts of the compound (a5-a) used in the present reaction may be varied depending on the used reagent or the reaction condition, and is usually 0.3 to 0.5 mole equivalent amounts, and preferably 0.3 to 0.4 mole equivalent amounts, relative to the Compound (a4).

The palladium catalyst (2) can be used in the presence or absence of a ligand in the present reaction. The palladium catalyst (2) is not particularly limited as long as it is a general palladium catalyst, and includes, for example, [1,1'-bis(diphenylphosphino)ferrocene]dichloropalladium (II), tetrakis (triphenylphosphine)palladium (0), palladium (II) acetate, bis(acetonitrile))dichloropalladium (II), dichlorobis (triphenylphosphine)palladium (II), dichloro[1,3-bis(diphenylphosphino)propane]palladium (II), tris(dibenzylideneacetone) dipalladium (0), palladium (II) chloride, a nitrogen-containing heterocyclic carbene-palladium complex catalyst (NHC—Pd complex catalyst), and Buchwald catalyst precursor. Examples of NHC—Pd complex catalyst includes allylchloro[1,3-bis(2,6-diisopropylphenyl)imidazol-2-ylidene]palladium (II) (CX21), allylchloro[1,3-bis(2,4,5-trimethylphenyl)imidazol-2-ylidene]palladium (II) (CX22), chlorophenylallyl[1,3-bis(2,6-diisopropylphenyl)imidazol-2-ylidene]palladium (II) (CX31), chlorophenylallyl[1,3-bis (2,6-diisopropylphenyl)-2-imidazolidene]palladium (II) (CX32), chlorophenylallyl{1,3-bis[2,6-bis(diphenylmethyl)-4-methylphenyl]-2-imidazolidene}palladium (II) (CX33), and is more preferably CX33. Examples of the Buchwald catalyst precursor includes preferably a 3rd Generation Buchwald catalyst precursor (Buchwald 3rd Generation Palladacycles), and includes, for example, (2-dicyclohexylphosphino-2',4',6'-triisopropyl-1,1'-biphenyl) [2-(2'-amino-1,1'-biphenyl)]palladium (II) methanesulfonate (XPhos Pd G3), (2-dicyclohexylphosphino-2',6'-dimethoxy-1,1'-biphenyl) [2-(2'-amino1,1'-biphenyl)]palladium (II) methanesulfonate (SPhos Pd G3), (2-dicyclohexylphosphino-2',6'-diisopropoxy-1,1'-biphenyl) [2-(2'-amino-1,1'-biphenyl)]palladium (II) methanesulfonate (RuPhos Pd G3).

The ligand is not particularly limited as long as it is a general ligand, and include, for example, a phosphine ligand, and a nitrogen-containing heterocyclic carbene ligand, or the corresponding azorium salt ligand precursors. Specific examples of these ligands include 1,1'-bis(diphenylphosphino)ferrocene (dppf), triphenylphosphine, 1,3-bis (diphenylphosphino)propane (dppp), tri-tert-butylphosphine, 2-di-tert-butylphosphino-3-methoxy-6-methyl-2',4',6'-triisopropyl-1,1'-biphenyl (RockPhos), 2-di-tert-butylphosphino-3,4,5,6-tetramethyl-2',4',6'-triisopropyl-1,1'-biphenyl (Me4tBuXPhos), 2-di-tert-butylphosphino-3,6-dimethoxy-2',4',6'-triisopropyl-1,1'-biphenyl (tBuBrettPhos), 2-di-tert-butylphosphino-2',4',6'-triisopropyl-1,1'-biphenyl (tBuXPhos), 2-(di-1-adamanthylphosphino)-2',4',6'-triisopropyl-3,6-dimethoxybiphenyl (AdBrettPhos), 2-dicyclohexylphosphino-2',4',6'-triisopropyl-1,1'-biphenyl (XPhos), 2-dicyclohexylphosphino-2',6'-dimethoxy-1,1'-biphenyl (SPhos), 2-dicyclohexylphosphino-2',6'-diisopropoxy-1,1'-biphenyl (RuPhos), 1,3-bis(2,6-diisopropylphenyl)imidazol-2-ylidene, 1,3-bis(2,4,5-trimethyl phenyl)imidazol-2-ylidene, and 1,3-bis[2,6-bis(diphenylmethyl)-4-methylphenyl]-2-imidazolidene, and the others.

When the palladium catalyst (2) is used in the presence of absence of a ligand in the present reaction, preferably [1,1'-bis(diphenylphosphino)ferrocene]dichloropalladium (II) can be used in the absence of a ligand, or alternatively, a palladium catalyst selected from palladium (II) acetate, bis(acetonitrile)dichloropalladium (II), tris(dibenzylideneacetone) dipalladium (0) and palladium (II) chloride can be used in the presence of 1,1'-bis(diphenylphosphino)ferrocene (dppf), and more preferably [1,1'-bis(diphenylphosphino)ferrocene]dichloropalladium (II) can be used in the absence of a ligand.

The equivalent amount of the palladium catalyst (2) used in the present reaction may be varied depending on the used reagent or the reaction condition, and usually a catalytic amount of the compound (a4) etc. is preferably included, which is for example, 0.001 to 0.1 mole equivalent amounts, preferably 0.002 to 0.05 mole equivalent amounts, relative to the compound (a4) etc. When the reaction is conducted in the presence of a ligand, the equivalent amount of the ligand may be varied depending on the used reagent and the reaction condition, and it is usually 1 to 5 mole equivalent amount(s) and preferably 1 to 2 mole equivalent amount(s) or 2 to 3 mole equivalent amounts, relative to the palladium catalyst (2).

The base is not particularly limited as long as it is a general base, and includes, for example, a trialkylamine (such as tripropylamine, N,N-diisopropylether amine, tripropylamine, N,N-diisopropylethylamine, tripropylamine, tributylamine), an alkali metal acetate (such as sodium acetate, potassium acetate, cesium acetate), an alkali metal carbonate (such as sodium carbonate, potassium carbonate, cesium carbonate, sodium hydrogen carbonate, potassium hydrogen carbonate), and an alkali metal phosphate (such as trisodium phosphate, tripotassium phosphate). An alkali metal carbonate is preferably included. The alkali metal carbonate includes preferably potassium carbonate. The equivalent amount of the base used in the present invention may be varied depending on the used reagent or the reaction condition, and is usually 1 to 10 mole equivalent amount(s), and preferably 2 to 5 mole equivalent amounts, relative to the compound (a4) etc.

The solvent is not particularly limited as long as it is not a reaction-inactive solvent, and includes, for example, aromatic hydrocarbons (such as toluene, xylene), esters (such as ethyl acetate, butyl acetate, isopropyl acetate), aprotic polar solvents (such as N,N-dimethyl formamide, N,N-dimethyl acetamide, N-methyl pyrrolidone), sulfoxides (such as dimethyl sulfoxides), alkyl alcohols (such as methanol, ethanol, isopropyl alcohol, t-butyl alcohol), ethers (such as 1,4-dioxane, tetrahydrofuran, 1,2-dimethoxyethane), ketones (such as methyl ketone), nitriles (such as acetonitrile, benzonitrile), and water, or mixed solvent of two or more of these solvents. The mixed solvent of water and other solvent(s) (the solvent is one or more solvent(s) selected from esters, aprotic polar solvents, sulfoxides, alkyl alcohols, ethers, ketones, and nitriles) is preferably included, and mixed solvents of water and ethers (preferably, tetrahydrofuran) or mixed solvents of water and aprotic polar solvent (preferably, N,N-dimethyl formamide) is more preferably included, and mixed solvents of water and ethers (preferably, tetrahydrofuran) is further preferably included. When the present reaction is conducted in a mixed solvent of water and the other solvent(s), the mixing ratio of each solvent (the ratio of water:the other solvent(s)) is usually a ratio of 10:1 to 1:30. When the present reaction is conducted in the mixed solvent of water and ethers, the ratio of water:ethers is preferably a ratio of 2:1 to 1:10, and more preferably a ratio of 1:1 to 1:4. When the present reaction is conducted in the mixed solvent of water and aprotic polar solvent, the ratio of water:the aprotic polar solvent is preferably a ratio of 1:1 to 1:30, and more preferably a ratio of 1:4 to 1:20.

The reaction temperature of the present reaction may be varied depending on the used reagent and the reaction condition, and it is usually under heating. The reaction temperature is preferably 20° C. to 120° C., more preferably 50° C. to 120° C., and further preferably 50° C. to 90° C., and further more preferably 60° C. to 90° C. (such as 70° C.).

The reaction time of the present reaction may be varied depending on the used reagent and the reaction condition, it is usually the time until the compound (a4) etc. has been disappeared from the reaction mixture. The reaction time is preferably 1 hour to 7 hours, and more preferable 10 hours to 20 hours.

Step a4

The compound (a6) and the compound (a5) can be reacted in the presence of the palladium catalyst (here the palladium catalyst is referred to as "palladium catalyst (2)[1]") in the presence or absence of a ligand, in the presence of a base, in a solvent to prepare the compound (a7)).

The present reaction can be conducted under a similar reaction condition to that of the process of the step a3.

Step a5

The compound (a7) can be reacted in the presence of a halogenating agent, in the presence of a base, in the presence or absence of a halogenated alkali metal, in a solvent to prepare the compound (a1-2-a).

Examples of the halogenating agent include a halogenating agent corresponding to $Z^{a1}$ of the compound (a1-2-a) to be prepared. When the compound (a1-2-a) wherein $Z^{a1}$ represents a chlorine atom (compound (a1-1-a)) is prepared, examples of the halogenating agent includes sodium hypochlorite, N-chlorosuccinimide, trichloroisocyanuric acid, and 1,3-dichloro-5,5-dimethyl hydantoin. Sodium hypochlorite, and N-chlorosuccinimide are preferably included, and sodium hypochlorite is more preferably included. When the compound (a1-2-a) wherein $Z^{a1}$ represents a bromine atom, examples of the halogenating agent include N-bromosuccinimide. When the compound (a1-2-a) wherein $Z^{a1}$ represents an iodine atom is prepared, examples of the halogenating agent include iodine molecule, and N-iodo succinimide. An iodine molecule is preferably included. When the iodine molecule is used, an iodination reaction progresses with a high regioselectivity. The equivalent amount of the halogenating agent used in the present reaction may be varied depending on the used reagent and the reaction condition, and is usually 1 mole equivalent to small excess amounts relative to the compound (a7), and is, for example, 1 to 1.5 mole equivalent amount(s), and preferably 1 to 1.2 mole equivalent amount(s). Examples of the compound (a1-2-a) prepared according to the present reaction include preferably a compound (a1-2-a) wherein $Z^{a1}$ represents an iodine atom.

The base in not particularly limited, and includes, for example, an alkali metal hydroxide (such as lithium hydroxide, sodium hydroxide, potassium hydroxide), and an alkali metal carbonate (such as sodium carbonate, potassium carbonate, cesium carbonate, sodium hydrogen carbonate, potassium hydrogen carbonate). The alkali metal hydroxide is preferably included. Examples of the alkali metal hydroxides include preferably sodium hydroxide. The equivalent amount of the base used in the present reaction may be varied depending on the used reagent and the reaction condition, and is usually 1 mole equivalent amount to excess amounts relative to the compound (a7), which is, for example, 1 to 5 mole equivalent amount(s), and preferably 1.5 to 3 mole equivalent amounts.

As the halogenated alkali metal, the halogenated alkali metal corresponding to $Z^{a1}$ of the compound (a1-2-a) to be prepared can be used. When the compound (a1-2-a) wherein $Z^{a1}$ represents an iodine atom is prepared, examples of the halogenated alkali metal include potassium iodide, sodium iodide, and cesium iodide, and preferably potassium iodide. The present reaction is preferably conducted in the presence of the halogenated alkali metal. The equivalent amount of the halogenated alkali metal used in the present reaction may be varied depending on the used reagent and the reaction condition, it is usually preferably a catalytic amount to small excess amount relative to the compound (a7), which is, for example, 0.01 to 1 mole equivalent amount(s), and preferably 0.05 to 0.3 mole equivalent amounts.

The solvent is not particularly limited as long as it is a reaction-inactive solvent, and includes, for example, water, ethers (such as 1,2-dimethoxyethane, diglyme, 1,4-dioxane, tetrahydrofuran, 2-methyltetrahydrofuran), or the mixed solvents of these solvents. Water is preferably included.

The reaction temperature of the present reaction may be varied depending on the used reagent and the reaction condition, and is preferably 0° C. to 50° C., and more preferably 10° C. to 40° C., and further preferably 20° C. to 30° C.

The reaction time of the present reaction may be varied depending on the used reagent and the reaction condition, and is usually the time until the compound (a7) has been disappeared from the reaction mixture. The reaction time is preferably 1 hour to 48 hours, and more preferably 5 hours to 18 hours.

Step a6

The $Z^{a2}$-1 in the compound (a1-3-a) can be deprotected to prepare the compound (a1-4-a).

The present reaction can be conducted under a similar reaction condition to that of the deprotection reaction of $P^1$ of the step a2.

In the present Reaction Scheme (I) {Reaction Schemes (I-I) to (I-VII)}, the compound (a1) etc., the compound (2) etc., the compound (a3-1) etc., the compound (a4), the compound (a5), the compound (a6), and the compound (a7) to be applied can be prepared appropriately, according to known method(s) as itself, or in combination of these methods.

The compound (a1) etc., the compound (2) etc., the compound (a3-1) etc., the compound (a4), the compound (5a), and the compound (a7) which are prepared in the present Reaction Scheme (I) can be converted into the compound (a1) {the compound (a1) and the compound [I(A)]}appropriately according to known method(s) as itself or in combination of these methods.

The compound wherein $R^2$ represents a methyl which may be optionally substituted with dialkylamino group or alkanoyloxy group can be converted into the compound wherein $R^2$ represents a methyl group according to the method described in above-mentioned Patent Literature 5.

Reaction Scheme (II-I)

[Chemical Formula 83]

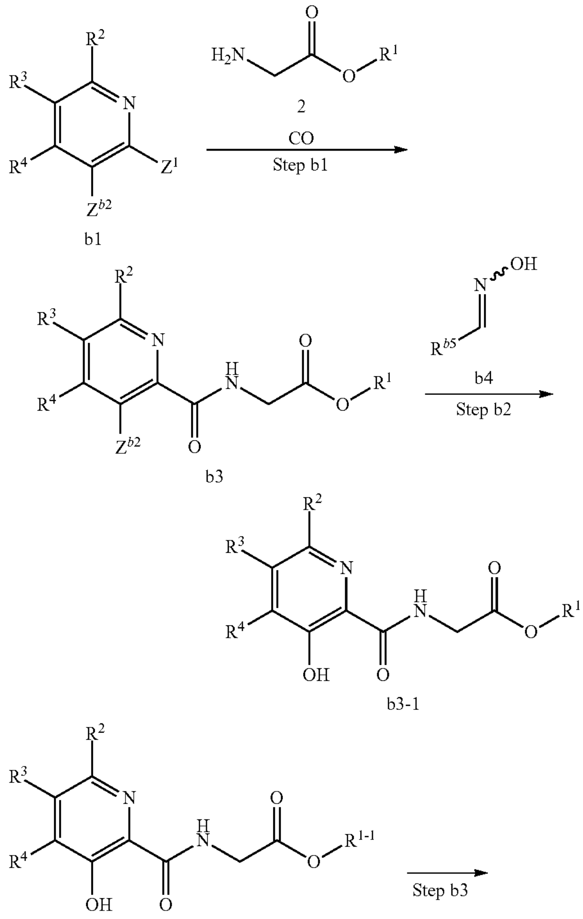

b1 b3 b3-1 b3-1-1

-continued

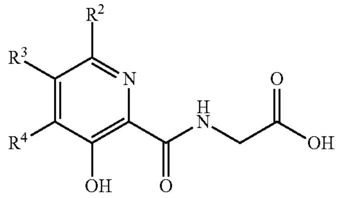

I (In the Reaction Scheme (II-1), $Z^1$ and $Z^{b2}$ each independently represents a chlorine atom, a bromine atom, or an iodine atom.

$R^1$ represents an optionally substituted alkyl group, a hydrogen atom, or a resin residue, and preferably an optionally substituted alkyl group, and more preferably an alkyl group. $R^{1-1}$ represents an optionally substituted alkyl group or a resin residue, preferably an optionally substituted alkyl group, and more preferably an alkyl group.

$R^2$ represents a hydrogen atom, or an optionally substituted methyl group.

$R^3$ represents a phenyl group which may be optionally substituted with halogen atom, a chlorine atom, a bromine atom, an iodine atom or a trifluoromethanesulfoxy group, $R^4$ represents a hydrogen atom, or alternatively $R^3$ and $R^4$ binds to each other and combine together with a pyridine group to which they are adjacent to form an isoquinoline group which may be optionally substituted with phenyloxy group.

$R^{b5}$ represents an optionally substituted aryl group, or an optionally substituted alkyl group, preferably an optionally substituted aryl group, and more preferably an optionally substituted phenyl group, and further more preferably a phenyl group.

Here the optionally substituted methyl group expressed as $R^2$ is not particularly limited as long as it is any substituent that can be converted into an unsubstituted methyl group. Examples of the optionally substituted methyl group include a methyl group which may be optionally substituted with a dialkylamino group or an alkanoyloxy group.

Examples of the phenyl group which may be optionally substituted with halogen atom expressed as $R^3$ include preferably a 3-chlorophenyl group.

When $R^3$ represents a chlorine atom, a bromine atom, an iodine atom, or a trifluoromethanesulfoxy group, preferably all of $Z^1$, $Z^{b2}$ and $R^3$ represent a chlorine atom, or all of them represent a bromine atom, and more preferably all of $Z^1$, $Z^{b2}$ and $R^3$ represent a chlorine atom.

As $R^2$, $R^3$ and $R^4$, preferably (i) $R^2$ represents a hydrogen atom, $R^3$ represents a 3-chlorophenyl group, and $R^4$ represents a hydrogen atom, or alternatively, (ii) $R^2$ represents a methyl group, and $R^3$ and $R^4$ binds to each other and combine together with a pyridine group to which they are adjacent to form a 7-phenyloxy-isoquinoline group).

Reaction Scheme (II-II)

[Chemical Formula 84]

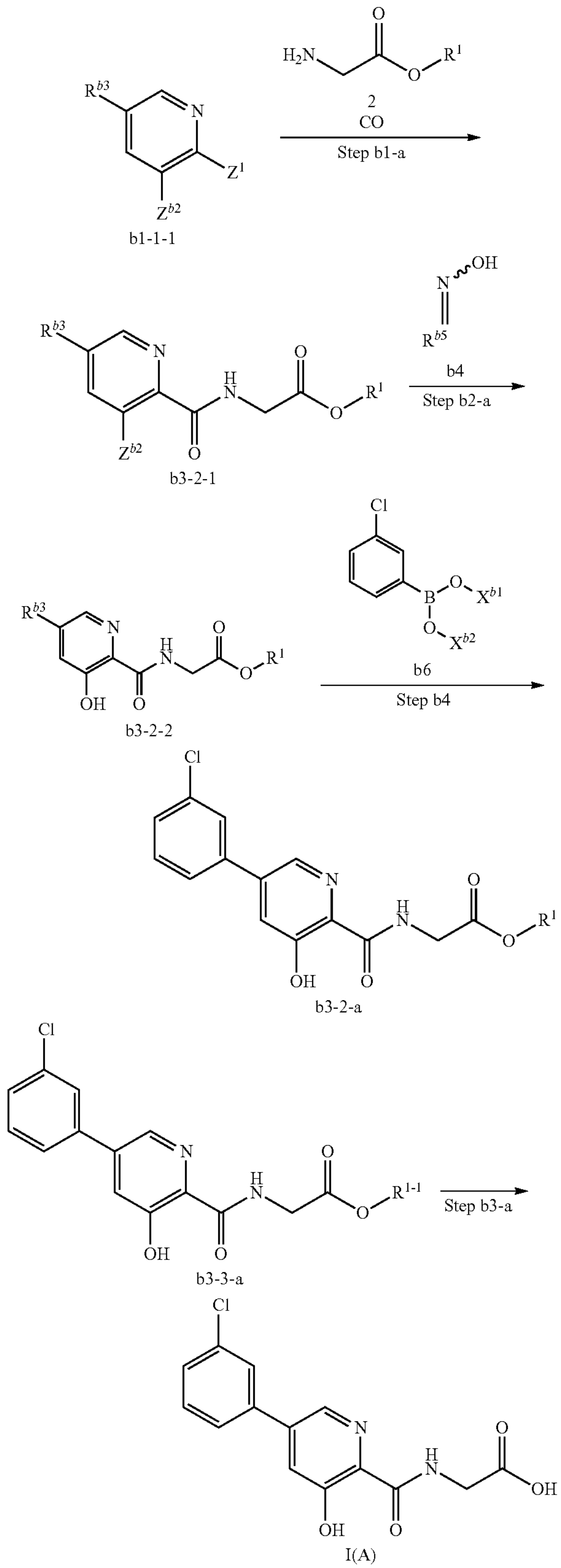

b1-1-1 b3-2-1 b3-2-2 b3-2-a b3-3-a

I(A)

(In the Reaction Scheme (II-II), $Z^1$ and $Z^{b2}$ each independently represents a chlorine atom, a bromine atom, or an iodine atom, $R^{b3}$ represents a chlorine atom, a bromine atom, an iodine atom, or a trifluoromethanesulfoxy group, and preferably all of $Z^1$, $Z^{b2}$ and $Z^{b3}$ represent a chlorine atom, or all of them represent a bromine atom, and more preferably all of $Z^1$, $Z^{b2}$ and $Z^{b3}$ represent a chlorine atom.

$R^1$ represents an optionally substituted alkyl group, a hydrogen atom or a resin residue, preferably an optionally substituted alkyl group, and further preferably an alkyl group. $R^{1-1}$ represents an optionally substituted alkyl group or a resin residue, and preferably an optionally substituted alkyl group, and more preferably an alkyl group.

$R^{b5}$ represents an optionally substituted aryl group or an optionally substituted alkyl group, preferably an optionally substituted aryl group, and more preferably an optionally substituted phenyl group, and further preferably a phenyl group.

$X^{b1}$ and $X^{b2}$ each independently represents a hydrogen atom or an alkyl group, or alternatively both of them binds to each other to form an alkylene group, and preferably each of them represents a hydrogen atom.)

Reaction Scheme (II-II)

[Chemical Formula 85]

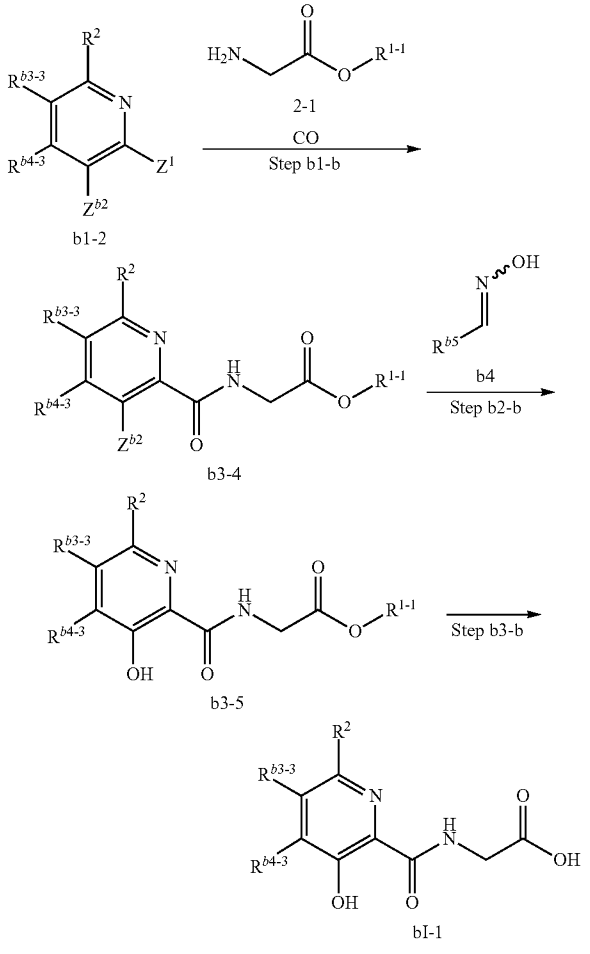

b1-2 b3-4 b3-5 bI-1

(In Reaction Scheme (II-III), $Z^1$ and $Z^b2$ each independently represents a chlorine atom, a bromine atom, or an iodine atom, preferably $Z^1$ and $Z^{b2}$ each represents a chlorine atom, or each represents a bromine atom, more preferably, $Z^1$ and $Z^{b2}$ each represents a chlorine atom.

$R^{1-1}$ represents an optionally substituted alkyl group or a resin residue, preferably represents an optionally substituted alkyl group, and more preferably represents an alkyl group.

$R^2$ represents a hydrogen atom, or an optionally substituted methyl group.

$R^{b3-3}$ represents a 3-chlorophenyl group, a chlorine atom, a bromine atom, an iodine atom, or a trifluoromethanesulfoxy group, $R^{b4-3}$ represents a hydrogen atom, or alternatively, $R^{b3-3}$ and $R^{4-3}$ binds to each other and combine together with a pyridine group to which they are adjacent to form a 7-phenyloxy-isoquinoline group.

$R^{b5}$ represents an optionally substituted aryl group or an optionally substituted alkyl group, preferably represents an optionally substituted aryl group, and more preferably represents an optionally substituted phenyl group, and further more preferably represents a phenyl group.

Here the optionally substituted methyl group expressed as $R^2$ is not particularly limited as long as it is any substituent that can be converted into an unsubstituted methyl group. Examples of the optionally substituted methyl group include a methyl group which may be optionally substituted with dialkylamino group or alkanoyloxy group.

As $R^2$, $R^{b3-3}$, and $R^{b4-3}$, preferably (i) $R^2$ represents a hydrogen atom, $R^{b3-3}$ represents a 3-chlorophenyl group, and $R^{b4-3}$ represents a hydrogen atom, or alternatively, (ii) $R^2$ represents a methyl group, and $R^{b3-3}$ and $R^{b4-3}$ binds to each other and combine together with a pyridine group to which they are adjacent to form a 7-phenyloxy-isoquinoline group)

Step b1, Step b1-a, and Step b1-b

The compound (b1), the compound (b1-1-1) or the compound (b1-2) (hereinafter, these compounds may be collectively referred to as "Compound (b1) etc."), the compound (2) or salts thereof, are reacted with a carbon monoxide in the presence of a palladium catalyst (here the palladium catalyst is referred to as "palladium catalyst (b1)") in the presence or absence of a ligand, in the presence of a base, in a solvent to prepare the compound (b3), the compound (b3-2-1) or the compound (b3-4) (hereinafter, these compounds may be collectively referred to as "Compound (b3) etc.").

The present reaction can be conducted under a similar reaction condition to that of the reaction of the step a1.

Step b2, Step b2-a, and Step b2-b

The compound (b3) etc. and the compound (b4) etc. are reacted in the presence of a palladium catalyst (here the palladium catalyst is referred to as "palladium catalyst (b2)") in the presence or absence of a ligand, in the presence of a base, in a solvent to prepare the compound (b3-1), the compound (b3-2-2) or the compound (b3-5) (hereinafter, these compounds may be collectively referred to as "compound (b3-1) etc.").

The equivalent amount of the compound (b4) used in the present reaction may be varied depending on the used reagent or the reaction condition, and is usually preferably 1 mole equivalent amount to excess amounts, which is, for example 1 to 5 mole equivalent amount(s) and preferably 1 to 1.5 equivalent amount(s).

The palladium catalyst (b2) can be used in the presence or absence of a ligand in the present reaction. The palladium catalyst (b2) is not particularly limited as long as it is a general palladium catalyst, and includes, for example, tetrakis (triphenylphosphine)palladium (0), dichlorobis(tricyclohexylphosphine)palladium (II), palladium (II) acetate, bis(acetonitrile)dichloropalladium (II), dichlorobis(triphenylphosphine)palladium (II), dichloro[1,3-bis(diphenylphosphino)propane]palladium (II), [1,1'-bis(diphenylphosphino)ferrocene]dichloropalladium (II), tris (dibenzylideneacetone)dipalladium (0), palladium (II) chloride, [(2-di-tert-butylphosphino-3-methoxy-6-methyl-2',4',6'-triisopropyl-1,1'-biphenyl)-2-(2'-aminobiphenyl)] palladium (II) methanesulfonate (RockPhos Pd G3), (2-di-tert-butylphosphino-3,4,5,6-tetramethyl-2',4',6'-triisopropyl-1,1'-biphenyl) (2'-amino-1,1'-biphenyl-2-yl) palladium (II) methanesulfonate (Me4tBuXPhos Pd G3), [(2-di-tert-butylphosphino-3,6-dimethoxy-2',4',6'-triisopropyl-1,1'-biphenyl) (2'-amino-1,1'-biphenyl-2-yl)]palladium (II) methanesulfonate (tBuBrettPhos Pd G3), [(2-di-tert-butylphosphino-2',4',6'-triisopropyl-1,1'-biphenyl) (2'-amino-1,1'-biphenyl-2-yl)]palladium (II) methanesulfonate (tBuXPhos Pd G3), [2-(di-1-adamanthylphosphino)-2',4',6'-triisopropyl-3,6-dimethoxybiphenyl][2-(2'-amino-1,1'-biphenyl)]palladium (II) methanesulfonate (AdBrettPhos Pd G3). The ligand is not particularly limited as long as it is a general ligand, and includes, for example, a monodentate phosphine ligand.

When the palladium catalyst (b2) is used in the presence or absence of a ligand in the present reaction, preferably, the palladium catalyst having one or more monodentate phosphine ligand selected from tetrakis(triphenylphosphine)palladium (0), dichlorobis(tricyclohexylphosphine)palladium (II), [(2-di-tert-butylphosphino-3-methoxy-6-methyl-2',4',6'-triisopropyl-1,1'-biphenyl)-2-(2'-aminobiphenyl)]palladium (II) methanesulfonate (RockPhos Pd G3), (2-di-tert-butylphosphino-3,4,5,6-tetramethyl-2',4',6'-triisopropyl-1,1'-biphenyl) (2'-amino-1,1'-biphenyl-2-yl)palladium (II) methanesulfonate (Me4tBuXPhos Pd G3), [(2-di-tert-butylphosphino-3,6-dimethoxy-2',4',6'-triisopropyl-1,1'-biphenyl) (2'-amino-1,1'-biphenyl-2-yl)]palladium (II) methanesulfonate (tBuBrettPhos Pd G3), [(2-di-tert-butylphosphino-2',4',6'-triisopropyl-1,1'-biphenyl) (2'-amino-1,1'-biphenyl-2-yl)]palladium (II) methanesulfonate (tBuXPhos Pd G3), [2-(di-1-adamanthylphosphino)-2',4',6'-triisopropyl-3,6-dimethoxybiphenyl][2-(2'-amino-1,1'-biphenyl)]palladium (II) methanesulfonate (AdBrettPhos Pd G3) is used in the absence of ligand, or alternatively the palladium catalyst not having a monodentate phosphine ligand selected from palladium (II) acetate, bis(bis(acetonitrile))dichloropalladium (II), tris(dibenzylideneacetone)dipalladium (0) and palladium (II) chloride can be used in the presence of one or more monodentate phosphine ligand, more preferably the palladium catalyst not having a monodentate phosphine ligand selected from palladium (II) acetate, bis(bis(acetonitrile))dichloropalladium (II), [1,1'-bis (diphenylphosphino)ferrocene]dichloropalladium (II), tris (dibenzylideneacetone)dipalladium (0) and palladium (II) chloride can be used in the presence of one or more monodentate phosphine ligand(s), and further more preferably palladium (II) acetate can be used in the presence of one or more monodentate phosphine ligand(s).

Examples of the monodentate phosphine ligand include tricyclohexylphosphine, triphenylphosphine, 2-di-tert-butylphosphino-3-methoxy-6-methyl-2',4',6'-triisopropyl-1,1'-biphenyl (RockPhos), 2-di-tert-butylphosphino-3,4,5,6-tetramethyl-2',4',6'-triisopropyl-1,1'-biphenyl (Me4tBuXPhos), 2-di-tert-butylphosphino-3,6-dimethoxy-2',4',6'-triisopropyl-1,1'-biphenyl (tBuBrettPhos), 2-di-tert-butylphosphino-2',4',6'-triisopropyl-1,1'-biphenyl (tBuX-Phos), 2-(di-1-adamanthylphosphino)-2',4',6'-triisopropyl-3,6-dimethoxybiphenyl (AdBrettPhos), and preferably include tricyclohexylphosphine, and RockPhos. From the aspect of ligand cost, since tricyclohexylphosphine is low-cost, it is preferred.

The equivalent amount of the palladium catalyst (b2) used in the present reaction may be varied depending on the used reagent and the reaction condition, and is usually preferably a catalytic amount of the compound (b3) etc., which is, for example, 0.001 to 0.1 mole equivalent amounts and preferably 0.01 to 0.05 mole equivalent amounts, relative to the compound (b3) etc. When the reaction is conducted in the presence of a ligand, the equivalent amount of the ligand may be varied depending on the used reagent or the reaction condition, and is usually 1 to 5 mole equivalent amount(s), and preferably 2 to 3 equivalent amounts, relative to the palladium catalyst (b2).

The base is not particularly limited, and includes, for example, a trialkylamine (such as tripropylamine, N,N-diisopropylethyl amine), a sodium salt (such as sodium acetate, sodium carbonate, sodium hydrogen carbonate, trisodium phosphate), a potassium salt (such as potassium acetate, potassium carbonate, potassium hydrogen carbonate, tripotassium phosphate), a cesium salt (such as cesium acetate, cesium carbonate, cesium hydrogen carbonate). A potassium salt and a cesium salt are preferably included, and cesium salt is particularly preferably included. Examples of the potassium salt includes preferably tripotassium phosphate. Examples of the cesium salt include preferably cesium carbonate.

The equivalent amount of the base used in the present reaction may be varied depending on the used reagent or the reaction condition, and is usually 1 to 10 mole equivalent amount(s), and preferably 1.5 to 5 mole equivalent amounts, relative to the compound (b3) etc.

The solvent is not particularly limited as long as it is a reaction-inactive solvent, and include, for example, nitriles (such as acetonitrile, benzonitrile), esters (such as ethyl acetate, isopropyl acetate), aromatic hydrocarbons (such as toluene, xylene), aprotic polar solvent (such as N,N-dimethylformamide, N-methylpyrrolidone), sulfoxides (such as dimethylsulfoxide), ethers (such as 1,2-dimethoxyethane, diglyme, 1,4-dioxane, tetrahydrofuran, 2-methyltetrahydrofuran). Ethers are preferably included. Examples of the ethers include preferably 2-methyl-tetrahydrofuran.

The reaction temperature of the present reaction may be varied depending on the used reagent and the reaction condition, and is usually under heating. The reaction temperature is preferably 60° C. to 100° C., and more preferably 70 to 90° C. The reaction time of the present reaction may be varied depending on the used reagent or the reaction condition, and is usually the time until the compound (b3) etc. has been disappeared from the reaction mixture. The reaction time is preferably 1 hour to 72 hours, and more preferably 5 hours to 25 hours.

Step b3, Step b3-a, and Step b3-b

The compound (b-3-1-1), the compound (b3-3-a) or the compound (b3-5) (hereinafter, these compounds may be collectively referred to as "Compound (b3-1-1) etc.") can be subjected to a deprotection reaction according to a similar method to those described in the Patent Literature 1 or 2 to prepare the compound (I), the compound [I(A)] or the compound (b-I-1).

The present reaction can be conducted under a similar reaction condition to that of the step a2.

Step b4

The compound (b3-2-2) and the compound (b6) or the equivalent compound of the compound (b6) can be reacted in the presence of trialkylamine, in the presence of a palladium catalyst (here the palladium catalyst is referred to as "palladium catalyst (b3)") in the presence or absence of a ligand in a solvent to prepare the compound (b3-2-a).

The equivalent amount of the compound (b6) used in the present reaction may be varied depending on the used reagent or the reaction condition, and is usually preferably 1 mole equivalent amount to small excess amounts relative to the compound (b3-2-2), which is, for example 1 to 1.5 mole equivalent amount(s), and preferably 1 to 1.1 mole equivalent amount (s).

The equivalent amount of the compound (b6) used in the present reaction includes, for example, the boroxine compound which is the compound (b6-a) represented by formula:

[Chemical Formula 86]

b6-a

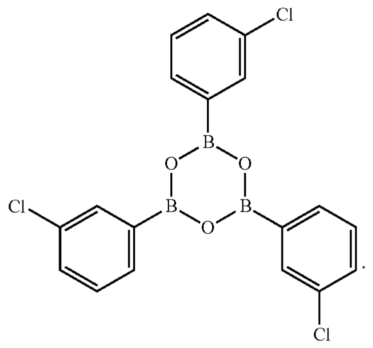

The equivalent amounts of the compound (a6-a) used in the present reaction may be varied depending on the used reagent or the reaction condition, and is usually 0.3 to 0.5 mole equivalent amounts, and preferably 0.3 to 0.4 mole equivalent amounts, relative to the compound (b5-1-a).

The trialkylamine is not particularly limited, and includes, for example, triethylamine, and N,N-diisopropyl ethyl amine, and preferably N,N-diisopropyl ethyl amine. The equivalent amount of the trialkyl amine used in the present reaction may be varied depending on the used reagent or the reaction condition, and usually includes a range of 1 mole equivalent amount to excess amounts relative to the compound (b-3-2), which is, for example, 1 to 10 mole equivalent amount(s), and preferably 2 to 5 mole equivalent amounts.

The palladium catalyst (b3) can be used in the presence or absence of a ligand in the present reaction. The palladium catalyst (b3) is not particularly limited as long as it is a general palladium catalyst, and includes, for example, a nitrogen-containing heterocyclic carbene palladium complex catalyst (NHC—Pd complex catalyst (b3-1)), palladium (II) acetate, bis(acetonitrile)dichloropalladium (II), tris(dibenzylideneacetone)dipalladium (0), and palladium (II) chloride. The ligand is not particularly limited as long as it is a general ligand, and includes, for example, the nitrogen-containing heterocyclic carbene ligand precursor, and the corresponding azorium salt ligand precursor (such as imidazolium salt ligand precursor).

When the palladium catalyst (b3) is used in the presence or absence of a ligand in the present reaction, preferably, NHC—Pd complex catalyst (b3-1) is used in the absence of a ligand, or alternatively, a palladium catalyst not having nitrogen-containing heterocyclic carbene ligand selected from palladium (II) acetate, bis(acetonitrile)dichloropalladium (II), tris(dibenzylideneacetone)dipalladium (0), and palladium (II) chloride can be used in the presence of one or more of the nitrogen-containing heterocyclic carbene ligand(s) or the corresponding azorium salt ligand precursor(s), and more preferably the NHC—Pd complex catalyst (b3-1) can be used in the presence of a ligand.

Examples of the NHC—Pd complex catalyst (b3-1) include allylchloro [1,3-bis(2,6-diisopropylphenyl)imidazol-2-ylidene]palladium (II) (CX21), allylchloro [1,3-bis(2,4,5-trimethylphenyl)imidazol-2-ylidene]palladium (II) (CX22), chlorophenyl allyl [1,3-bis(2,6-diisopropylphenyl)imidazol-2-ylidene]palladium (II) (CX31), chlorophenyl allyl [1,3-bis(2,6-diisopropylphenyl)-2-imidazolidene]palladium (II) (CX32), chlorophenyl allyl {1,3-bis[2,6-bis(diphenylmethyl)-4-methylphenyl]-2-imidazolidene}palladium (II) (CX33). More preferably CX33 is included. Examples of the nitrogen-containing heterocyclic carbene ligand include 1,3-bis(2,6-diisopropylphenyl)imidazol-2-ylidene, 1,3-bis(2,4,5-trimethylphenyl)imidazol-2-ylidene, 1,3-bis[2,6-bis(diphenylmethyl)-4-methylphenyl]-2-imidazolidene. The corresponding azorium salt ligand precursor is not particularly limited as long as it is an azorium salt ligand precursor which is reacted with a base to produce the desired nitrogen-containing heterocyclic carbene ligand.

The equivalent amount of the palladium catalyst (b3) used in the present reaction may be varied depending on the used reagent or the reaction condition, and is usually, a catalytic amount of the compound (b3-2-2), which is, for example, 0.001 to 0.1 mole equivalent amounts, and preferably 0.01 to 0.05 mole equivalent amounts, relative to the compound (b3-2-2). When the reaction is conducted in the presence of a ligand, the equivalent amount of the ligand may be varied depending on the used reagent or the reaction condition, and is usually 1 to 5 mole equivalent amount(s), and preferably 2 to 3 mole equivalent amounts, relative to the palladium catalyst (b3).

The solvent is not particularly limited as long as it is a reaction-inactive solvent, and includes, for example, aromatic hydrocarbons (such as toluene, xylene), esters (such as ethyl acetate, butyl acetate, isopropyl acetate), aprotic polar solvents (such as N,N-dimethyl formamide, N-methylpyrrolidone), sulfoxides (such as dimethyl sulfoxides), alkyl alcohols (such as methanol, ethanol, isopropyl alcohol, t-butyl alcohol), ethers (such as 1,4-dioxane, tetrahydrofuran, 1,2-dimethoxyethane), nitriles (such as acetonitrile, benzonitrile), and water, or mixed solvents of two or more of these solvents. Preferably a mixed solvent of water and the other solvents (one or more solvent(s) selected from aromatic hydrocarbons, esters, aprotic polar solvents, sulfoxides, alkyl alcohols, ethers, and nitriles) is included, and more preferably a mixed solvent composed of water and aromatic hydrocarbons (preferably toluene), or a mixed solvent of water and alkyl alcohols (preferably methanol) is included, and further preferably, a mixed solvent composed of water and aromatic hydrocarbons (preferably toluene) is included. When the present reaction is conducted in a mixed solvent composed of water and the other solvents, the mixed ratio of each solvent is usually 10:1 to 1:10, and preferably 4:1 to 1:4.

The reaction temperature of the present reaction may be varied depending on the used reagent or the reaction condition, and it is usually under heating. The reaction temperature is preferably 50° C. to 120° C., and more preferably 70 C to 90° C.

The reaction time of the present reaction may be varied depending on the used reagent or the reaction condition, and is usually a time until the compound (b-3-2) has been disappeared from the reaction mixture. The reaction time is preferably 1 hour to 72 hours, and more preferably 10 hours to 20 hours.

In the present Reaction Scheme (II) {Reaction Schemes (II-I) to (II-II)}, the compound (b1) etc., the compound (2) or salts thereof, the compound (b3) etc., the compound (b3-1-1) etc., and the compound (b3-2-2) to be applied can be prepared appropriately according to known method(s) as itself or in combination of these methods.

The compound (b3) etc., the compound (b3-1) etc. and the compound (b3-a) can be prepared appropriately according to known method(s) as itself or in combination of them, to convert into the compound (I), the compound [I(A)] or the compound (bI-1).

The compound wherein $R^2$ represents a methyl group which may be optionally substituted with alkylamino group or an alkanoyloxy group can prepared according to a similar method to that of the Patent Literature 5 to convert into the compound wherein $R^2$ represents a methyl group.

Reaction Scheme (III)

[Chemical Formula 87]

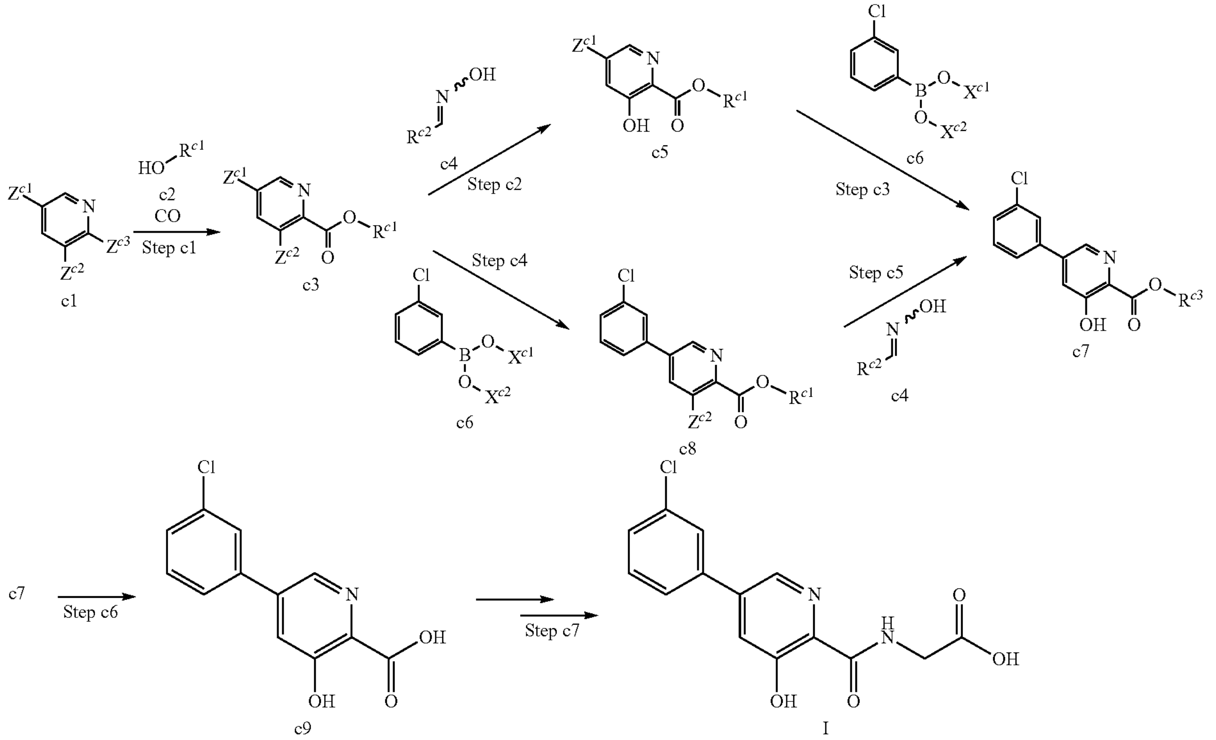

(wherein $Z^{c1}$, $Z^{c2}$, and $Z^{c3}$ each independently represents a chlorine atom or a bromine atom, preferably $Z^{c1}$, $Z^{c2}$, and $Z^{c3}$ each represents a chlorine atom or each represents a bromine atom, and more preferably $Z^{c1}$, $Z^{c2}$, and $Z^{c3}$ each represents a chlorine atom.

$R^{c1}$ represents an alkyl group.

$R^{c2}$ represents an optionally substituted aryl group or an optionally substituted alkyl group, preferably represents an optionally substituted aryl group, and more preferably represents an optionally substituted phenyl group, and further preferably represents a phenyl group.

$X^{c1}$ and $X^{c2}$ each independently represents a hydrogen atom or an alkyl group, or alternatively both of them bind to each other to form an alkylene group, and preferably each represents a hydrogen atom).

Step c1

The compound (c1), the compound (c2), and a carbon monoxide can be reacted in the presence of a palladium catalyst (here the palladium catalyst is referred to as "palladium catalyst (c1)"), in the presence or absence of a ligand, in the presence of a base, in a solvent to prepare the compound (c3).

The present reaction can be conducted under a similar reaction condition to those of the methods of the step a1 or the step b1.

Step c2

The compound (c3) and the compound (c4) can be reacted in the presence of a palladium catalyst (here the palladium catalyst is referred to as "palladium catalyst (c2)"), in the presence or absence of a ligand, in the presence of a base, in a solvent, to prepare the compound (c5).

The present reaction can be conducted under similar reaction condition to that of the method of the step b2.

Step c3

The compound (c5) and the compound (c6) can be reacted in the presence of a base, in the presence of a palladium catalyst (here the palladium catalyst is referred to as "palladium catalyst (c3)"), in the presence or absence of a ligand, in the solvent to prepare the compound (c7).

The present reaction can be conducted under a similar reaction condition to those of the methods of the step a3 or the step b4.

Step c4

The compound (c3) and the compound (c6) can be reacted in the presence of a base, in the presence of a palladium catalyst (here the palladium catalyst is referred to as "palladium catalyst (c3)"), in the presence or absence of a ligand, in a solvent to prepare the compound (c8).

The present reaction can be conducted under a similar reaction condition to that of the reaction of the step c3.

Step 5

The compound (c8) and the compound (c4) can be reacted in the presence of a palladium catalyst (here the palladium catalyst is referred to as "palladium catalyst (c2)"), in the presence or absence of a ligand, in the presence of a base, in a solvent to prepare the compound (c7).

The present reaction can be conducted under a similar reaction condition to that of the method of the step c2.

Step c6

The compound (c7) can be subjected to a hydrolysis reaction according to a similar method to that described in the step b3 to prepare the compound (c9).

Step c7

The compound (c9) can be subjected to a deprotection reaction, for example, according to the similar method to that described in the Patent Literature 2 to prepare the compound [I(A)].

In the present Reaction Scheme (III), the compound (c1), the compound (c3), the compound (c5), the compound (c7), the compound (c8), and the compound (c9) to be applied can be prepared appropriately according to known method(s) as itself or in combination of these methods.

The compound (c3), the compound (c5), the compound (c7), the compound (c8), and the compound (c9), which were prepared by the present Reaction Scheme (III), can be converted appropriately, according to known method(s) as itself or in combination of these methods into the compound [I(A)].

The compound (a1-a) below represented by formula:

[Chemical Formula 88]

a1-a

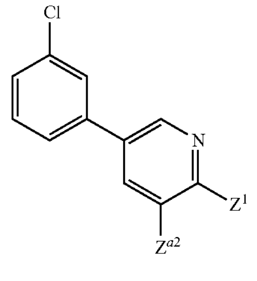

{wherein $Z^1$ represents a chlorine atom, a bromine atom or an iodine atom, $Z^{a2}$ represents a hydroxy group or the substituent represented by formula:

[Chemical Formula 89]

(wherein $P^1$ represents a protecting group for hydroxy group)} is a novel compound, which is also encompassed by the present invention.

Here, the protecting group for a hydroxy group expressed as $P^1$ is not particularly limited, and include, preferably a methyl group which may be optionally substituted with one or two methoxy(s) (such as methyl, benzyl, p-methoxybenzyl), an alkoxymethyl group which may be optionally substituted with trialkylsilyl (such as methoxymethyl, triethylsilylethoxymethyl), an alkanoyl group (such as acetyl, pivaloyl), a sulfonyl group which may be optionally substituted with an optionally substituted methyl or an optionally substituted phenyl (such as methanesulfonyl, benzenesulfonyl, p-toluenesulfonyl, o-nitrobenzenesulfonyl), an optionally substituted alkyloxycarbonyl group (such as t-butyloxycarbonyl, benzyloxycarbonyl), a silyl group which is substituted with three groups selected from an alkyl group and an optionally substituted phenyl group (such as triethylsilyl, triisopropylsilyl, tert-butyldimethyl silyl, tert-butyl diphenyl silyl), and an aminocarbonyl group which is substituted with one or two substituents selected from an optionally substituted alkyl group and an optionally substituted phenyl group (such as dimethyl aminocarbonyl, methyl phenyl aminocarbonyl). More preferably, a methyl group which is substituted with a phenyl group which may be optionally substituted with one or two methoxy(s) (such as benzyl, p-methoxybenzyl), an alkanoyl group (such as pivaloyl), and a sulfonyl group which is substituted with an optionally substituted methyl group or an optionally substituted phenyl group (such as methanesulfonyl, benzenesulfonyl, p-toluenesulfonyl, o-nitrobenzenesulfonyl) is included.

Preferably, $Z^1$ represents a chlorine atom, a bromine atom, or an iodine atom, and $Z^{a2}$ represents a hydroxy group. More preferably, $Z^1$ represents a chlorine atom, and $Z^{a2}$ represents a hydroxy group.

A crystal of the compound (a3-1-A) represented by formula:

[Chemical Formula 90]

a3-1-A

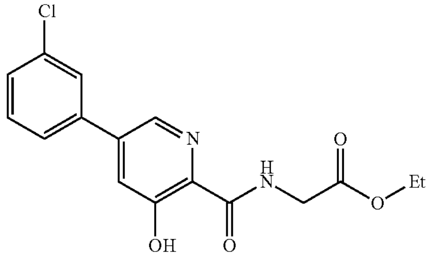

is a novel crystal, which is also encompassed by the present invention.

Two types of the crystals (that is, I type crystal and II type crystal) of the compound (a3-1-A) are preferable crystals that can be removed impurity materials effectively. Among these crystals, the II type crystal is more preferred in terms of the remove of the impurity materials. Also the I type crystal is more thermodynamical stable, which is more preferred in terms of the robustness of the industrial process.

EXAMPLES

Next, the process of the present invention is explained specifically by indicating the examples as follows, but should not be limited to these examples.

In the present examples, each symbol has the following meaning.

Ac: acetyl

Bn: benzyl

Boc: tert-butyloxycarbonyl

Cbz: benzyloxycarbonyl

Me: methyl

Et: ethyl nPr: propyl iPr/2-Pr: isopropyl t-Bu: tert-butyl

MOM: methoxy methyl

Ms: methanesulfonyl

Piv: pivaloyl

PMB: p-methoxybenzyl

SEM: 2-(trimethylsilyl)ethoxy methyl

Ts: p-toluenesulfonyl $Pd(OAc)_2$: palladium (II) acetate $Pd_2$ $(dba)_3$: tris(dibenzylideneacetone)dipalladium (0)

$Pd(dppf)Cl_2$: [1,1'-bis(diphenylphosphino)ferrocene]dichloropalladium (II) $Pd(PPh_3)_4$: tetrakis(triphenylphosphine)palladium (0)

$P(tBu)_3PdG2$: chloro[(tri-tert-butylphosphine)-2-(2-aminobiphenyl)]palladium (II)

$PdCl_2$ $(amphos)_2$: bis(di-tert-butyl(4-dimethylaminophenyl)phosphine)dichloro palladium (II)

CX21: allylchloro[1,3-bis(2,6-diisopropylphenyl)imidazol-2-ylidene]palladium (II)

CX22: allylchloro[1,3-bis(2,4,6-trimethylphenyl)imidazol-2-ylidene]palladium (II)

CX31: chlorophenylallyl[1,3-bis(2,6-diisopropylphenyl) imidazol-2-ylidene]palladium (II)

CX32: chlorophenylallyl[1,3-bis(2,6-diisopropylphenyl)-2-imidazolidene]palladium (II)

CX33: 3-chlorophenylallyl{1,3-bis[2,6-bis(diphenylmethyl)-4-methylphenyl]-2-imidazolidene}palladium (II)

BINAP: 2,2'-bis(diphenylphosphino)-1,1'-binapthyl tolBINAP: 2,2'-bis(di-p-triphosphino)-1,1'-binapthyl dppp: 1,3-bis(diphenylphosphino)propane dppf: 1,1'-bis(diphenylphosphino)ferrocene RockPhos: 2-di(tert-butyl)phosphino-2',4',6'-triisopropyl-3-methoxy-6-methyl biphenyl $PCy_3$: tricyclohexylphosphine Xantphos: 4,5-bis(diphenylphosphino)-9,9-dimethylxanthene $Et_3N$: triethylamine $iPr_2NEt$: N,N-diisopropyl ethyl amine DBU: diazabicyclo undecene DME: 1,2-dimethoxyethane DMF: N,N-dimethylformamide MeCN: acetonitrile THF: tetrahydrofuran 2-MeTHF: 2-methyltetrahydrofuran MEK: methyl ethyl ketone aq.: aqueous solution MsOH: methanesulfonic acid The numerical value of the pressure used in the present examples represents a numerical value of absolute pressure. For example, the description of "0.6 MPa" in the examples represents "0.6 MPa abs".

Example 1

Preparation of 2-chloro-5-(3-chlorophenyl)-3-hydroxypyridine

[Chemical Formula 91]

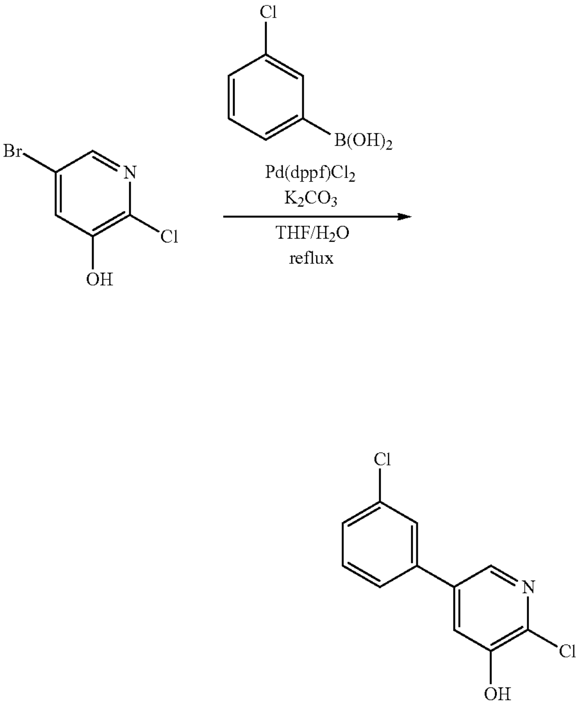

5-Bromo-2-chloro-3-hydroxypyridine (6.50 g, 31.184 mmol), $Pd(dppf)Cl_2$ (22.9 mg, 0.031 mmol), (3-chlorophenyl)boronic acid (5.37 g, 34.302 mmol), potassium carbonate (21.55 g, 155.920 mmol), tetrahydrofuran (44.0 mL), and water (22.0 mL) were added to a reactor vessel, and the mixture was stirred under reflux for 21.5 hours. After the inner temperature was cooled to 40° C., water (44.0 mL) was added to the reaction mixture, and the resulting mixture was stirred. Further, toluene (33.0 mL) was added thereto, and the resulting mixture was stirred. After standing gently, the lower layer which was obtained by separating into two layers was recovered, and water (19.5 mL) was added thereto. 2 mol/L Hydrochloric acid (15.6 mL) was added dropwise thereto, and a crystallization by neutralization was conducted. The obtained solid was collected through filtration under reduced pressure, and dried under reduced pressure to obtain 2-chloro-5-(3-chlorophenyl)-3-hydroxypyridine group (5.10 g). (Yield 68%)

$^1H$ NMR (500 MHz, DMSO-$d_6$) δ 10.93 (s, 1H), 8.21 (d, 1H, J=2.3 Hz), 7.74 (t, 1H, J=1.6 Hz), 7.62 (dt, 1H, J=7.3, 1.6 Hz), 7.48-7.55 (m, 3H)

Example 2

Preparation of 5-(3-chlorophenyl)-3-hydroxypyridine

[Chemical Formula 92]

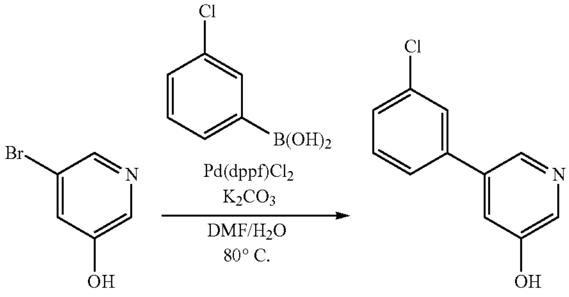

5-Bromo-3-hydroxypyridine (8.00 g, 45.977 mmol), $Pd(dppf)Cl_2$ (841.0 mg, 1.149 mmol), (3-chlorophenyl)boronic acid (8.63 g, 55.172 mmol), potassium carbonate (7.28 g, 52.673 mmol), N,N-dimethyl formamide (43.60 mL), and water (5.20 mL) were added to a reactor vessel, and the mixture was stirred at 80° C. for 16 hours. Water (100 mL) and 2-methyltetrahydrofuran (50 mL) were added to the reaction mixture, and the mixture was stirred at room temperature. The resulting mixture was separated with a separatory funnel and the aqueous layer was extracted with 2-methyl tetrahydrofuran (50 mL) twice. The organic layer was combined, and the mixture was washed with saturated aqueous sodium chloride solution (150 mL). Sodium sulfate was added to the organic layer separated with a separatory funnel, and the mixture was dehydrated, and then filtered, and the resulting filtrates were concentrated under reduced pressure. Acetone (50 mL) was added to the concentrated residue, and the mixture was stirred, and then impurity materials were recovered by filtration under reduced pressure and then washed with acetone (20 mL). The mixture was dried under reduced pressure to obtain 5-(3-chlorophenyl)-3-hydroxypyridine (7.59 mg) as pale brown solid. (Yield 80%) $^1$H NMR (500 MHz, DMSO-$d_6$) δ 10.12 (s, 1H), 8.37 (d, 1H, J=1.8 Hz), 8.17 (d, 1H, J=2.6 Hz), 7.74 (t, 1H, J=1.8 Hz), 7.64 (dt, 1H, J=7.6, 1.5 Hz), 7.45-7.54 (m, 2H), 7.41 (t, 1H, J=2.4 Hz)

Example 3

Preparation of 5-(3-chlorophenyl)-3-hydroxy-2-iodopyridine

[Chemical Formula 93]

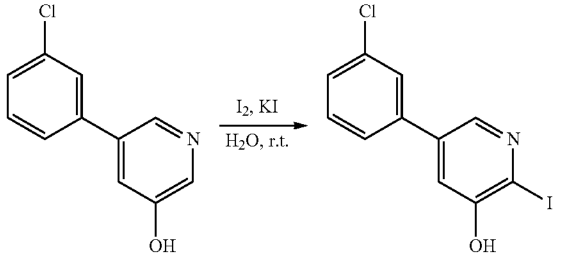

5-(3-Chlorophenyl)-3-hydroxypyridine (100.00 mg, 0.486 mmol), 8 mol/L aqueous sodium hydroxide solution (0.122 mL, 0.973 mmol), iodine (130.40 mg, 0.511 mmol), potassium iodide (43.10 mg, 0.258 mmol), and water (6.4 mL) were added to a reactor vessel, and the mixture was stirred at room temperature for 16 hours. Acetic acid (0.5 mL) was added to the reaction mixture, and the mixture was stirred at room temperature for 10 minutes. The precipitated solid was collected through a suction filtration, and the obtained solid was dried by heating under reduced pressure to obtain a desired 5-(3-chlorophenyl)-3-hydroxy-2-iodopyridine (140.20 mg). (Yield 86%)

$^1$H NMR (500 MHz, DMSO-$d_6$) δ11.07 (br, 1H), 8.19 (d, 1H, J=2.1 Hz), 7.72 (t, 1H, J=1.6 Hz), 7.61 (dt, 1H, J=7.2, 1.6 Hz), 7.48-7.56 (m, 2H), 7.32 (d, 1H, J=2.3 Hz)

Example 4

Preparation of ethyl 2-[[5-(3-chlorophenyl)-3-hydroxypyridine-2-carbonyl]amino]acetate

[Chemical Formula 94]

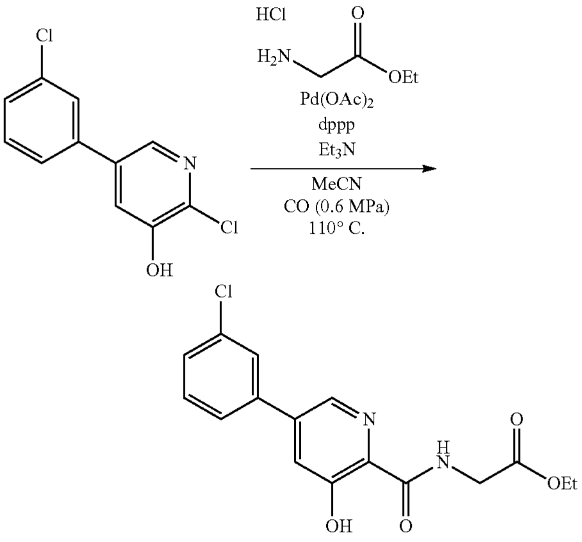

2-Chloro-5-(3-chlorophenyl)-3-hydroxypyridine (700.0 mg, 2.916 mmol), glycine ethyl ester hydrochloride salt (427.3 mg, 3.061 mmol), palladium acetate (20.5 mg, 0.087 mmol), 1,3-bis(diphenylphosphino)propane (72.7 mg, 0.175 mmol), triethylamine (1.22 mL, 8,747 mmol), and acetonitrile (35.0 mL) were added to a reactor vessel, and the atmosphere of the reaction system was purged with nitrogen and carbon monoxide successively, and pressurized with carbon monoxide at 0.6 MPa, and the resulting mixture was stirred at 110° C. for 72 hours while the pressure of the reaction system was maintained at 0.6 MPa. After the reaction mixture was concentrated under reduced pressure, acetonitrile (7.0 mL) and water (10.5 mL) were added thereto, and the mixture was stirred, and the precipitated crystals were collected through a filtration. These crystals were further dissolved into acetonitrile (3.5 mL) with heating, and ethanol (7 mL) was added thereto, and the precipitation was conducted. The resulting crystals were collected through a filtration and dried with heating under reduced pressure to obtain ethyl 2-[[5-(3-chlorophenyl)-3-hydroxypyridine-2-carbonyl]amino]acetate (229.9 mg) (Yield 23%).

Further the mother liquid recovered here was concentrated under reduced pressure, and the liquid was washed with a mixed suspension of acetonitrile (0.7 mL) and ethanol (6.3 mL), and collected through a filtration and dried under reduced pressure to obtain 2-[[5-(3-chlorophenyl)-3-hydroxypyridine-2-carbonyl]amino]ethyl acetate (333.5 mg). (Yield 34%).

$^1$H NMR (500 MHz, DMSO-d$_6$) δ 12.30 (s, 1H), 9.51 (t, 1H, J=6.1 Hz), 8.56 (d, 1H, J=2.0 Hz), 7.92-7.95 (m, 1H), 7.77-7.83 (m, 2H), 7.52-7.58 (m, 2H), 4.15 (q, 2H, J=7.1 Hz), 4.09 (d, 2H, J=6.3 Hz), 1.22 (t, 3H, J=7.1 Hz)

Example 5

Preparation of 2-[[5-(3-chlorophenyl)-3-hydroxypyridine-2-carbonyl]amino]ethyl acetate

[Chemical Formula 95]

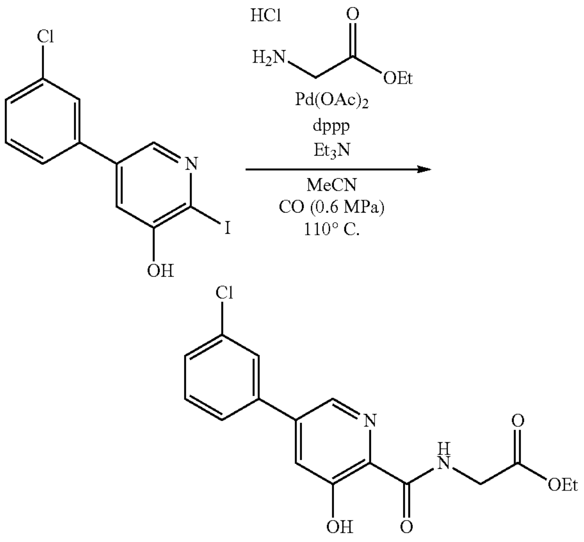

5-(3-Chlorophenyl)-3-hydroxy-2-iodopyridine (966.5 mg, 2.916 mmol), glycine ethyl ester hydrochloride salt (430.4 mg, 3.062 mmol), palladium acetate (19.7 mg, 0.087 mmol), 1,3-bis(diphenylphosphino)propane (71.5 mg, 0.175 mmol), triethylamine (1.22 mL, 8,748 mmol), and acetonitrile (35.0 mL) were added to a reactor vessel, and the atmosphere of the reaction system was purged with nitrogen and carbon monoxide successively, and pressurized with carbon monoxide at 0.6 MPa, and the resulting mixture was stirred at 110° C. for 24 hours while the pressure of the reaction system was maintained at 0.5 MPa. After the reaction mixture was concentrated under reduced pressure, ethyl acetate (15.0 mL) and water (10 mL) were added thereto, and the mixture was extracted, and organic layer and aqueous layer were separated. The organic layer obtained here was washed with water (7.0 mL) and the aqueous layer was washed with acetate (5.00 mL), and the organic layers were combined. The organic layer was concentrated under reduced pressure, and the concentrated residue was purified by column chromatography to obtain ethyl 2-[[5-(3-chlorophenyl)-3-hydroxypyridine-2-carbonyl]amino]acetate (herein, referred to as "Compound (a3-1-A)") (600.3 mg). (Yield 61%)

$^1$H NMR (500 MHz, DMSO-d$_6$) δ 12.30 (s, 1H), 9.50 (t, 1H, J=6.1 Hz), 8.55 (d, 1H, J=2.0 Hz), 7.92-7.95 (m, 1H), 7.77-7.83 (m, 2H), 7.52-7.58 (m, 2H), 4.15 (q, 2H, J=7.1 Hz), 4.09 (d, 2H, J=6.3 Hz), 1.22 (t, 3H, J=7.1 Hz)

Example 6

Preparation of 2-[[5-(3-chlorophenyl)-3-hydroxypyridine-2-carbonyl]amino]acetic acid

[Chemical Formula 96]

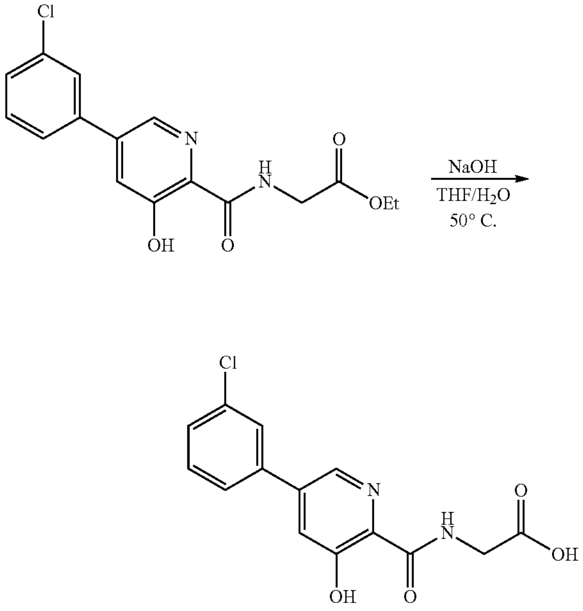

Ethyl 2-[[5-(3-chlorophenyl)-3-hydroxypyridine-2-carbonyl]amino]acetate (200.0 mg, 0.597 mmol), 1 mol/L aqueous sodium hydroxide solution (1.0 mL, 1.000 mmol), and tetrahydrofuran (1.0 mL) were added to a reactor vessel, and the mixture was stirred at 55° C. for 4.5 hours. 8 mol/L Aqueous sodium hydroxide solution (0.25 mL, 2.000 mmol) was supplemented, and the reaction was completed. 2 mol/L Hydrochloric acid (1.5 mL, 2.987 mmol) was added to the reaction mixture, and the solvent was concentrated under reduced pressure. 2 mol/L Aqueous sodium hydroxide solution and ethyl acetate were added to the residue, and a back-extraction was conducted, and 2 mol/L hydrochloric acid and ethyl acetate were added to the separated aqueous layer, and the extraction procedure was conducted. Sodium sulfate was added to the resulting organic layer, and the mixture was dehydrated and filtered, and the filtrates were concentrated under reduced pressure. The concentrated residue was dried with heating under reduced pressure to 2-[[5-(3-chlorophenyl)-3-hydroxypyridine-2-carbonyl]amino]acetic acid (151.3 mg). (Yield 82%)

$^1$H NMR (500 MHz, DMSO-d$_6$) δ 12.81 (br, 1H), 12.38 (s, 1H), 9.37 (t, 1H, J=12.2 Hz), 8.55 (s, 1H), 7.93 (s, 1H), 7.75-7.84 (m, 2H), 7.50-7.59 (m, 2H), 4.02 (d, 2H, J=12.2 Hz)

Example 7

Preparation of 2-[[5-(3-chlorophenyl)-3-hydroxy-pyridine-2-carbonyl]amino]acetic acid

[Chemical Formula 97]

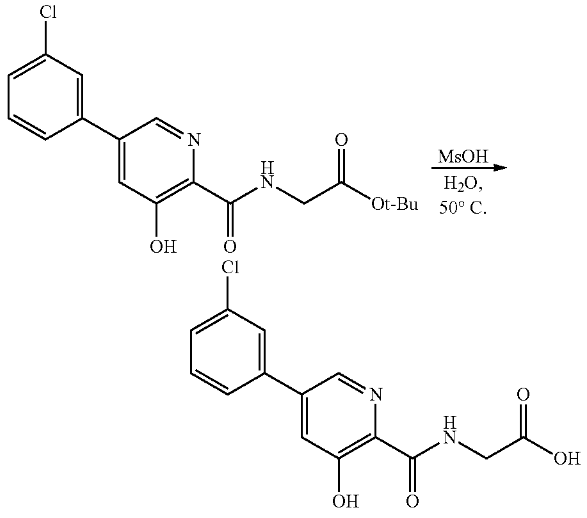

Tert-butyl 2-[[5-(3-chlorophenyl)-3-hydroxypyridine-2-carbonyl]amino]acetate (102.1 mg, 0.281 mmol), water (1.0 mL), and methanesulfonic acid (1.0 mL, 15 mmol) were added to reactor vessel, and the atmosphere of the reaction system was purged with nitrogen, and the mixture was then stirred at 50° C. for 15 hours. The progression of reaction was evaluated by HPLC to found that starting materials/desired products=0.4/95.0 (area percentage).

Example 8

Preparation of 2-[[5-(3-chlorophenyl)-3-hydroxy-pyridine-2-carbonyl]amino]acetic acid

[Chemical Formula 98]

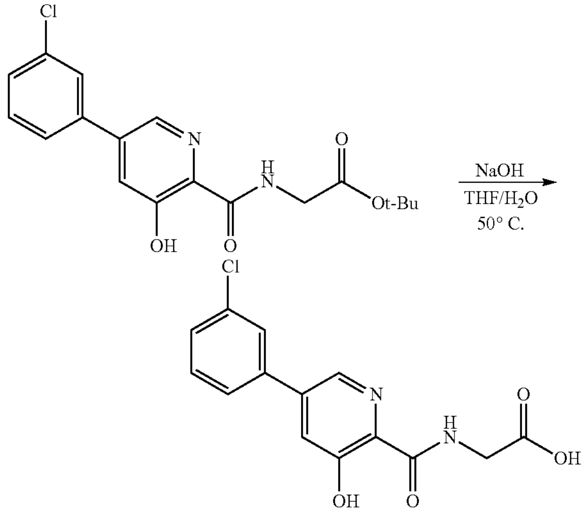

Tert-butyl 2-[[5-(3-chlorophenyl)-3-hydroxypyridine-2-carbonyl]amino]acetate (101.3 mg, 0.279 mmol), tetrahydrofuran (1.0 mL), and 1 mol/L sodium hydroxide (1.0 mL) were added to a reactor vessel, and the atmosphere of the reaction system was purged with nitrogen, and the mixture was then stirred at 50° C. four 15 hours. After the reaction mixture was cooled to a room temperature, 2 mol/L hydrochloric acid was added thereto, and the mixture was adjusted to pH 2, and the solvent was removed by concentration under reduced pressure.

The resulting residue was washed with water and hexane, and then dried with heating (50° C.) under reduced pressure to obtain 2-[[5-(3-chlorophenyl)-3-hydroxypyridine-2-carbonyl]amino]acetic acid (73.2 mg). (Yield 85%)

$^1H$ NMR (500 MHz, DMSO-$d_6$) δ 12.82 (br, 1H), 12.38 (s, 1H), 9.37 (t, 1H, J=12.2 Hz), 8.55 (s, 1H), 7.93 (s, 1H), 7.75-7.84 (m, 2H), 7.50-7.59 (m, 2H), 4.02 (d, 2H, J=12.2 Hz)

Example 9

Preparation of methyl 2-[(3,5-dichlopyridine-2-carbonyl)amino]acetate

[Chemical Formula 99]

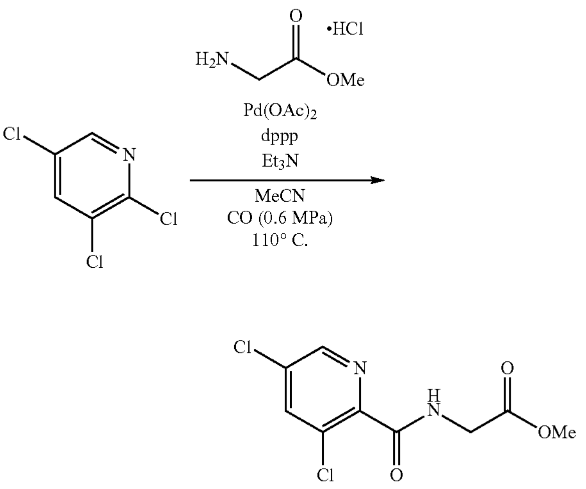

2,3,5-Trichloropyridine (2.09 g, 11.5 mmol), glycine methyl ester hydrochloride salt (1.73 g, 13.8 mmol), dppp (284.6 mg, 0.690 mmol), $Pd(OAc)_2$ (77.7 mg, 0.346 mmol), triethylamine (3.49 g, 34.5 mmol), and acetonitrile (21 mL) were added to a reactor vessel, and the atmosphere of the reaction system was purged with nitrogen and carbon monoxide successively, and pressurized with carbon monoxide at 0.6 MPa, and the resulting mixture was stirred at 110° C. for 12 hours while the pressure of the reaction system was maintained at 0.6 MPa. The reaction mixture was filtered under reduced pressure, and washed with acetonitrile (10 mL) A cake was suspended into acetonitrile (20 mL), and filtered again, and washed with acetonitrile (20 mL). These filtrates and the wash solutions were combined, and the mixtures were concentrated under reduced pressure. Acetonitrile (3 mL) was added to the concentrated residue, and the mixture was heated to 75° C. to dissolve the participated materials, and the mixture was stirred at room temperature, and then washed with water (11.5 mL), and further stirred at room temperature. The participated materials were filtered under reduced pressure, and washed with mixed solution of acetonitrile water=1:1 (3.0 mL) twice. The mixture was dried under reduced pressure to obtain methyl 2-[(3,5-dichloro pyridine-2-carbonyl)amino]acetate (1.90 g) as white powder. (Yield 63%)

$^1$H NMR (500 MHz, $CDCl_3$) δ 8.45 (d, 1H, J=2.0 Hz), 8.18 (s, 1H), 7.86 (d, 1H, J=2.1 Hz), 4.24 (d, 2H, J=5.5 Hz), 3.80 (s, 3H)

Example 10

Preparation of tert-butyl 2-[(3,5-dichloropyridine-2-carbonyl)amino]acetate

[Chemical Formula 100]

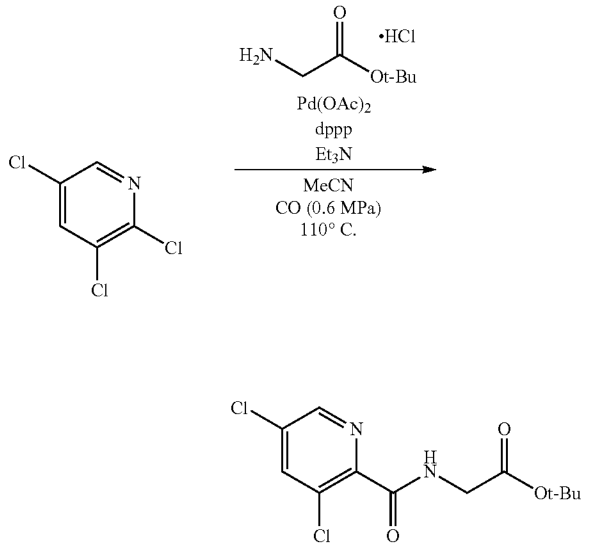

2,3,5-Trichloropyridine (2.62 g, 14.4 mmol), glycine tert-butyl ester hydrochloride salt (2.52 g, 15.1 mmol), dppp (355.3 mg, 0.861 mmol), $Pd(OAc)_2$ (96.9 mg, 0.432 mmol), triethylamine (4.36 g, 43.1 mmol), and acetonitrile (26 mL) were added to were added to a reactor vessel, and the atmosphere of the reaction system was purged with nitrogen and carbon monoxide successively, and pressurized with carbon monoxide at 0.6 MPa, and the resulting mixture was stirred at 110° C. for 12 hours. After the reaction mixture was concentrated under reduced pressure, a cake was washed with acetonitrile (26 mL). The filtrates and the wash solutions were combined, and the mixture was concentrated under reduced pressure to 10.4 g. Water (13 mL) was added thereto, and the mixture was stirred at room temperature. The precipitated materials were filtered under reduced pressure, and washed with mixed solution (6.5 mL) of acetonitrile water=1:1 twice. The mixture was concentrated under reduced pressure to obtain tert-butyl 2-[(3,5-dichloropyridine-2-carbonyl)amino]acetate (3.22 g). (Yield 74%)

$^1$H NMR (500 MHz, $CDCl_3$) δ 8.44 (d, 1H, J=2.1 Hz), 8.15 (s, 1H), 7.86 (d, 1H, J=2.1 Hz), 4.12 (d, 2H, J=5.3 Hz), 1.50 (s, 9H)

Example 11

Preparation of methyl 2-[(5-chloro-3-hydroxypyridine-2-carbonyl)amino]acetate

[Chemical Formula 101]

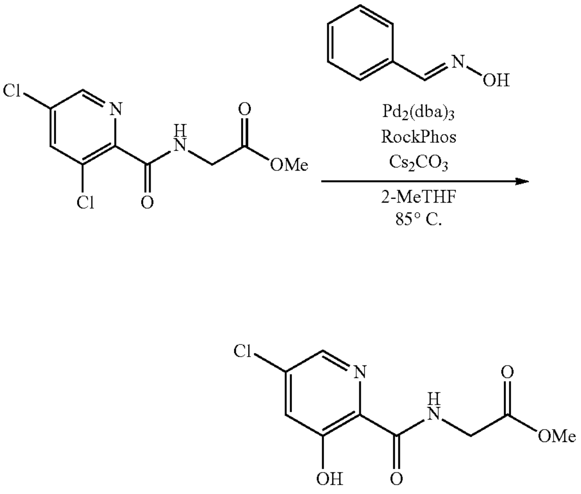

Methyl 2-[(3,5-dichloropyridine-2-carbonyl)amino]acetate (3.00 g, 11.4 mmol), $Pd_2$ $(dba)_3$ (313.2 mg, 0.3420 mmol), RockPhos (320.8 mg, 0.6844 mmol), cesium carbonate (8.18 g, 25.1 mmol), (E)-benzaldehyde oxime (1.80 g, 14.9 mmol), and 2-MeTHF (35 mL) were added to a reactor vessel, and the atmosphere of the reaction system was purged with nitrogen, and the mixture was then stirred at 85° C. for 20 hours. The reaction mixture was concentrated under reduced pressure, and water (75 mL) and chloroform (70 mL) were added to the concentrated residue, and the mixture was stirred at room temperature. The mixture was separated with a separatory funnel, and the aqueous layer was extracted with chloroform (70 mL) twice. The organic layers were combined, and sodium sulfate was added thereto, and the mixture was dehydrated, and filtered, and the filtrates were concentrated under reduced pressure. Methanol (25 mL) was added to the concentrated residue, and the mixture was stirred, and the precipitated materials were then filtered under reduced pressure, and washed with methanol (15 mL). The mixture was dried under reduced pressure to obtain methyl 2-[(5-chloro-3-hydroxypyridine-2-carbonyl)amino]acetate (807.8 mg) as a pale green solid. (Yield 29%)

$^1$H NMR (500 MHz, DMSO-$d_6$) δ 12.44 (br, 1H), 9.53 (brt, 1H, J=5.7 Hz), 8.25 (d, 1H, J=2.0 Hz), 7.70 (d, 1H, J=2.1 Hz), 4.08 (d, 2H, J=6.1 Hz), 3.67 (s, 3H)

Example 12

Preparation of tert-butyl 2-[(5-chloro-3-hydroxy-pyridine-2-carbonyl)amino]acetate

[Chemical Formula 102]

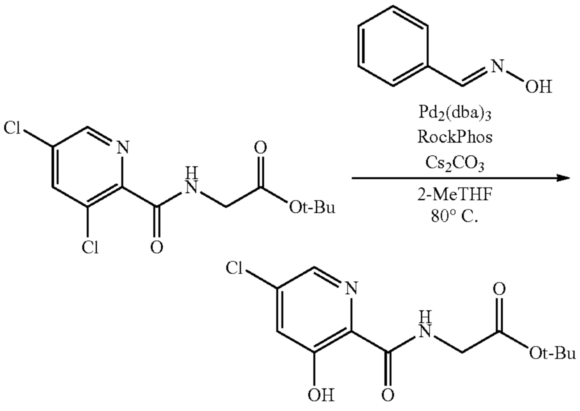

Tert-butyl 2-[(3,5-dichloropyridine-2-carbonyl)amino]acetate (2.99 g, 9.83 mmol), $Pd_2$ $(dba)_3$ (270.4 mg, 0.295 mmol), RockPhos (276.1 mg, 0.590 mmol), cesium carbonate (7.1 g, 21.6 mmol), (E)-benzaldehyde oxime (1.55 g, 12.8 mmol), and 2-MeTHF (20 mL) were added to a reactor vessel, and the atmosphere of the reaction system was purged with nitrogen, and the mixture was then stirred at 80° C. for 21 hours. The reaction mixture was cooled to room temperature, and the solid component was filtered. The solid component was dissolved by adding 2 mol/L hydrochloric acid (12 mL) and 2-MeTHF (20 mL), and the aqueous layer was separated, and the organic layer was then concentrated under reduced pressure. The solid concentrated residue was washed with n-heptane, and the mixture was dried under reduced pressure, and was further purified by a column chromatography to obtain tert-butyl 2-[(5-chloro-3-hydroxypyridine-2-carbonyl)amino]acetate (1.40 g) as a white solid (1.40 g). (Yield 50%)

$^1$H NMR (500 MHz, $CDCl_3$) δ 12.02 (s, 1H), 8.34-8.20 (brs, 1H), 8.03 (d, 1H, J=2.0 Hz), 7.33 (d, 1H, J=2.0 Hz), 4.12 (d, 2H, J=5.5 Hz), 1.51 (s, 9H)

Example 13

Preparation of tert-butyl 2-[(5-chloro-3-hydroxy-pyridine-2-carbonyl)amino]acetate

[Chemical Formula 103]

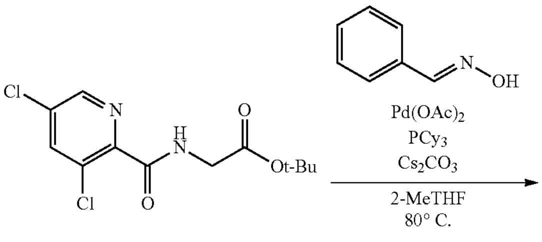

-continued

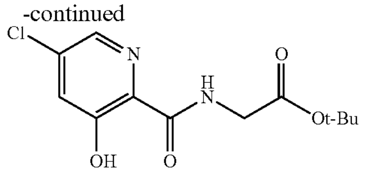

Tert-butyl 2-[(3,5-dichloropyridine-2-carbonyl)amino]acetate (6.00 g, 19.7 mmol), $Pd(OAc)_2$ (132.6 mg, 0.590 mmol), $PCy_3$ (331.1 mg, 1.180 mmol), cesium carbonate (14.1 g, 43.3 mmol), (E)-benzaldehyde oxime (3.10 g, 25.6 mmol), and 2-MeTHF (40 mL) were added to a reactor vessel, and the atmosphere of the reaction system was purged with nitrogen, and the mixture was then stirred at 80° C. for 21 hours. The reaction mixture was cooled to room temperature, and was filtered under reduced pressure, and the solid component was collected through filtration. 2 mol/L Hydrochloric acid (21.6 mL, 43.3 mmol) and ethyl acetate (40 mL) were added to the solid component, and the aqueous layer was separated, and the organic layer was then concentrated under reduced pressure. The concentrated residue was purified by column chromatography to obtain tert-butyl 2-[(5-chloro-3-hydroxypyridine-2-carbonyl)amino]acetate (4.45 g) as a white solid. (Yield 79%)

$^1$H NMR (500 MHz, DMSO-$d_6$) δ 12.51 (s, 1H), 9.41 (brt, 1H, J=6.0 Hz), 8.24 (d, 1H, J=2.1 Hz), 7.70 (d, 1H, J=2.1 Hz), 3.95 (d, 2H, J=6.3 Hz), 1.42 (s, 9H)

Example 14

Preparation of tert-butyl 2-[[5-(3-chlorophenyl)-3-hydroxypyridine-2-carbonyl]amino]acetate

[Chemical Formula 104]

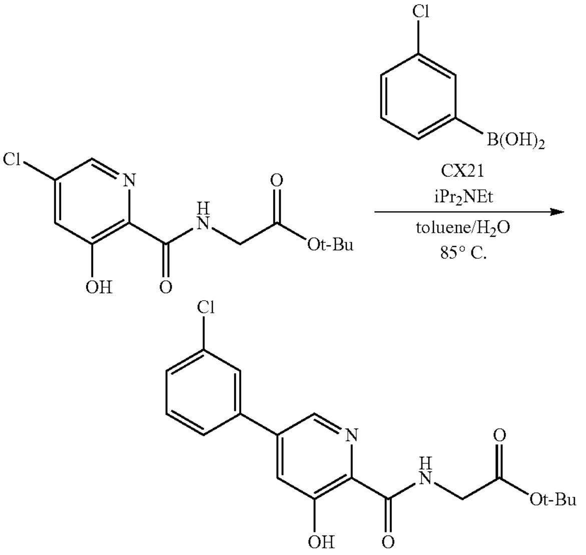

Tert-butyl 2-[(5-chloro-3-hydroxypyridine-2-carbonyl)amino]acetate (1.00 g, 3.50 mmol), CX21 (100.6 mg, 0.176 mmol), (3-chlorophenyl)boronic acid (572.4 mg, 3.66 mmol), toluene (5.0 mL), water (15 mL), and N,N-diisopropyl ethyl amine (1.26 g, 9.77 mmol) were added to a reactor vessel, and the atmosphere of the reaction system was purged with nitrogen, and the mixture was then stirred at 85° C. for 15 hours. After cooled to room temperature, the mixture was separated with a separatory funnel, and the aqueous layer was extracted with toluene (10 mL). The organic layers were combined, and sodium sulfate was added thereto, and the mixture was dehydrated and filtered, and then concentrated under reduced pressure. The concentrated residue was purified by a column chromatography. The concentrated residue was dissolved by adding ethyl acetate (500 μL), and washed with n-heptane (20 mL), and the precipitated materials were then collected through filtration. The mixture was dried under reduced pressure to obtain tert-butyl 2-[[5-(3-chlorophenyl)-3-hydroxypyridine-2-carbonyl]amino]acetate (462.3 mg). (Yield 36%)

$^1$H NMR (500 MHz, DMSO-$d_6$) δ 12.34 (s, 1H), 9.40, (t, 1H, J 6.2 Hz), 8.55 (d, 1H, J=1.9 Hz), 7.93 (s, 1H), 7.84-7.80 (m, 1H), 7.79 (d, 1H, J=2.0 Hz), 7.57-7.53 (m, 2H), 3.98 (d, 2H, J=6.2 Hz), 1.44 (s, 9H)

Example 15

Preparation of 2-[[5-(3-chlorophenyl)-3-hydroxypyridine-2-carbonyl]amino]acetic acid

[Chemical Formula 105]

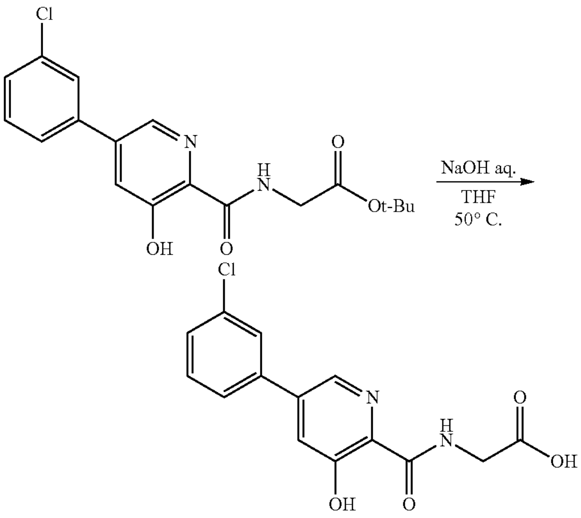

Tert-butyl 2-[[5-(3-chlorophenyl)-3-hydroxypyridine-2-carbonyl]amino]acetate (101.3 mg, 0.2792 mmol), 1 mol/L aqueous sodium hydroxide solution (1.0 mL, 1.0 mmol), and THE (1.0 mL) were added to a reactor vessel, and the mixture was stirred at 50° C. for 15 hours to progress the reaction. After cooled to room temperature, the mixture was adjusted with 2 mol/L hydrochloric acid (300 μL) to pH 2.0. This mixture was concentrated under reduced pressure at 35° C. as an outer bath temperature, and THF was removed. After the concentrated residue was stirred at room temperature for 30 minutes, the precipitated solid was filtered. The solids that were collected by filtration were washed with water (2.0 mL) and n-hexane (2.0 mL), and the mixture was dried under reduced pressure to obtain 2-[[5-(3-chlorophenyl)-3-hydroxypyridine-2-carbonyl]amino]acetic acid (73.2 mg). (Yield 86%)

$^1$H NMR (500 MHz, DMSO-$d_6$) δ 12.82 (brs, 1H), 12.38 (s, 1H), 9.37, (t, 1H, J=6.2 Hz), 8.55 (d, 1H, J=1.9 Hz), 7.95-7.92 (m, 1H), 7.83-7.80 (m, 1H), 7.79 (d, 1H, J=1.8 Hz), 7.56-7.53 (m, 2H), 4.02 (d, 2H, J=6.2 Hz)

Example 16

Preparation of methyl 2-[(3,5-dichloropyridine-2-carbonyl)amino]acetate

[Chemical Formula 106]

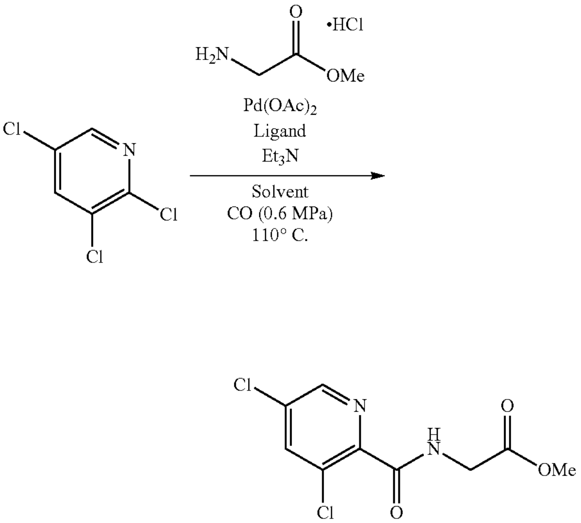

2,3,5-Trichloropyridine (700 mg, 3.84 mmol), glycine methyl ester hydrochloride salt (1.2 equivalents), a ligand (6.0 mol %), $Pd(OAc)_2$ (3.0 mol %), triethylamine (3.0 equivalents), and solvent (35 mL) were added to a reactor vessel, and the atmosphere of the reaction system was purged with nitrogen and carbon monoxide successively, and pressurized with carbon monoxide at 0.6 MPa, and the mixture was stirred at 110° C. for 5 hours while the pressure of the reaction system was maintained at 0.6 MPa. The progression of reaction was evaluated by HPLC and the results are shown in Table 1 below.

TABLE 1

| | | | HPLC measurement results [area %] | | |
|---|---|---|---|---|---|
| Run | Solvent | Ligand | Desired products | Starting materials | Others |
| 1 | toluene | Xantphos | 10.5 | 86.2 | 3.3 |
| 2 | DME | Xantphos | 12.0 | 83.7 | 4.4 |
| 3 | diglyme | Xantphos | 15.0 | 79.2 | 5.8 |
| 4 | anisole | Xantphos | 16.1 | 73.6 | 10.3 |
| 5 | DMF | Xantphos | 24.1 | 57.3 | 18.6 |
| 6 | MeCN | Xantphos | 20.1 | 74.3 | 5.6 |
| 7 | MeCN | dppf | 28.2 | 69.0 | 2.8 |
| 8 | MeCN | rac-BINAP | 30.5 | 64.9 | 4.6 |
| 9 | MeCN | dppp | 48.5 | 40.8 | 10.7 |

Example 17

Preparation of 2-[(3,5-dichloropyridine-2-carbonyl) amino]acetic acid

[Chemical Formula 107]

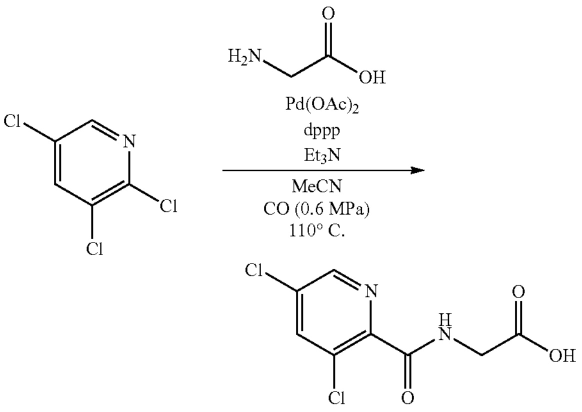

2,3,5-Trichloropyridine (2.62 g, 14.4 mmol), glycine (1.29 g, 17.2 mmol), dppp (355.2 mg, 0.861 mmol), $Pd(OAc)_2$ (97.0 mg, 0.432 mmol), triethylamine (4.36 g, 43.1 mmol), and acetonitrile (26 mL) were added to a reactor vessel, and the atmosphere of the reaction system was purged with nitrogen and carbon monoxide successively, and pressurized with carbon monoxide at 0.6 MPa, and the resulting mixture was stirred at 110° C. for 24 hours while the pressure of the reaction system was maintained at 0.6 MPa. The progression of reaction was evaluated by HPLC to found that starting materials/desired products=42.3/44.9 (area percentage).

Example 18

Preparation of ethyl 2-[(3,5-dichloropyridine-2-carbonyl)amino acetate

[Chemical Formula 108]

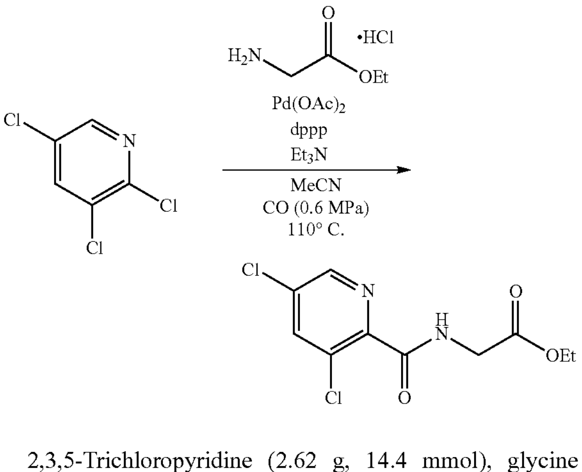

2,3,5-Trichloropyridine (2.62 g, 14.4 mmol), glycine ethyl ester hydrochloride salt (2.40 g, 17.2 mmol), dppp (355.3 mg, 0.861 mmol), $Pd(OAc)_2$ (96.9 mg, 0.432 mmol), triethylamine (4.36 g, 43.1 mmol), and acetonitrile (26 mL) were added to a reactor vessel, and the atmosphere of the reaction system was purged with nitrogen and carbon monoxide successively, and pressurized with carbon monoxide at 0.6 MPa, and the resulting mixture was stirred at 110° C. for 12 hours while the pressure of the reaction system was maintained at 0.6 MPa. The progression of reaction was evaluated by HPLC to found that starting materials/desired products=0.7/82.6 (area percentage).

Example 19

Preparation of tert-butyl 2-[(3-chloro-5-hydroxy-pyridine-2-carbonyl)amino]acetate

[Chemical Formula 109]

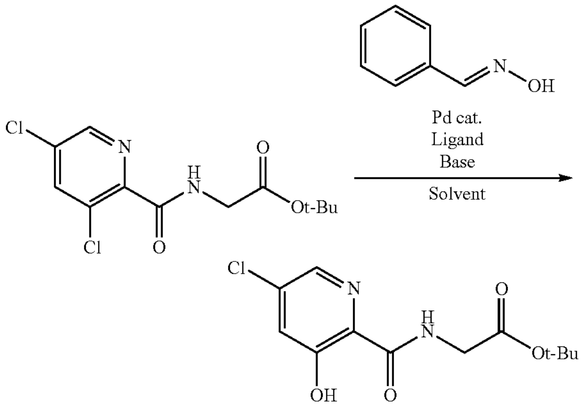

Method A

Tert-butyl 2-[(3,5-dichloropyridine-2-carbonyl)amino]acetate (100 mg, 0.328 mmol), Pd catalyst (5 mol %, 0.016 mmol), a ligand (10 mol %, 0.033 mmol), cesium carbonate (235 mg, 0.721 mmol), (E)-benzaldehyde oxime (49 μL, 0.426 mmol), and solvent (1.0 mL) were added to a reactor vessel, the atmosphere of the reaction system was purged with nitrogen, and the mixture was then stirred at 85° C. for 22 hours. The progression of reaction was evaluated by HPLC and the results are shown in Table 2 below.

Method B

Tert-butyl 2-[(3,5-dichloropyridine-2-carbonyl)amino]acetate (50.4 mg, 0.165 mmol), $Pd(OAc)_2$ (1.1 mg, 0.0049 mmol), $PCy_3$ (3.3 mg, 0.012 mmol), potassium carbonate (49.9 mg, 0.361 mmol), (E)-benzaldehyde oxime (25 μL, 0.213 mmol), and 2-MeTHF (0.33 mL) were added to a reactor vessel, and the atmosphere of the reaction system was purged with nitrogen, and the mixture was then stirred at 80° C. for 12 hours. The progression of reaction was evaluated by HPLC and the results are shown in Table 2 below.

Method C

Tert-butyl 2-[(3,5-dichloropyridine-2-carbonyl)amino]acetate (50.0 mg, 0.164 mmol), $Pd(OAc)_2$ (1.1 mg, 0.0049 mmol), $PCy_3$ (3.1 mg, 0.011 mmol), tripotassium phosphate (76.5 mg, 0.360 mmol), (E)-benzaldehyde oxime (25 μL, 0.213 mmol), and 2-MeTHF (0.33 mL) were added to a reactor vessel, and the atmosphere of the reaction system was purged with nitrogen, and the mixture was then stirred at 80° C. for 15 hours. The progression of reaction was evaluated by HPLC and the results are shown in Table 2 below.

TABLE 2

| Run | Method | Pd Catalyst, Ligand | Base | Solvent | Reaction Time [h] | HPLC Measurement Results [area %] Desired Product | Starting Material | Others |
|---|---|---|---|---|---|---|---|---|
| 1 | A | $Pd_2(dba)_3$, RockPhos | $Cs_2CO_3$ | DMF | 6 | 23.5 | 2.4 | 74.1 |
| | | | | | 22 | 21.6 | 2.4 | 76.0 |
| 2 | A | $Pd(OAc)_2$, RockPhos | $Cs_2CO_3$ | 2-MeTHF | 6 | 77.7 | 4.6 | 17.7 |
| | | | | | 22 | 81.2 | n.d. | 18.8 |
| 3 | A | $Pd(PPh_3)_4$ | $Cs_2CO_3$ | 2-MeTHF | 6 | 61.6 | 2.1 | 36.3 |
| | | | | | 22 | 62.5 | n.d. | 37.5 |
| 4 | A | $Pd_2(dba)_3$, $PCy_3$ | $Cs_2CO_3$ | 2-MeTHF | 6 | 62.7 | 2.6 | 34.7 |
| | | | | | 22 | 84.9 | n.d. | 15.1 |
| 5 | A | $Pd(OAc)_2$, $PCy_3$ | $Cs_2CO_3$ | 2-MeTHF | 6 | 76.8 | 1.5 | 21.7 |
| 6 | B | $Pd(OAc)_2$, $PCy_3$ | $K_2CO_3$ | 2-MeTHF | 15 | 22.3 | 33.4 | 44.3 |
| 7 | C | $Pd(OAc)_2$, $PCy_3$ | $K_3PO_4$ | 2-MeTHF | 15 | 57.2 | 11.6 | 31.2 |

Note:
In Table, "n.d." represents that no desired products were measured by HPLC.

Example 20

Preparation of tert-butyl 2-[[5-(3-chlorophenyl)-3-hydroxypyridine-2-carbonyl]amino]acetate

[Chemical Formula 110]

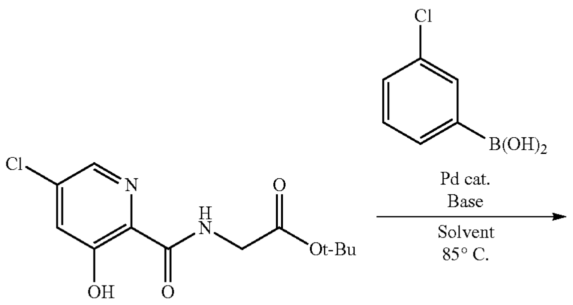

-continued

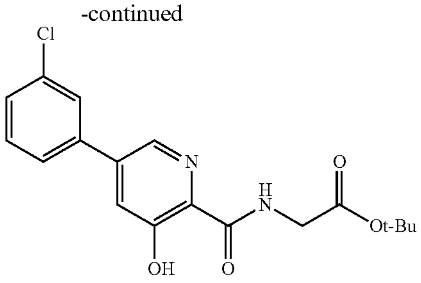

Tert-butyl 2-[(5-chloro-3-hydroxypyridine-2-carbonyl)amino]acetate (50 mg, 0.174 mmol), Pd catalyst (5 mol %), (3-chlorophenyl)boronic acid (38.2 mg, 0.244 mmol), solvent (1.0 mL), and a base (3.0 eq., 0.523 mmol) were added to a reactor vessel, and the atmosphere of the reaction system was purged with nitrogen, and the mixture was then stirred at 85° C. for 15 hours. The progression of reaction was evaluated by HPLC and the results are shown in Table 3 below.

TABLE 3

| Run | Pd Catalyst | Base | Solvent | HPLC Measurement Results[area %] Desired Product | Starting material | Others |
|---|---|---|---|---|---|---|
| 1 | $Pd(PPh)_4$ | $Na_2CO_3$ | $DME/H_2O$ = 3/1 | 19.4 | 35.8 | 44.8 |
| 2 | $Pd(dppf)Cl_2$ | $K_3PO_4$ | 1,4-dioxane | 12.5 | 77.0 | 10.5 |
| 3 | $Pd_2(dba)_3$, $PCy_3$ | $Cs_2CO_3$ | 1,4-dioxane | 11.2 | 75.3 | 13.5 |
| 4 | $P(tBu)_3PdG2$ | $Cs_2CO_3$ | 1,4-dioxane | 8.1 | 73.0 | 18.9 |
| 5 | $PdCl_2(amphos)_2$ | $K_2CO_3$ | $DME/H_2O$ = 3/1 | 12.1 | 74.9 | 13.0 |
| 6 | CX22 | $K_2CO_3$ | MeOH | 1.4 | 2.4 | 96.2 |
| 7 | CX22 | $Cs_2CO_3$ | MeOH | n.d. | 3.5 | 96.5 |
| 8 | CX22 | DBU | MeOH | n.d. | 2.2 | 97.8 |
| 9 | CX22 | t-BuOK | MeOH | 0.7 | 1.2 | 98.1 |
| 10 | CX22 | $iPr_2NEt$ | MeOH | 14.1 | 72.3 | 13.6 |
| 11 | CX22 | $iPr_2NEt$ | 2-PrOH | 0.4 | 90.2 | 9.4 |
| 12 | CX22 | $iPr_2NEt$ | t-BuOH | 6.0 | 84.0 | 10.0 |
| 13 | CX22 | $iPr_2NEt$ | $2-PrOH/H_2O$ = 3/1 | 2.8 | 82.3 | 14.9 |
| 14 | CX22 | $iPr_2NEt$ | $DMF/H_2O$ = 3/1 | n.d. | 94.1 | 5.9 |
| 15 | CX22 | $iPr_2NEt$ | $THF/H_2O$ = 3/1 | 1.1 | 91.5 | 7.4 |
| 16 | CX22 | $iPr_2NEt$ | $2-MeTHF/H_2O$ = 3/1 | 3.6 | 83.0 | 13.4 |

Note:
In Table, "n.d." represents that no desired products were measured by HPLC.

Example 21

Preparation of tert-butyl 2-[[5-(3-chlorophenyl)-3-hydroxypyridine-2-carbonyl]amino]acetate

[Chemical Formula 111]

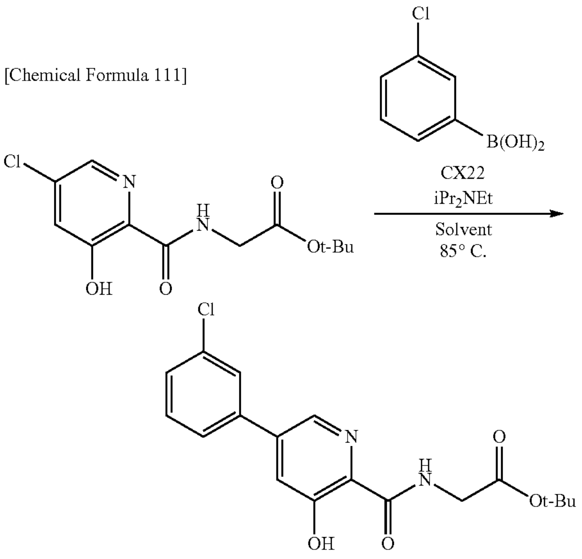

Tert-butyl 2-[(5-chloro-3-hydroxypyridine-2-carbonyl) amino]acetate (100 mg, 0.349 mmol), CX22 (8.5 mg, 0.017 mmol), (3-chlorophenyl)boronic acid (76.4 mg, 0.488 mmol), solvent (2.0 mL), and diisopropyl ethyl amine (0.30 mL, 1.744 mmol) were added to a reactor vessel, and the atmosphere of the reaction system was purged with nitrogen, and the mixture was stirred at 85° C. for 15 hours. The progression of reaction was evaluated by HPLC and the results are shown in Table 4 below.

TABLE 4

| | | HPLC Measurement Results [area %] | | |
|---|---|---|---|---|
| Run | Solvent | Desired Product | Starting Material | Others |
| 17 | $MeOH/H_2O$ = 3/1 | 23.2 | 67.7 | 9.1 |

Example 22

Preparation of tert-butyl 2-[[5-(3-chlorophenyl)-3-hydroxypyridine-2-carbonyl]amino]acetate

[Chemical Formula 112]

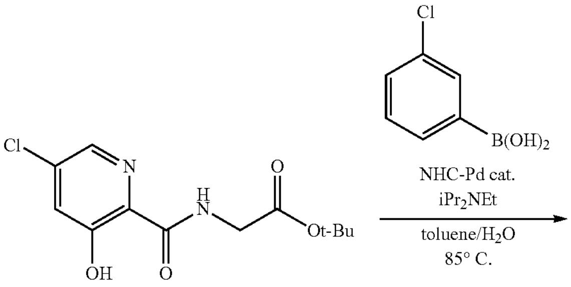

-continued

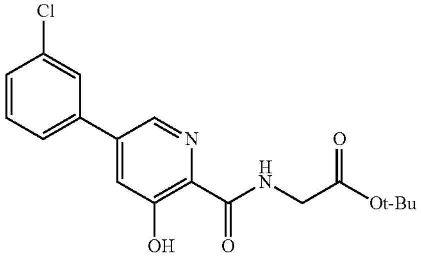

Tert-butyl 2-[(5-chloro-3-hydroxypyridine-2-carbonyl) amino]acetate (100 mg, 0.349 mmol), NHC—Pd cat. (5.0 mol %, 0.017 mmol), (3-chlorophenyl)boronic acid (76.4 mg, 0.488 mmol), solvent (2.0 mL), and diisopropyl ethyl amine (0.17 mL, 0.977 mmol) were added to a reactor vessel, and the atmosphere of the reaction system was purged with nitrogen, and the mixture was stirred at 85° C. for 15 hours. The progression of reaction was evaluated by HPLC and the results are shown in Table 5 below.

TABLE 5

| Run | NHC-Pd cat. | Constitute ratio of Solvent ($Toluene/H_2O$) | HPLC Measurement Results [area %] Desired Product | Starting Material | Others |
|---|---|---|---|---|---|
| 18 | CX22 | 3/1 | 50.0 | 36.3 | 13.7 |
| 19 | CX33 | 3/1 | 80.9 | 3.6 | 15.5 |
| 20 | CX31 | 3/1 | 68.6 | 15.5 | 15.9 |
| 21 | CX31 | 1/1 | 69.8 | 12.6 | 17.6 |
| 22 | CX31 | 1/3 | 66.1 | 4.9 | 29.0 |
| 23 | CX21 | 1/3 | 66.1 | 6.3 | 27.6 |

Example 23

Preparation of 2-chloro-5-(3-chlorophenyl)-3-hydroxypyridine

[Chemical Formula 113]

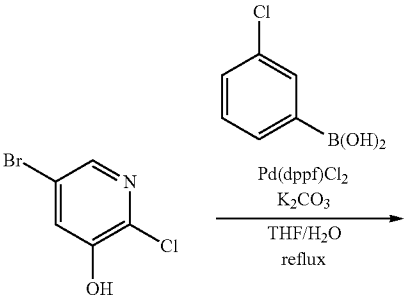

-continued

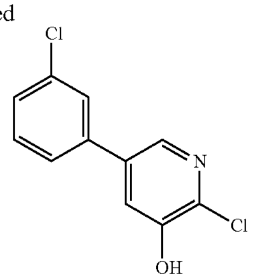

-continued

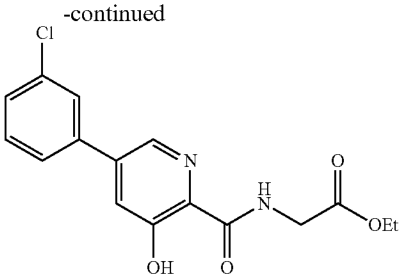

5-bromo-2-chloro-3-hydroxypyridine (7.00 g, 33.583 mmol), Pd(dppf)$Cl_2$ (36.8 mg, 0.050 mmol), (3-chloropheny)boronic acid (6.30 g, 40.286 mmol), potassium carbonate (6.96 g, 50.358 mmol), tetrahydrofuran (28.0 mL), and water (23.2 mL) were added to a reactor vessel, and the mixture was stirred under reflux under nitrogen atmosphere for 20 hours. The reaction mixture was warmed to 40° C., and water (42.0 mL) and sodium chloride (14.0 g) were added thereto, and the mixture was separated with a separatory funnel to remove the lower layer. Toluene (35.0 mL), water (21.0 mL), and tripotassium phosphate (7.00 g) were added to the mixture, and the mixture was stirred at room temperature, and then separated with a separatory funnel and the lower layer was collected. Water (14.0 mL) and tripotassium phosphate (1.40 g) were added to the upper layer, and the mixture was stirred at room temperature, and separated with a separatory funnel, and the upper layer was removed. The lower layers were combined, and thereto was added sodium chloride (7.00 g), and the mixture was stirred at room temperature, and then separated with a separatory funnel, and the lower layer was removed. The mixture was warmed to 40° C., and water (56.0 mL) was added thereto, and concentrated hydrochloric acid (3.85 g) was added dropwise thereto, and the mixture was cooled to 20° C. The precipitated solid was filtered under reduced pressure, and washed with mixed solution of tetrahydrofuran (3.5 mL) and water (28.0 mL). The mixture was dried under reduced pressure to obtain 2-chloro-5-(3-chlorophenyl)-3-hydroxypyridine (7.34 g). (Yield 91%)

$^1H$ NMR (500 MHz, DMSO-$d_6$) δ 10.93 (s, 1H), 8.21 (d, 1H, J=2.3 Hz), 7.74 (t, 1H, J=1.6 Hz), 7.62 (dt, 1H, J=7.4, 1.7 Hz), 7.48-7.55 (m, 3H)

Example 24

Preparation of ethyl 2-[[5-(3-chlorophenyl)-3-hydroxypyridine-2-carbonyl]amino]acetate

[Chemical Formula 114]

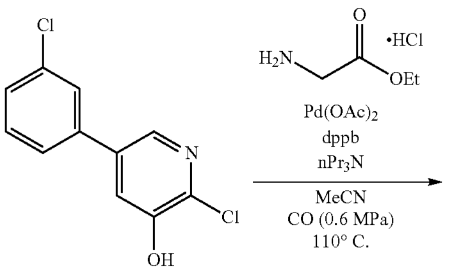

2-Chloro-5-(3-chlorophenyl)-3-hydroxypyridine (2.50 g, 10.413 mmol), glycine ethyl ester hydrochloride salt (1.53 g, 10.961 mmol), palladium acetate (5.8 mg, 0.026 mmol), 1,4-bis(diphenylphosphino)butane (22.3 mg, 0.052 mmol), tripropylamine (4.48 g, 31.270 mmol), and acetonitrile (30.0 mL) were added to a reactor vessel, and the atmosphere of the reaction system was purged with nitrogen and carbon monoxide successively, and pressurized with carbon monoxide at 0.6 MPa while the pressure of the reaction system was maintained at 0.6 MPa, and the mixture was stirred at 110° C. for 46 hours. The reaction mixture was filtered to remove the solid materials, and washed with acetonitrile (20 mL). The filtrates were concentrated under reduced pressure to 10 mL, and isopropanol (15 mL) was added thereto, and the mixture was heated to be a homogenous solution. After water (10 mL) was added dropwise thereto, the mixture was cooled to 20° C. The precipitated solid was filtered under reduced pressure, and washed with mixed solution of isopropanol (7.5 mL) and water (5 mL). The mixture was dried under reduced pressure to obtain a crude crystal of ethyl 2-[[5-(3-chlorophenyl)-3-hydroxypyridine-2-carbonyl]amino]acetate (2.80 g). (Yield 80%)

Example 25

Purification of ethyl 2-[[5-(3-chlorophenyl)-3-hydroxypyridine-2-carbonyl]amino]acetate

[Chemical Formula 115]

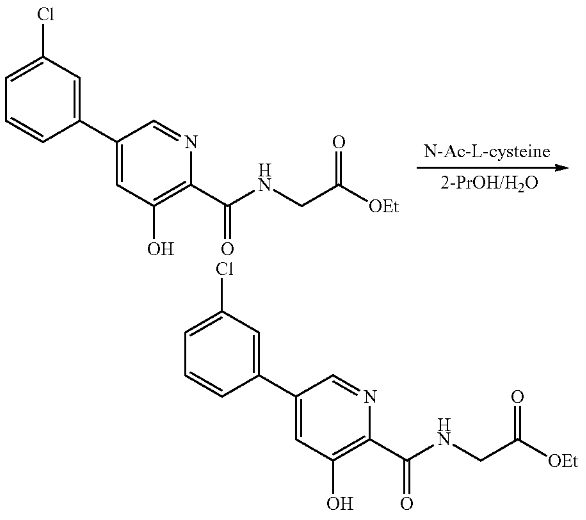

The crude crystal of ethyl 2-[[5-(3-chlorophenyl)-3-hydroxypyridine-2-carbonyl]amino]acetate (5.00 g, 14.936 mmol), N-acetyl L-cysteine (24.4 mg, 0.150 mmol), and mixed solution of isopropanol (35.0 mL) and water (15.0 mL) were added to a reactor vessel, and after the suspension was stirred at 56° C. for 2 hours, the mixture was cooled to 20° C. The solid component was filtered under reduced pressure, and washed with mixed solution of isopropanol (14 mL) and water (6 mL). The mixture was dried under reduced pressure to obtain ethyl 2-[[5-(3-chlorophenyl)-3-hydroxypyridine-2-carbonyl]amino]acetate (4.77 g). (Yield 95%)

$^1$H NMR (500 MHz, DMSO-$d_6$) δ12.30 (s, 1H), 9.50 (t, 1H, J=6.4 Hz), 8.56 (d, 1H, J=2.0 Hz), 7.92-7.95 (m, 1H), 7.77-7.83 (m, 2H), 7.52-7.58 (m, 2H), 4.15 (q, 2H, J=7.1 Hz), 4.09 (d, 2H, J=6.1 Hz), 1.22 (t, 3H, J=7.1 Hz)

Example 26

Preparation of 2-[[5-(3-chlorophenyl)-3-hydroxy-pyridine-2-carbonyl]amino]acetic acid

[Chemical Formula 116]

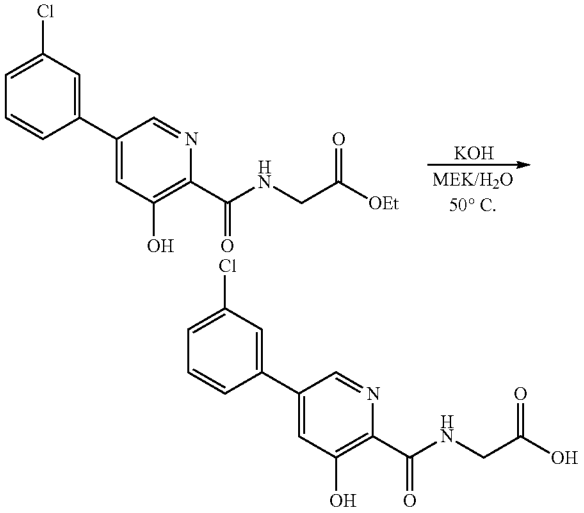

Ethyl 2-[[5-(3-chlorophenyl)-3-hydroxypyridine-2-carbonyl]amino]acetate (1.50 g, 4.481 mmol), methyl ethyl ketone (7.5 mL), and activated carbon (75.7 mg) were added to a reactor vessel, and after the mixture was stirred at 50° C. for 2 hours under nitrogen atmosphere, the solid materials were separated by filtration, and washed with methyl ethyl ketone (6.0 mL) to collect filtrates. The resulting mixture was dissolved by adding potassium hydroxide (638.9 mg, 11.201 mmol) and water (6.0 mL), and the above-mentioned filtrates were transferred with methyl ethyl ketone (1.5 mL), and the mixture was stirred at 50° C. for 2 hours to progress the reaction. The reaction mixture was separated with a separatory funnel to remove the upper layer, and tert-butanol (3.75 mL) was added at 40° C. thereto. A solution of 86% Phosphoric acid (1.54 g, 13.441 mmol), sodium chloride (601.1 mg), and water (1.8 mL) was added dropwise to the mixture, and the resulting mixture was stirred at 40° C. for 30 minutes. The mixture was separated with a separatory funnel to remove the lower layer, and water (10.5 mL) was added to the mixture to precipitate the crystal, and the resulting mixture was stirred at 40° C. four 1 hour, and cooled to 5° C. The precipitated materials were filtered under reduced pressure, and washed with mixed solution of tert-butanol (0.75 mL) and water (6.75 mL). The mixture was dried under reduced pressure to obtain 2-[[5-(3-chloro-pheny)-3-hydroxypyridine-2-carbonyl]amino]acetic acid (1.28 g). (Yield 93%)

$^1$H NMR (500 MHz, DMSO-$d_6$) δ12.82 (br, 1H), 12.38 (s, 1H), 9.38 (t, 1H, J=6.1 Hz), 8.55 (d, 1H, J=1.83 Hz), 7.92-7.95 (m, 1H), 7.77-7.83 (m, 2H), 7.52-7.58 (m, 2H), 4.02 (d, 2H, J=6.3 Hz)

Example 27

Preparation of Protected 5-bromo-2-chloro-3-hydroxypyridine

[Chemical Formula 117]

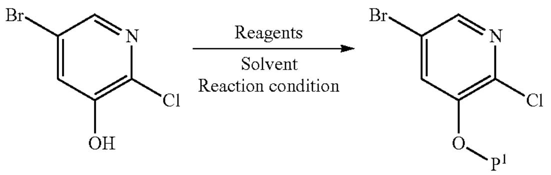

5-Bromo-2-chloro-3-hydroxypyridine and the reagents and solvents indicated in Table 6 below were added to a reactor vessel, and the reaction was conducted under the reaction condition shown in Table 6 below while supplementing reagents appropriately. After worked up, the resulting mixture was purified by a silica gel column chromatography to isolate a protected 5-bromo-2-chloro-3-hydroxypyridine. The yield amounts, yield percentages, and MS measurement are shown in Table 7 below.

TABLE 6

| Run | $P^1$ | 5-brmo-2-chloro-3-hydroxy pyridine | Reagents, Solvents | Reaction Condition |
|---|---|---|---|---|
| 1 | Ac | 201 mg,<br>0.96 mmol | $Et_3N$ (228 μL, 1.64 mmol)<br>$Ac_2O$ (108 μL, 1.14 mmol)<br>THF (1 L) | Reflux at heating,<br>15 hrs. |
| 2 | Piv | 303 mg,<br>1.45 mmol | Pyridine (3 mL)<br>PivCl (210 μL, 1.72 mmol) | Cool with ice water<br>bath, 1 hr. |
| 3 | MOM | 301 mg,<br>1.45 mmol | Acetone (5 mL)<br>$K_2CO_3$ (303 mg, 2.19 mmol)<br>MOMCl (131 μL, 1.72 mmol) | bath temperature<br>60° C., 3 hrs. |
| | | | MOMCl (26 μL, 0.34 mmol) | bath temperature<br>60° C., 1 hr. |

TABLE 6-continued

| Run | $P^1$ | 5-brmo-2-chloro-3-hydroxy pyridine | Reagents, Solvents | Reaction Condition |
|---|---|---|---|---|
| 4 | SEM | 300 mg, 1.44 mmol | t-BuOK (175 mg, 1.56 mmol)<br>THF (2 mL) DMF (2 mL)<br>SEMCl (253 μL, 1.44 mmol)<br>t-BuOK (175 mg, 1.56 mmol)<br>SEMCl (253 μL, 1.44 mmol) | Cool with ice bath, 1 hr.<br>r.t., 2 hrs.<br>Cool with ice water bath, 1 hr. |
| 5 | Ts | 296 mg, 1.42 mmol | Acetone (5 mL)<br>$K_2CO_3$ (305 mg, 2.21 mmol)<br>TsCl (333 mg, 1.75 mmol) | bath temperature 60° C., 2 hrs. |
| 6 | Ms | 300 mg, 1.44 mmol | Acetone (5 mL)<br>$K_2CO_3$ (301 mg, 2.18 mmol)<br>MsCl (134 μL, 1.73 mmol) | bath temperature 60° C., 2 hrs. |
| 7 | Cbz | 301 mg, 1.45 mmol | THF (3 mL)<br>1 mol/L NaOH aq. (2.2 mL, 2.2 mmol)<br>CbzCl (297 mg, 1.74 mmol)<br>1 mol/L NaOH aq. (2.2 mL, 2.2 mmol)<br>CbzCl (303 mg, 1.78 mmol)<br>THF (0.5 mL) | r.t., 5 hrs.<br>r.t., 17 hrs. |
| 8 | Boc | 302 mg, 1.45 mmol | $Boc_2O$ (410 mg, 1.88 mmol)<br>DMAP (18.8 mg, 0.15 mmol)<br>$Et_3N$ (221 μL, 1.59 mmol)<br>THF (4 mL)<br>$Boc_2O$ (198 mg, 0.91 mmol)<br>$Et_3N$ (121 μL, 0.87 mmol) | r.t., 25 hrs.<br>r.t., 6 hrs. |
| 9 | Bn | 302 mg, 1.45 mmol | Acetone (5 mL)<br>$K_2CO_3$ (301 mg, 2.18 mmol)<br>BnBr (205 μL, 1.73 mmol) | bath temperature 60° C., 2.5 hrs. |
| 10 | PMB | 300 mg, 1.44 mmol | Acetone (5 mL)<br>$K_2CO_3$ (295 mg, 2.13 mmol)<br>KI (27.6 mg, 0.17 mmol)<br>PMBCl (235 μL, 1.73 mmol) | bath temperature 60° C., 2 hrs. |
| 11 | Me | 401 mg, 1.92 mmol | Acetone (6.7 mL)<br>$K_2CO_3$ (399 mg, 2.89 mmol)<br>MeI (143 μL, 2.30 mmol)<br>MeI (60 μL, 0.96 mmol) | r.t., 8 hrs.<br>r.t., 18 hrs. |
| 12 | $Me_2NCO$ | 297 mg, 1.43 mmol | Pyridine (3 mL)<br>$Me_2NCOCl$ (159 μL, 1.73 mmol) | Cool with ice water bath, 1.5 hrs.,<br>r.t., 3.5 hrs |
| 13 | MePhNCO | 300 mg, 1.44 mmol | Pyridine (3 mL)<br>MePhNCOCl (294 mg, 1.74 mmol) | Cool with ice water bath, 1 hr.,<br>r.t., 1 hr. |

TABLE 7

| Run | $P^1$ | Yields | Yield Percentages | MS Measurement Result |
|---|---|---|---|---|
| 1 | Ac | 222 mg | 93% | m/z = 249.90 |
| 2 | Piv | 388 mg | 92% | m/z = 292.36 |
| 3 | MOM | 336 mg | 92% | m/z = 252.36 |
| 4 | SEM | 496 mg | quant. | m/z = 338.23 |
| 5 | Ts | 503 mg | 98% | m/z = 362.24 |
| 6 | Ms | 370 mg | 90% | m/z = 286.29 |
| 7 | Cbz | 413 mg | 77% | m/z = 342.23 |
| 8 | Boc | 350 mg | 79% | m/z = 308.05 |
| 9 | Bn | 412 mg | 97% | m/z = 298.03 |
| 10 | PMB | 436 mg | 92% | m/z = 328.23 |
| 11 | Me | 345 mg | 81% | m/z = 222.37 |
| 12 | $Me_2NCO$ | 383 mg | 96% | m/z = 279.41 |
| 13 | MePhNCO | 490 mg | 99% | m/z = 341.19 |

Example 28

Preparation of Protected 5-(3-chlorophenyl)-2-chloro-3-hydroxypyridine

[Chemical Formula 118]

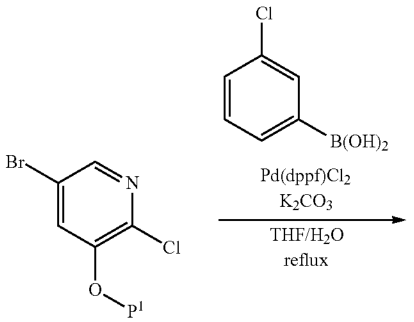

-continued

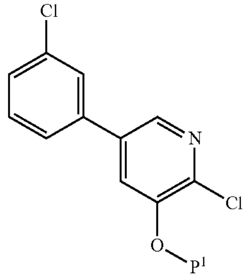

The protected 5-bromo-2-chloro-3-hydroxypyridine, (3-chlorophenyl)boronic acid, solvent, Pd(dppf)$Cl_2$ (0.03 equivalent amounts relative to the protected 5-bromo-2-chloro-3-hydroxypyridine), potassium carbonate (1.2 equivalent amounts relative to the protected 5-bromo-2-chloro-3-hydroxypyridine) each in the amounts shown in Table 8 below were added to a reactor vessel, and the mixture was stirred appropriately under reflux at heating under nitrogen atmosphere, and the reaction was conducted for the time shown in Table 8 below while supplementing (3-chloropheny)boronic acid. After worked up, the resulting mixture was purified by silica gel column chromatography to isolate the protected 5-(3-chlorophenyl)-2-chloro-3-hydroxypyridine. The yield amounts, yield percentages, and MS measurement results were shown in Table 9 below.

TABLE 8

| Run | $P^1$ | Protected 5-bromo-2-chloro-3-hydroypyridine | (3-Chlorophenyl) boronic acid | Solvent | Reaction Time |
|---|---|---|---|---|---|
| 1 | Ac | 222 mg, 0.89 mmol | 151 mg, 0.96 mmol | THF (1.2 mL) | 3 hrs. |
| | | | | Water (0.6 mL) | |
| 2 | Piv | 388 mg, 1.33 mmol | 218 mg, 1.39 mmol | THF (1.8 mL) | 3.5 hrs. |
| | | | 42 mg, 0.27 mmol | Water (0.9 mL) | 1.5 hrs. |
| 3 | MOM | 336 mg, 1.33 mmol | 261 mg, 1.67 mmol | THF (1.8 mL) | 18.5 hrs. |
| | | | | Water (0.9 mL) | |
| 4 | SEM | 496 mg, 1.44 mmol | 228 mg, 1.46 mmol | THF (2.0 mL) | 4 hrs. |
| | | | 23 mg, 0.14 mmol | Water (1.0 mL) | 2 hrs. |
| 5 | Ts | 503 mg, 1.39 mmol | 242 mg, 1.64 mmol | THF (2.0 mL) | 3 hrs. |
| | | | | Water (1.0 mL) | |
| 6 | Ms | 370 mg, 1.29 mmol | 224 mg, 1.43 mmol | THF (1.86 mL) | 4 hrs. |
| | | | | Water (0.93 mL) | |
| 7 | Cbz | 380 mg, 1.11 mmol | 193 mg, 1.24 mmol | THF (1.6 mL) | 3 hrs. |
| | | | | Water (0.8 mL) | |
| 8 | Boc | 350 mg, 1.14 mmol | 197 mg, 1.26 mmol | THF (1.64 mL) | 3 hrs. |
| | | | | Water (0.82 mL) | |
| 9 | Bn | 421 mg, 1.41 mmol | 243 mg, 1.55 mmol | THF (2.0 mL) | 4 hrs. |
| | | | | Water (1.0 mL) | |
| 10 | PMB | 436 mg, 1.33 mmol | 229 mg, 1.46 mmol | THF (1.9 mL) | 22.5 hrs. |
| | | | | Water (0.945 mL) | |
| 11 | Me | 345 mg, 1.55 mmol | 268 mg, 1.72 mmol | THF (2.2 mL) | 7 hrs. |
| | | | | Water (1.1 mL) | |
| 12 | $Me_2NCO$ | 382 mg, 1.37 mmol | 236 mg, 1.51 mmol | THF (1.8 mL) | 4 hrs. |
| | | | | Water (0.945 mL) | |
| 13 | MePhNCO | 485 mg, 1.42 mmol | 246 mg, 1.57 mmol | THF (2.0 mL) | 5 hrs. |
| | | | | Water (1.0 mL) | |

TABLE 9

| Run | $P^1$ | Yields | Yield percentages | MS Measurement Results |
|---|---|---|---|---|
| 1 | Ac | 196 mg | 79% | m/z = 282.03 |
| 2 | Piv | 417 mg | 96% | m/z = 324.36 |
| 3 | MOM | 374 mg | 99% | m/z = 284.36 |
| 4 | SEM | 470 mg | 88% | m/z = 370.30 |
| 5 | Ts | 486 mg | 89% | m/z = 394.25 |
| 6 | Ms | 422 mg | 97% | m/z = 318.23 |
| 7 | Cbz | 309 mg | 69% | m/z = 374.33 |
| 8 | Boc | 360 mg | 93% | m/z = 340.12 |
| 9 | Bn | 447 mg | 96% | m/z = 330.12 |
| 10 | PMB | 452 mg | 95% | m/z = 360.38 |
| 11 | Me | 378 mg | 96% | m/z = 254.44 |
| 12 | $Me_2NCO$ | 451 mg | quant. | m/z = 311.36 |
| 13 | MePhNCO | 547 mg | 98% | m/z = 373.05 |

Example 29

Preparation of ethyl [[3-benzyloxy-5-(3-chlorophenyl)pyridine-2-carbonyl]amino]acetate

[Chemical Formula 119]

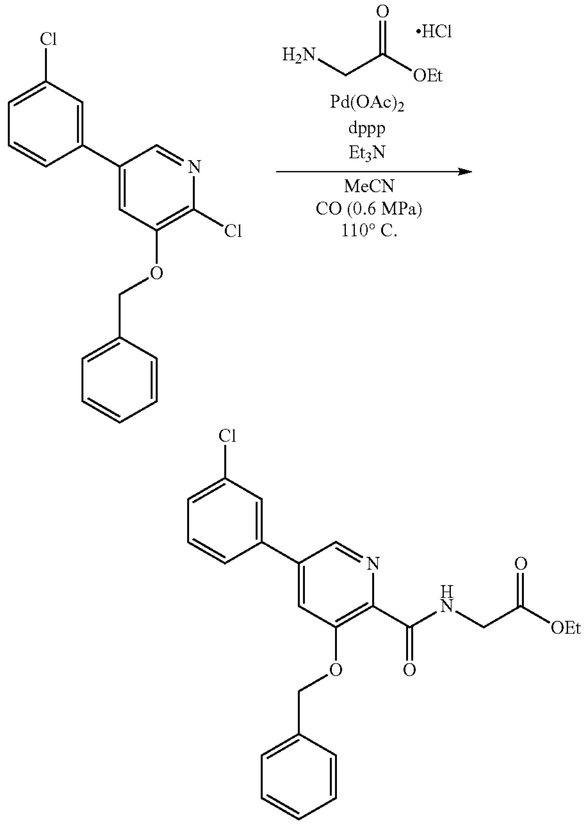

3-(Benzyloxy)-2-chloro-5-(3-chlorophenyl)pyridine (200 mg, 0.61 mmol), acetonitrile (3 mL), glycine ethyl ester hydrochloride salt (95 mg, 0.68 mmol), triethylamine (255 μL, 1.83 mmol), 1,3-bis(diphenylphosphino)propane (14.7 mg, 0.03 mmol), and palladium acetate (5.0 mg, 0.02 mmol) were added to a reactor vessel, and the atmosphere of the reaction system was purged with nitrogen and carbon monoxide successively, and pressurized with carbon monoxide at 0.6 MPa while the pressure of the reaction system was maintained at 0.6 MPa, and the mixture was stirred at 110° C. for 23 hours. Ethyl acetate was added thereto and the precipitated solid was separated by filtration, and washed with ethyl acetate. The filtrates were concentrated and the resulting residue was purified by a silica gel column chromatography to obtain ethyl 2-[[3-benzyloxy-5-(3-chlorophenyl)pyridine-2-carbonyl]amino]acetate (209 mg). (Yield 75%)

$^1$H NMR ($CDCl_3$) δ: 1.31 (3H, t, J=7.2 Hz), 4.22-4.28 (4H, m), 5.34 (2H, s), 7.32-7.35 (1H, m), 7.39-7.43 (5H, m), 7.48-7.50 (2H, m), 7.53-7.55 (2H, m), 8.31 (1H, t, J=4.8 Hz), 8.43 (1H, d, J=1.6 Hz).

Example 30

Preparation of ethyl 2-[[5-(3-chlorophenyl)-3-[(4-methoxyphenyl)methoxy]pyridine-2-carbonyl]amino]acetate

[Chemical Formula 120]

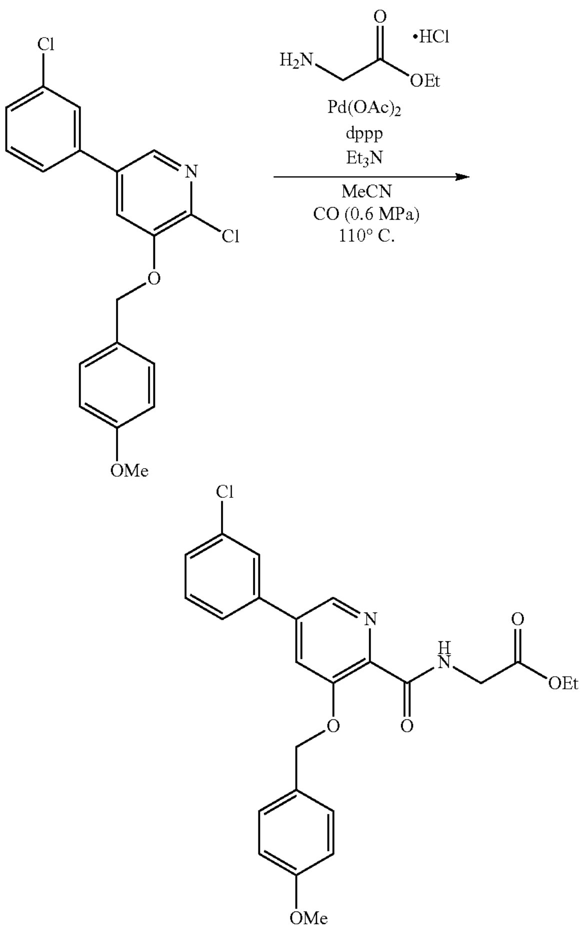

2-Chloro-5-(3-chlorophenyl)-3-[(4-methoxyphenyl)methoxy]pyridine (201 mg, 0.56 mmol), acetonitrile (3.0 mL), glycine ethyl ester hydrochloride salt (88 mg, 0.64 mmol), triethylamine (234 μL, 1.68 mmol), 1,3-bis(diphenylphosphino)propane (15.0 mg, 0.04 mmol), and palladium acetate (4.2 mg, 0.02 mmol) were added to a reactor vessel, and the atmosphere of the reaction system was purged with nitrogen and carbon monoxide successively, and pressurized with carbon monoxide at 0.6 MPa while the pressure of the reaction system was maintained at 0.6 MPa, and the mixture was stirred at 110° C. for 15 hours. Ethyl acetate was added thereto and the precipitated solid was separated by filtration, and washed with ethyl acetate. The filtrates were concentrated and the resulting residue was purified by a silica gel column chromatography to obtain ethyl 2-[[5-(3-chlorophenyl)-3-[(4-methoxyphenyl)methoxy]pyridine-2-carbonyl]amino]acetate (191 mg). (Yield 73%)

$^1$H NMR ($CDCl_3$) δ: 1.30 (3H, t, J=7.2 Hz), 3.81 (3H, s), 4.18-4.27 (4H, m), 5.27 (2H, s), 6.93 (2H, d, J=8.8 Hz), 7.41-7.51 (7H, m), 8.30 (1H, t, J=5.2 Hz), 8.43 (1H, d, J=2.0 Hz).

Example 31

Preparation of 2-[[5-(3-chlorophenyl)-3-hydroxypyridine-2-carbonyl]amino]acetic acid

[Chemical Formula 121]

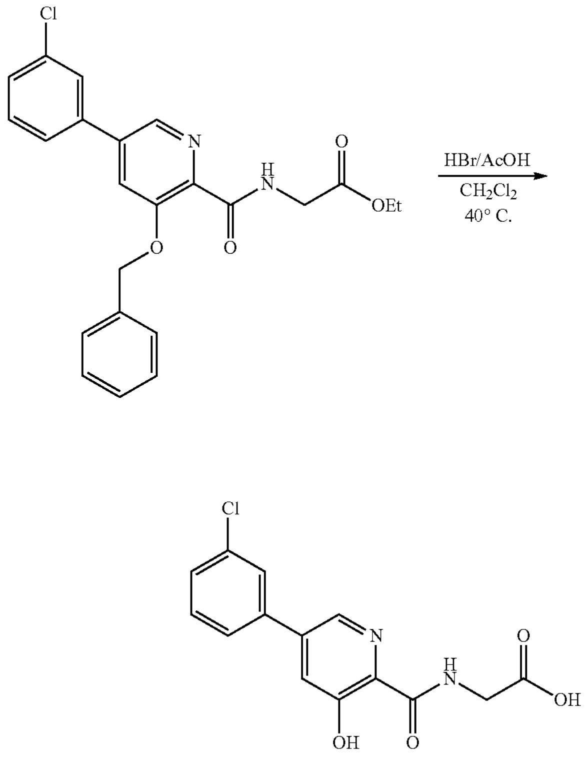

Ethyl 2-[[3-benzyloxy-5-(3-chlorophenyl)pyridine-2-carbonyl]amino]acetate (170 mg, 0.40 mmol), dichloromethane (5 mL), hydrogen bromide (30% acetic solution) (1 mL) were added to a reactor vessel, and the mixture was stirred at 40° C. for 24 hours. The reaction mixture was cooled under ice-cooling, and thereto was added water, and the mixture was extracted with dichloromethane three times. The organic layers were combined, and dried over sodium sulfate, and the solid was then separated by filtration. The filtrates were concentrated under reduced pressure, and thereto was further added toluene, and the resulting mixture was concentrated under reduced pressure again. The concentrated residue was purified by a silica gel column chromatography to obtain 2-[[5-(3-chlorophenyl)-3-hydroxypyridine-2-carbonyl]amino]acetic acid (37 mg). (Yield 30%)

$^1$H NMR (DMSO-$d_6$) δ: 3.93 (2H, d, J=5.6 Hz), 7.52-7.57 (2H, m), 7.78 (1H, d, J=2.0 Hz), 7.79-7.81 (1H, m), 7.92-7.93 (1H, m), 8.54 (1H, d, J=2.0 Hz), 9.27 (1H, t, J=5.6 Hz), 12.41-12.49 (1H, br).

Example 32

Preparation of ethyl 2-[[5-(3-chlorophenyl)-3-hydroxypyridine-2-carbonyl]amino]acetate

[Chemical Formula 122]

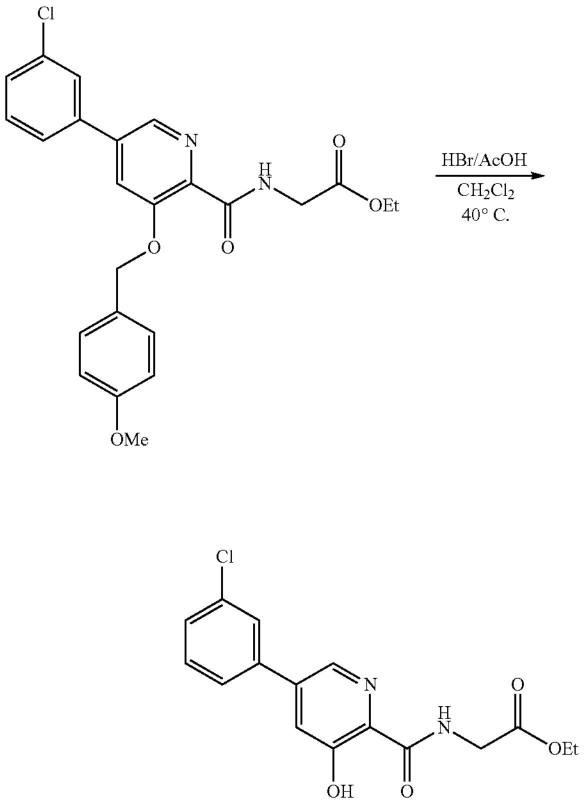

Ethyl 2-[[5-(3-chlorophenyl)-3-[(4-methoxypheny) methoxy]pyridine-2-carbonyl]amino]acetate (163 mg, 0.36 mmol), dichloromethane (10 mL), hydrogen bromide (30% acetic solution) (1 mL) were added to a reactor vessel, and the mixture was stirred at 40° C. for 2 hours. The reaction mixture was cooled under ice-cooling, and thereto was added saturated hydrogen carbonate solution, and the mixture was extracted with dichloromethane twice. The organic layers were combined, and the mixture was dried over sodium sulfate, and the solid was separated by filtration, and the filtrates were concentrated under reduced pressure. After the concentrated residue was purified by a silica gel column chromatography, the resulting mixture was further purified by an amino silica gel column chromatography to obtain a crude product. The crude product was purified by a reverse silica gel column to obtain ethyl 2-[[5-(3-chlorophenyl)-3-hydroxypyridine-2-carbonyl]amino]acetate (84 mg). (Yield 68%)

$^1$H NMR ($CDCl_3$) δ: 1.33 (3H, t, J=7.2 Hz), 4.24-4.31 (4H, m), 7.41-7.49 (4H, m), 7.57-7.58 (1H, m), 8.30 (1H, d, J=2.0 Hz), 8.42 (1H, br), 11.8 (1H, s).

Example 33

Preparation of 2-[[5-(3-chlorophenyl)-3-hydroxypyridine-2-carbonyl]amino]acetic acid

[Chemical Formula 123]

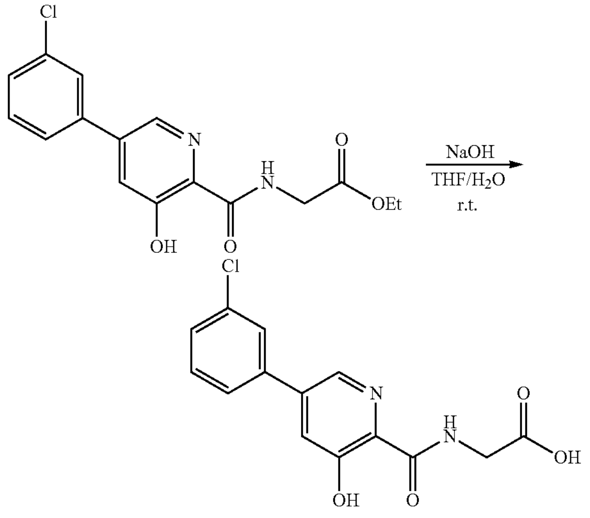

Ethyl 2-[[5-(3-chlorophenyl)-3-hydroxypyridine-2-carbonyl]amino]acetate (76 mg, 0.22 mmol), tetrahydrofuran (0.71 mL), and 1 mol/L aqueous sodium hydroxide solution (0.7 mL, 0.7 mmol) were added to a reactor vessel, and the mixture was stirred at room temperature for 2 hours. The reaction mixture was neutralized with 1 mol/L hydrochloric acid (0.8 mL, 0.8 mmol), and adjusted with 1 mol/L aqueous sodium hydroxide solution to around pH 2. The mixture was concentrated under reduced pressure to distill the solvent, and the precipitated solid was filtered under reduced pressure, and washed with water. The mixture was dried under reduced pressure to obtain 2-[[5-(3-chlorophenyl)-3-hydroxypyridine-2-carbonyl]amino]acetic acid (64 mg). (Yield 95%)

$^1$H NMR (DMSO-$d_6$) δ: 3.94 (2H, d, J=6.0 Hz), 7.52-7.57 (2H, m), 7.78 (1H, d, J=1.6 Hz), 7.79-7.81 (1H, m), 7.92-7.93 (1H, m), 8.55 (1H, d, J=1.6 Hz), 9.28 (1H, t, J=6.0 Hz), 12.4-12.5 (1H, br).

Example 34

Preparation of 2-[[3-chloro-5-(3-chlorophenyl)pyridine-2-carbonyl]amino]acetic acid

[Chemical Formula 124]

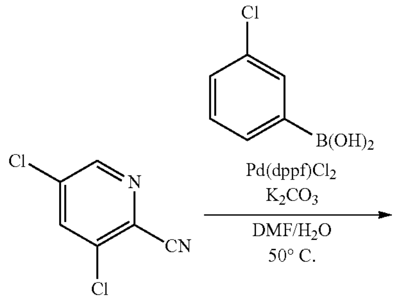

-continued

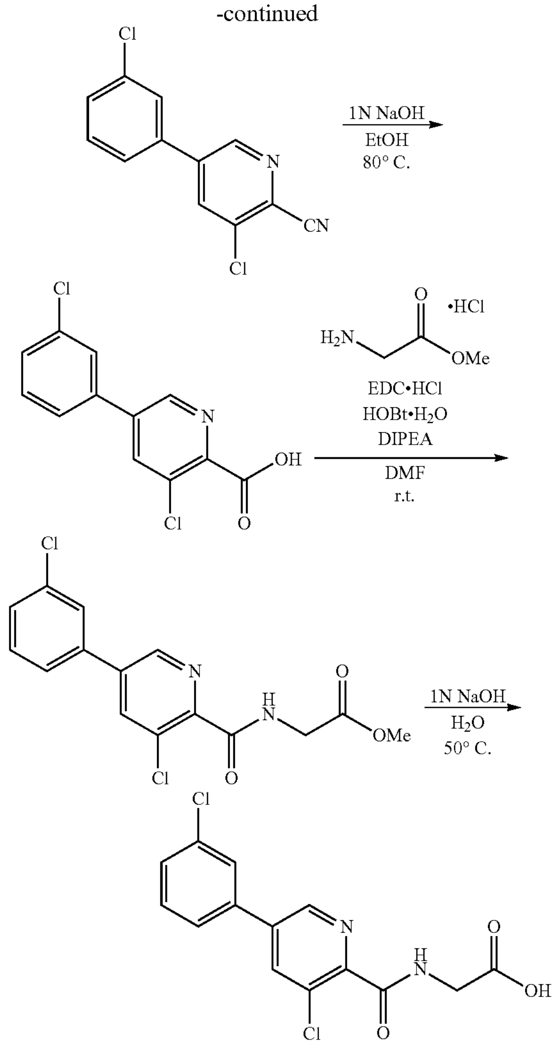

According to the methods described in the Patent Literature 2, 3,5-dichloropyridine-2-carbonitrile (13.50 g, 86.33 mmol), (3-chlorophenyl)boronic acid (15.68 g, 90.64 mmol), potassium carbonate (14.32 g, 103.62 mmol), dimethyl formamide (85 mL), water (10 mL), Pd(dppf)$Cl_2$ (316 mg, 0.43 mmol), and dimethyl formamide (4.3 mL) were added sequentially to a reactor vessel, and the mixture was subjected to a reaction at 50° C. (bath temperature) under nitrogen atmosphere for 19 hours. The worked up procedure was conducted to obtain 3-chloro-5-(3-chlorophenyl)pyridine-2-carbonitrile (21.51 g). (Yield quant.)

3-Chloro-5-(3-chlorophenyl)pyridine-2-carbonitrile (30.70 g, 123.25 mmol), ethanol (153 mL), and 1 mol/L aqueous sodium hydroxide solution (271 mL, 271 mmol) were added to a reactor vessel, and the mixture was subjected to a reaction at 80° C. (bath temperature) for 26 fours. The worked up procedure was conducted to obtain 3-chloro-5-(3-chlorophenyl)pyridine-2-carboxylic acid (33.83 g). (Yield quant.)

3-Chloro-5-(3-chlorophenyl)pyridine-2-carboxylic acid (33.83 g), dimethyl formamide (352 mL), glycine methyl ester hydrochloride salt (20.12 g, 160.25 mmol), 1-(3-dimethylaminopropyl)-3-ethylcarbodiimide hydrochloride salt (EDC·HCl) (35.44 g, 184.87 mmol), 1-hydroxybenzotriazole monohydrate (HOBt·$H_2O$) (25.00 g, 185.00 mmol), and diisopropyl ethyl amine (85 mL, 493.23 mmol) were added to a reactor vessel, and the mixture was subjected to a reaction at room temperature for 15 hours. The worked up procedure was conducted to obtain methyl 2-[[3-chloro-5-(3-chlorophenyl)pyridine-2-carbonyl]amino]acetate (32.63 g). (Yield 78.1%)

Methyl 2-[[3-chloro-5-(3-chlorophenyl)pyridine-2-carbonyl]amino]acetate (32.67 g, 99.27 mmol), 2 mol/L aqueous sodium hydroxide solution (168 mL, 336 mmol), and water (96 mL) were added to a reactor vessel, and the mixture was subjected to a reaction at 50° C. (bath temperature) for 3 hours. After cooled to room temperature, the mixture was adjusted with hydrochloric acid to pH 4. The precipitated materials were filtered and dried to obtain 2-[[3-chloro-5-(3-chlorophenyl)pyridine-2-carbonyl]amino]acetic acid (32.19 g). Yield (99.7%)

$^1$H NMR (DMSO-$d_6$) δ: 3.95 (2H, d, J=6.0 Hz), 7.54-7.59 (2H, m), 7.82-7.87 (1H, m), 7.98-7.99 (1H, m), 8.43 (1H, d, J=2.0 Hz), 8.93-8.96 (2H, m), 12.71 (1H, br).

In a two dimensional NMR, a NOESY correlation between protons at 4-position and 6-position of the pyridine ring and proton of the chlorophenyl group was found. It was decided from this event that the obtained compound was the present isomer.

Example 35

Preparation of methyl 2-[[5-chloro-3-(3-chlorophenyl)pyridine-2-carbonyl]amino]acetate

[Chemical Formula 125]

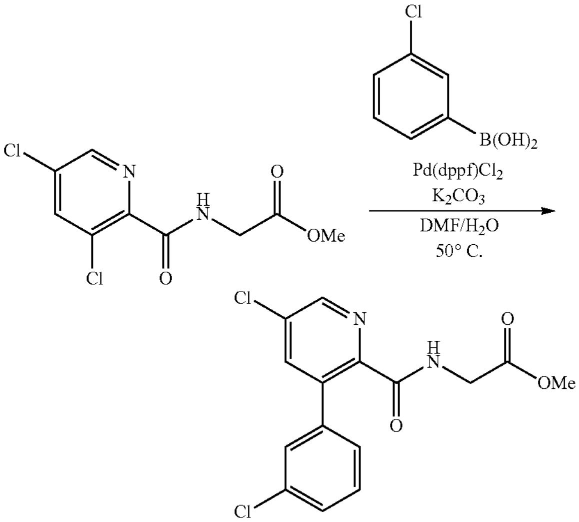

Methyl 2-[(3,5-dichloropyridine-2-carbonyl)amino]acetate (1.00 g, 3.80 mmol), (3-chlorophenyl)boronic acid (595.9 mg, 3.81 mmol), and dimethyl formamide (8.0 mL) were added to a reactor vessel, and the atmosphere of the reaction system was purged with nitrogen. A solution of potassium carbonate (1.05 g, 7.60 mmol) and water (1.0 mL), Pd(dppf)$Cl_2$ (278.4 mg, 0.38 mmol), and dimethyl formamide (2.0 mL) were added to the mixture, and the atmosphere of the reaction system was purged with nitrogen again, and the mixture was then subjected to a reaction at 47° C. for 16 hours. After the reaction mixture was concentrated under reduced pressure, the mixture was extracted with ethyl acetate and water, and the organic layer was concentrated under reduced pressure. Methanol was added to the concentrated residue, and the solid component was separated by filtration, and the filtrates were concentrated under reduced pressure. The concentrated residue was purified by a column chromatography to obtain methyl 2-[[5-chloro-3-(3-chlorophenyl)pyridine-2-carbonyl]amino]acetate (45 mg). (Yield 3.5%)

MS: m/z=339/341

Example 36

Preparation of methyl 2-[[5-chloro-3-(3-chlorophenyl)pyridine-2-carbonyl]amino]acetate and 2-[[5-chloro-3-(3-chlorophenyl)pyridine-2-carbonyl]amino]acetic acid

[Chemical Formula 126]

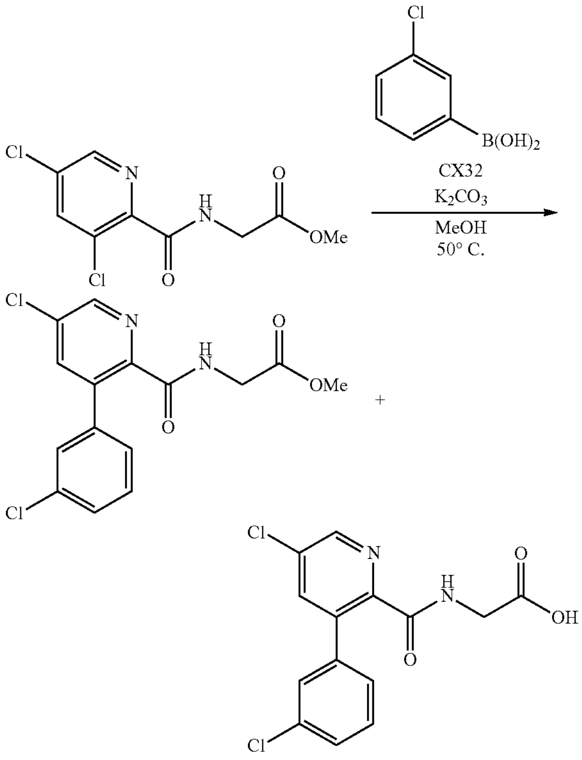

Methyl 2-[(3,5-dichloropyridine-2-carbonyl)amino]acetate (1.01 g, 3.84 mmol), (3-chlorophenyl)boronic acid (1.18 g, 7.55 mmol), potassium carbonate (0.51 g, 3.69 mmol), CX32 (127.6 mg, 0.20 mmol), and methanol (3.0 mL) were added to a reactor vessel, and the atmosphere of the reaction system was purged with nitrogen, and the mixture was subjected to a reaction at 60° C. for 21 hours. The reaction mixture was extracted with 2 mol/L hydrochloric acid (10 mL) and ethyl acetate (20 mL), and the organic layer was dried over magnesium sulfate, and then concentrated under reduced pressure. The concentrated residue was purified by a column chromatography to obtain methyl 2-[[5-chloro-3-(3-chlorophenyl)pyridine-2-carbonyl]amino]acetate (559 mg) and 2-[[5-chloro-3-(3-chlorophenyl)pyridine-2-carbonyl]amino]acetic acid (110 mg).

Preparation of methyl 2-[[5-chloro-3-(3-chlorophenyl)pyridine-2-carbonyl]amino]acetate Yield 43%

Preparation of 2-[[5-chloro-3-(3-chlorophenyl)pyridine group-2-carbonyl]amino]acetic acid Yield 9%

$^1$H NMR ($CDCl_3$): δ 8.55 (d, J=2.3 Hz, 1H), 8.25 (t, J=5.6 Hz, 1H), 7.68 (d, J=2.2 Hz, 1H), 7.37 (dt, J=8.1, 1.7 Hz, 1H), 7.33 (t, J=7.7 Hz, 1H), 7.29 (t, J=1.6 Hz, 1H), 7.19 (dt, J=7.4, 1.5 Hz, 1H), 4.18 (d, J=5.7 Hz, 2H).

In a two dimensional NMR, a NOESY correlation between proton at 4-position of the pyridine ring and proton of the chlorophenyl group was found, while a NOESY correlation between proton at 6-position of the pyridine ring and proton of the chlorophenyl group was not found. It was decided from this event that the obtained compound was the present isomer.

Example 37

Preparation of 2-[[5-(3-chlorophenyl)-3-hydroxypyridine-2-carbonyl]amino]ethyl acetate (I type crystal form)

[Chemical Formula 127]

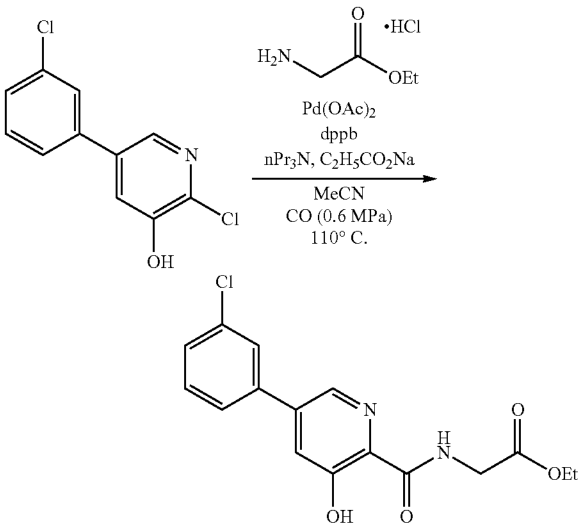

2-Chloro-5-(3-chlorophenyl)-3-hydroxy pyridine (4.00 g, 16.661 mmol), glycine ethyl ester hydrochloride salt (2.44 g, 17.481 mmol), palladium acetate (9.4 mg, 0.042 mmol), 1,4-bis(diphenylphosphino)butane (35.8 mg, 0.084 mmol), tripropylamine (7.16 g, 49.976 mmol), sodium propionate (160.2 mg, 1.666 mmol), and acetonitrile (48 mL) were added to a reactor vessel, and the atmosphere of the reaction system was purged with nitrogen and carbon monoxide successively, and pressurized with carbon monoxide at 0.6 MPa while the pressure of the reaction system was maintained at 0.6 MPa, and the mixture was stirred at 110° C. for 18 hours. The reaction mixture was filtered to remove the solid materials and washed with acetonitrile (32 mL).

Separately, 2-chloro-5-(3-chlorophenyl)-3-hydroxypyridine (4.00 g, 16.661 mmol), glycine ethyl ester hydrochloride salt (2.44 g, 17.481 mmol), palladium acetate (9.4 mg, 0.042 mmol), 1,4-bis(diphenylphosphino)butane (35.6 mg, 0.083 mmol), tripropylamine (7.15 g, 49.906 mmol), and acetonitrile (48 mL) were added to a reactor vessel, and the atmosphere of the reaction system was purged with nitrogen and carbon monoxide successively, and pressurized with carbon monoxide at 0.6 MPa while the pressure of the reaction system was maintained at 0.6 MPa, and the mixture was stirred at 110° C. for 46 hours. The reaction mixture was filtered to remove the solid materials, and washed with acetonitrile (32 mL). The filtrates were concentrated under reduced pressure to 16 mL.

Separately, 2-chloro-5-(3-chlorophenyl)-3-hydroxypyridine (4.00 g, 16.661 mmol), glycine ethyl ester hydrochloride salt (2.44 g, 17.481 mmol), palladium acetate (9.4 mg, 0.042 mmol), 1,4-bis(diphenylphosphino)butane (71.1 mg, 0.167 mmol), tripropylamine (7.16 g, 49.976 mmol), and acetonitrile (48 mL) were added to a reactor vessel, and the atmosphere of the reaction system was purged with nitrogen and carbon monoxide successively, and pressurized with carbon monoxide at 0.6 MPa while the pressure of the reaction system was maintained at 0.6 MPa, and the mixture was stirred at 110° C. for 46 hours. The reaction mixture was filtered to remove the solid materials, and washed with acetonitrile (32 mL).

The mixture composed of three parts of the reaction were combined, and the half of the solutions were concentrated under reduced pressure to 24 mL. Isopropanol (36 mL) was added thereto, and the mixture was dissolved by heating at 65° C., and water (12 mL) was added thereto, and the mixture was stirred at 50° C. Water (24 mL) was added dropwise thereto, and the resulting mixture was heated to 65° C. and stirred, and then cooled to 30° C. The precipitated solid was filtered under reduced pressure, and washed with mixed solution of isopropanol (18 mL) and water (12 mL). The mixture was dried under reduced pressure to obtain an I type crystal of 2-[[5-(3-chlorophenyl)-3-hydroxypyridine-2-carbonyl]amino]ethyl acetate (5.99 g). (Yield 72%)

An X-ray crystallographic analysis was conducted on the obtained I type crystal under the conditions below.

Powder X-Ray Crystallographic Analysis Condition

Device: MiniFlex600 (Rigaku)

Operating condition;

X ray output: Cu-Kα, Tube voltage: 40 kV, Tube current: 15 mA, Sampling range: 0.02°

Scan range: 3° to 40°

Measured Temperature: Room Temperature

A XRD diffraction pattern of the I type crystal is shown in FIG. 1. Also the diffraction angle (2θ) value of the I type crystal is shown in Table 10.

TABLE 10

| Peak No. | 2θ (°) |
|---|---|
| 1 | 5.72 |
| 2 | 7.96 |
| 3 | 11.04 |
| 4 | 11.82 |
| 5 | 14.14 |
| 6 | 14.54 |
| 7 | 15.08 |
| 8 | 15.94 |
| 9 | 17.74 |
| 10 | 18.20 |
| 11 | 20.40 |
| 12 | 20.78 |
| 13 | 24.10 |
| 14 | 24.68 |

TABLE 10-continued

| Peak No. | 2θ (°) |
|---|---|
| 15 | 25.10 |
| 16 | 26.82 |
| 17 | 39.22 |

The I type crystal of the compound (a3-1-A) of the present invention can be characterized by having one or more of the below-mentioned characteristic peaks in the powder X ray diffraction pattern.

(1) The crystal has preferably the substantially-identical patterns to the powder X ray diffraction pattern indicated in FIG. 1.

(2) Examples of the characteristic patterns in the powder X ray diffraction patterns of the I type crystal include as the diffraction angles expressed as 26, 7.96°±0.2°, 11.82°±0.2°, 14.14°±0.2°, and/or 15.94°±0.2°. Examples of another characteristic peaks include 14.54°±0.2°, 15.08°±0.2°, 24.10°±0.2°, 24.68°±0.2°, and/or 26.82°±0.2°. Examples of the other characteristic peaks include 5.72°±0.2°, 11.04°±0.2°, 17.74°±0.2°, 18.20°±0.2°, 20.40°±0.2°, 20.78°±0.2°, 25.10°±0.2°, and/or 39.22°±0.2°.

Example 38

Preparation of ethyl 2-[[5-(3-chlorophenyl)-3-hydroxypyridine-2-carbonyl]amino]acetate (II type crystal form)

[Chemical Formula 128]

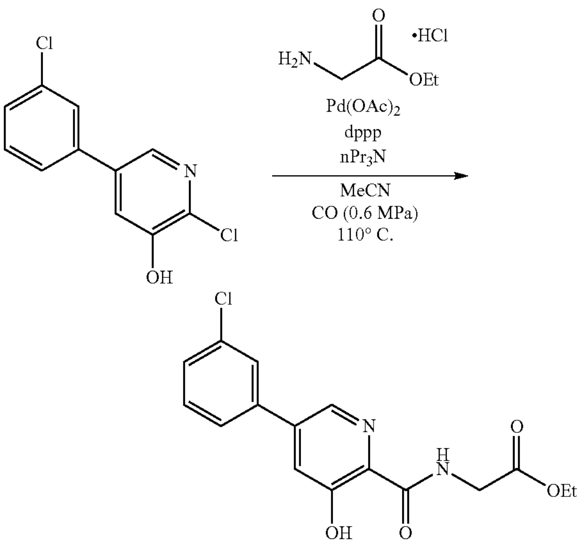

2-Chloro-5-(3-chlorophenyl)-3-hydroxypyridine (4.00 g, 16.661 mmol), glycine ethyl ester hydrochloride salt (2.44 g, 17.481 mmol), palladium acetate (9.3 mg, 0.041 mmol), 1,4-bis(diphenylphosphino)butane (35.6 mg, 0.083 mmol), tripropylamine (11.94 g, 83.339 mmol), and acetonitrile (48 mL) were added to a reactor vessel, and the atmosphere of the reaction system was purged with nitrogen and carbon monoxide successively, and pressurized with carbon monoxide at 0.6 MPa while the pressure of the reaction system was maintained at 0.6 MPa, and the mixture was stirred at 110° C. for 46 hours. The reaction mixture was filtered to remove the solid materials, and washed with acetonitrile (32 mL). The filtrates were concentrated under reduced pressure to 12 mL, and transferred with acetonitrile (4 mL). Isopropanol (24 mL) was added dropwise thereto, and the mixture was stirred at 35° C., and after water (16 mL) was added dropwise thereto, the mixture was stirred at 30° C. Water (8 mL) was added dropwise thereto, and the mixture was stirred at 30° C., and the precipitated solid was then filtered under reduced pressure, and washed with mixed solution of isopropanol (12 mL) and water (8 mL). The mixture was dried under reduced pressure to obtain II type of crystal of ethyl 2-[[5-(3-chlorophenyl)-3-hydroxypyridine-2-carbonyl]amino]acetate (3.61 g). (Yield 65%)

An X-ray crystallographic analysis was conducted on the obtained II type crystal under the conditions below.

Powder X-Ray Crystallographic Analysis Condition

Device: MiniFlex600 (Rigaku)

Operating condition;

X ray output: Cu-Kα, Tube voltage: 40 kV, Tube current: 15 mA, Sampling range: 0.020

Scan range: 3° to 400

Measured Temperature: Room Temperature

Figure 2:
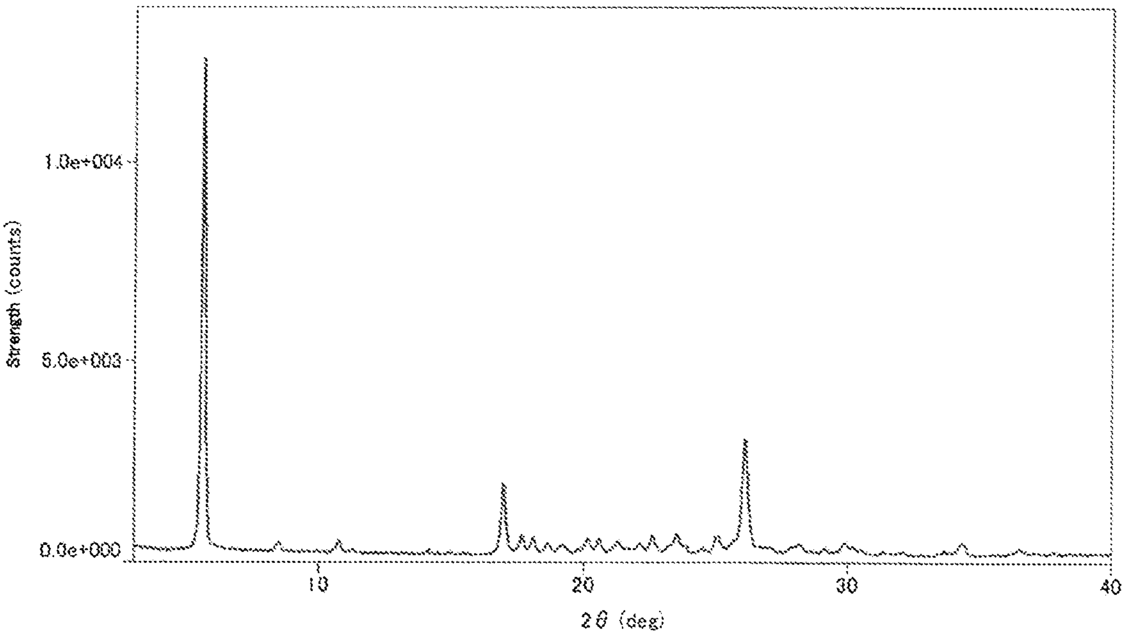
FIG. 2 shows a powder X-ray diffraction pattern of the II type crystal of the compound [I(A)] of the present invention.
Figure 3:
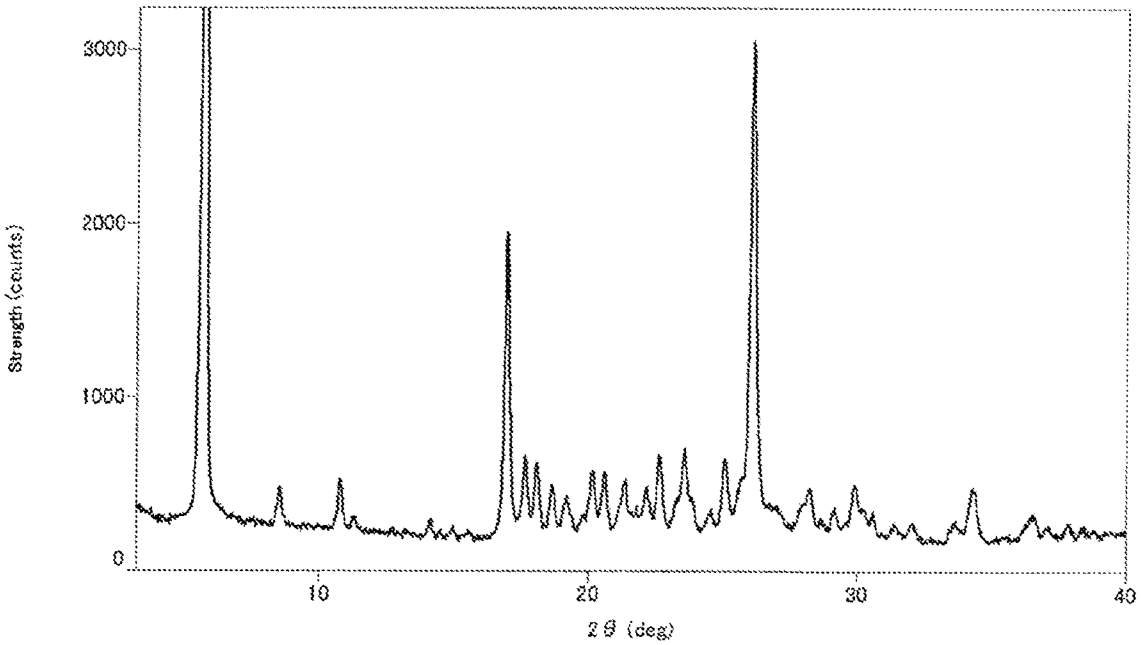
FIG. 3 shows the FIG. 2 which is enlarged in the vertical direction.

A XRD diffraction pattern of the II type crystal is shown in FIGS. 2 and 3. Also the diffraction angle (28) value of the II type crystal is shown in Table 11.

TABLE 11

| Peak No. | 2θ (°) |
|---|---|
| 1 | 5.64 |
| 2 | 8.52 |
| 3 | 10.78 |
| 4 | 16.98 |
| 5 | 17.66 |
| 6 | 18.08 |
| 7 | 18.66 |
| 8 | 20.16 |
| 9 | 20.60 |
| 10 | 21.34 |
| 11 | 22.64 |
| 12 | 23.56 |
| 13 | 25.08 |
| 14 | 26.12 |
| 15 | 29.90 |
| 16 | 34.34 |

The II type crystal of the compound (a3-1-A) of the present invention can be characterized by having one or more of the below-mentioned characteristic peaks in the powder X ray diffraction pattern.

(1) The crystal has preferably the substantially-identical patterns to the powder X ray diffraction pattern indicated in FIG. 2 and/or FIG. 3.

(2) Examples of the characteristic patterns in the powder X ray diffraction patterns of the II type crystal include as the diffraction angles expressed as 20, 8.52°±0.2°, 16.98°±0.2°, 20.16°±0.2°, and/or 26.12°±0.2°. Examples of another characteristic peaks include 10.78°±0.2°, 23.56°±0.2°, 29.90°±0.2°, and/or 34.34°±0.2°. Examples of the other characteristic peaks include 5.64°±0.2°, 17.66°±0.2°, 18.08°±0.2°, 18.66°±0.2°, 20.60°±0.2°, 21.34±0.2°, 22.64°±0.2°, and/or 25.08°±0.2°.

Example 39

Preparation of 2-chloro-5-(3-chlorophenyl)-3-hydroxypyridine

[Chemical Formula 129]

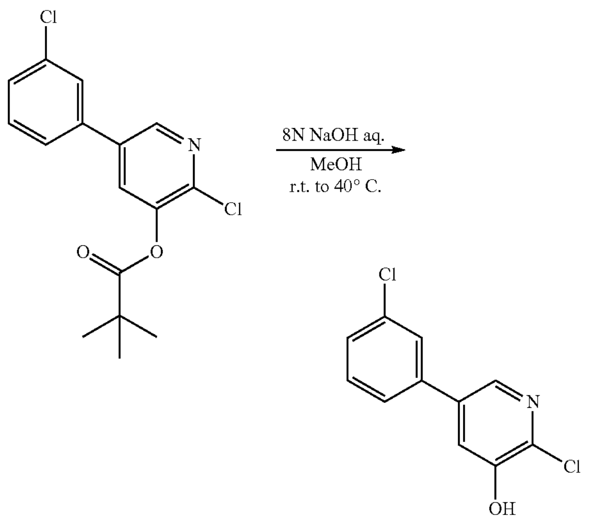

2,2-Dimethyl [2-chloro-5-(3-chlorophenyl)-3-pyridyl] propionate (99.9 mg, 0.308 mmol), methanol (1.03 mL), and 8 mol/L aqueous sodium hydroxide solution (0.116 mL) were added to a reactor vessel, and the mixture was stirred at room temperature for 1.5 hours, and then raised to 40° C. and stirred for additional three hours. 8 mol/L Aqueous sodium hydroxide solution (0.116 mL) was added thereto, and the mixture was stirred at 40° C. for 1.5 hours, and it was confirmed a disappearance of the starting material. The reaction mixture was adjusted with 6 mol/L hydrochloric acid to around pH 3, and water was further added thereto, and the mixture was extracted with chloroform three times. The organic layers were combined, dried over sodium sulfate, and concentrated to dryness to obtain a crude product. This crude product was purified by a silica gel column chromatography to obtain 2-chloro-5-(3-chlorophenyl)-3-hydroxy pyridine (68.7 mg). (Yield 92%)

$^1$H NMR ($CDCl_3$) δ: 5.70 (1H, brs), 7.38-7.45 (3H, m), 7.50 (1H, d, J=2.3 Hz), 7.53-7.54 (1H, m), 8.19 (1H, d, J=2.1 Hz).

Example 40

Preparation of 2-chloro-5-(3-chlorophenyl)-3-hydroxypyridine

[Chemical Formula 130]

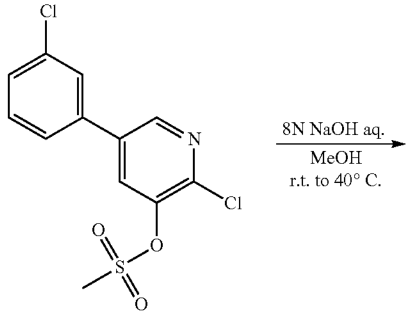

-continued

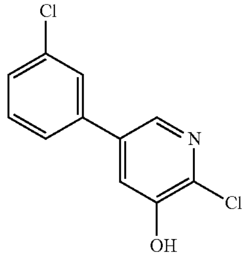

[2-Chloro-5-(3-chlorophenyl)-3-pyridyl]methane sulfonate (504.1 mg, 1.584 mmol), methanol (5.20 mL), and 8 mol/L aqueous sodium hydroxide solution (0.99 mL) were added to a reactor vessel, and the mixture was stirred at 40° C. for 13 hours. After it was confirmed the disappearance of [2-chloro-5-(3-chlorophenyl)-3-pyridyl]methane sulfonate, the reaction mixture was adjusted with 6 mol/L hydrochloric acid to around pH 3, and water was further added thereto, and the mixture was extracted with chloroform three times. The organic layers were combined, and the mixture was dried over sodium sulfate, and then concentrated to dryness to obtain a crude product. The crude product was purified by a silica gel column chromatography to obtain 2-chloro-5-(3-chloropheny)-3-hydroxypyridine (380.3 mg). (Yield 92%)

$^1$H NMR ($CDCl_3$) δ: 5.69 (1H, brs), 7.38-7.45 (3H, m), 7.50 (1H, d, J=2.1 Hz), 7.53-7.54 (1H, m), 8.19 (1H, d, J=2.3 Hz).

INDUSTRIAL APPLICABILITY

The present invention provides a process for preparing the compound (I) in good yields, said compound being suitable for a production as a medicine on industrial scale.

The invention claimed is:

1. A process for preparing a compound of formula (a3):

a3

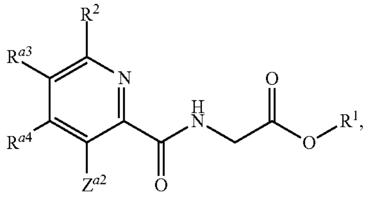

wherein:

$R^2$ is a hydrogen atom or an optionally substituted methyl group, $R^{a3}$ is a phenyl group, optionally substituted with halogen atom, $R^{a4}$ is a hydrogen atom, or alternatively, $R^{a3}$ and $R^{a4}$ bind to each other and combine together with a pyridine group to which they are adjacent to form an isoquinoline group which may be optionally substituted with phenyloxy group, and $Z^{a2}$ is a hydroxy group or a substituent represented by formula:

wherein $P^1$ is a protecting group for hydroxy group;

said process comprising reacting a compound of formula (a1):

a1

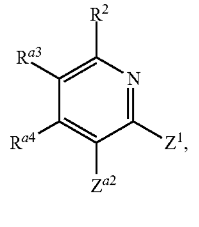

wherein $R^2$, $R^{a3}$, $R^{a4}$, and $Z^{a2}$ are as defined above; and $Z^1$ is a chlorine atom, a bromine atom, or an iodine atom, with a compound (2) represented by formula:

2

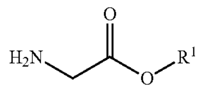

wherein $R^1$ is an optionally substituted alkyl group, a hydrogen atom, or a resin residue, or a salt thereof, and carbon monoxide, in the presence of a palladium catalyst, in the presence or absence of a ligand, in the presence of a base, in a solvent, to obtain the compound (a3).

2. The process of claim 1, wherein the pressure of the carbon monoxide during the reaction is between 0.01 MPa to 1 MPa.

3. The process of claim 1, wherein the molar ratio of the compound of formula (a1) used in the reaction to the compound of formula (2) used in the reaction is 2:1 to 1:2.

4. The process of claim 1, wherein the reaction is conducted in nitriles as the solvent and between 20 to 150° C. as a reaction temperature.

5. The process of claim 1, wherein the compound of formula (a1) is a compound of formula (a1-5-a):

a1-5-a

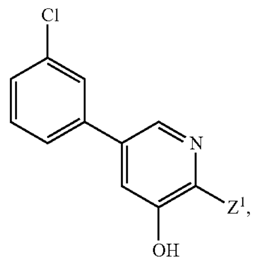

wherein $Z^1$ is a chlorine atom, a bromine atom or an iodine atom, and the compound of formula (a3) is a compound of formula (a3-3-a):

a3-3-a

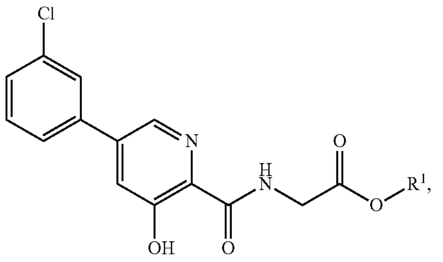

wherein $R^1$ is an optionally substituted alkyl group, a hydrogen atom, or a resin residue.

6. The process of claim 1, wherein the compound of formula (a3) is a compound of formula (a3-1):

a3-1

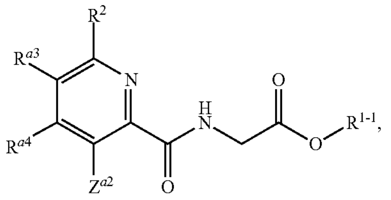

wherein $R^{1-1}$ is an optionally substituted alkyl group or a resin residue, $R^2$ is a hydrogen atom or an optionally substituted methyl group, $R^{a3}$ is a phenyl group optionally substituted with halogen atom, and $R^{a4}$ is a hydrogen atom, or alternatively, $R^{a3}$ and $R^{a4}$ bind to each other and combine together with the pyridine group to which they are adjacent to form an isoquinoline group optionally substituted with phenyloxy group, $Z^{a2}$ is a hydroxy group or a substituent represented by formula:

wherein $P^1$ is a protecting group for hydroxy group, further comprising converting the compound of formula (a3-1) into the compound of formula (a1):

aI

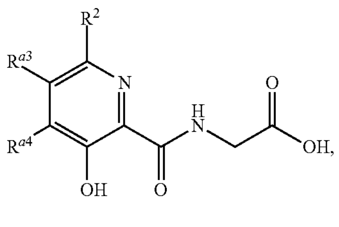

wherein the symbols are the same as defined above.

7. The process of claim 1, wherein:

(i) $R^2$ is a hydrogen atom, $R^{a3}$ is a 3-chlorophenyl group, and $R^{a4}$ is a hydrogen atom, or alternatively, (ii) $R^2$ is a methyl group, and $R^{a3}$ and $R^{a4}$ bind to each other and combine together with a pyridine group to which they are adjacent to form a 7-phenyloxy-isoquinoline group.

8. The process of claim 6, wherein the compound of formula (a3-1) is a compound of formula (a3-2-a):

a3-2-a

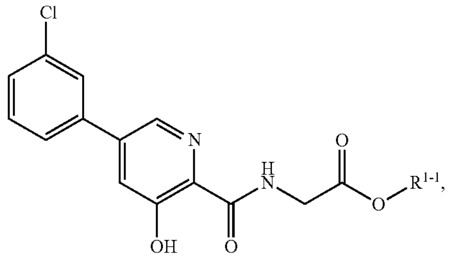

wherein $R^{1-1}$ is an optionally substituted alkyl group or a resin residue, and the compound of formula (a1) is a compound of formula [I(A)]:

I(A)

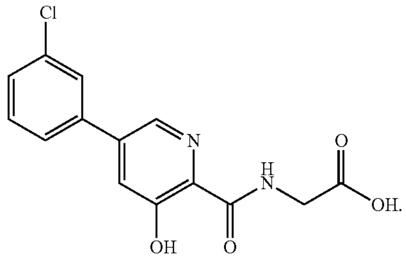

9. The process according to claim 1, wherein the compound of formula (a1) is a compound of formula (a1-1-a):

a1-1-a

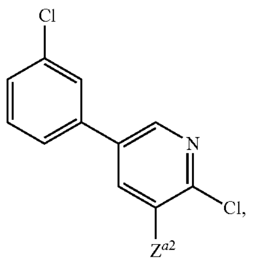

wherein $Z^{a2}$ is a hydroxy group or a substituent represented by formula:

wherein $P^1$ is a protecting group for hydroxy group, and the compound of formula (a1-1-a) is prepared by reacting a compound of formula (a4):

a4

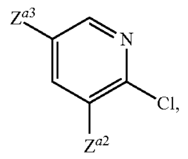

wherein $Z^{a3}$ is bromine atom, an iodine atom, or a trifluoromethanesulfoxy group, and $Z^{a2}$ is the same as defined as above, with a compound of formula (a5):

a5

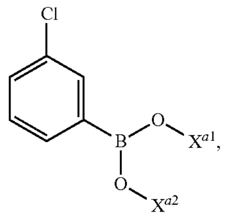

wherein $X^{a1}$ and $X^{a2}$ each independently is a hydrogen atom or an alkyl group, or alternatively both of them bind to each other to form an alkylene group, in the presence or absence of a base, in the presence or absence of a palladium catalyst, in the presence or absence of a ligand, in a solvent or in the absence of a solvent.

10. The process according to claim 9, wherein the compound of formula (a1-1-a) is a compound of formula (a1-4-a):

a1-4-a

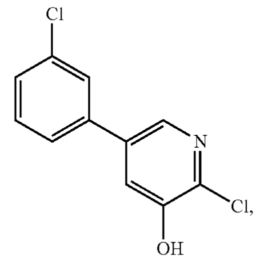

and the compound of formula (a4) a compound of formula (a4-2):

a4-2

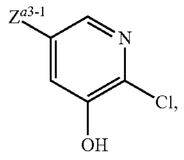

wherein $Z^{a3}$ is a bromine atom or an iodine atom.

11. A process for preparing a compound of formula [1(A)]:

I(A)

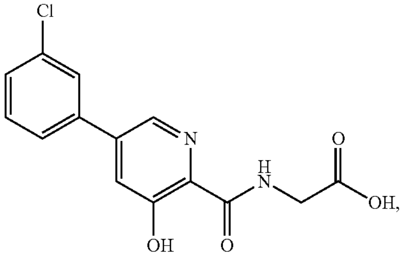

said process comprising:

(i) reacting a compound of formula (a4):

a4

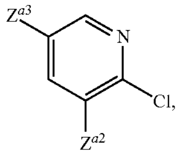

wherein $Z^{a2}$ is a hydroxy group or a substituent represented by formula:

wherein $P^1$ is a protecting group for hydroxy group, $Z^{a3}$ is a bromine atom, an iodine atom or a trifluoromethanesulfoxy group, with a compound of formula (a5):

a5

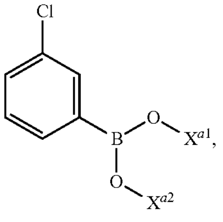

wherein $X^{a1}$ and $X^{a2}$ are each independently a hydrogen atom or an alkyl group, or alternatively, both of them bind to each other to form an alkylene group, in the presence or absence of a base, in the presence or absence of a palladium catalyst, in a solvent or in the absence of a solvent to prepare a compound of formula (a1-1-a):

a1-1-a

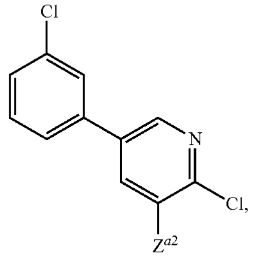

wherein, $Z^{a2}$ is the same as defined above:

(ii) reacting the compound of formula (a1-1-a) with a compound of formula (2-1):

2-1

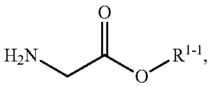

wherein $R^{1-1}$ is an optionally substituted alkyl group or a resin residue, or a salt thereof, and carbon monoxide in the presence or absence of a palladium catalyst, in the presence or absence of a ligand, in the presence or absence of a base, in a solvent or in the absence of a solvent to obtain a compound of formula (a3-1-a):

a3-1-a

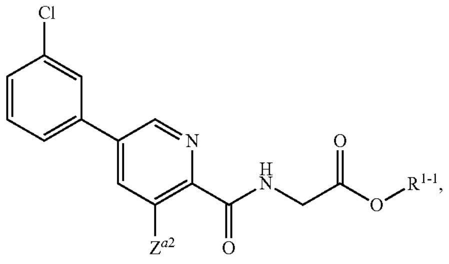

wherein $R^{1-1}$ and $Z^{a2}$ are the same defined above;

and (iii) converting the compound of formula (a3-1-a) into the compound of formula [I(A)]

I(A)

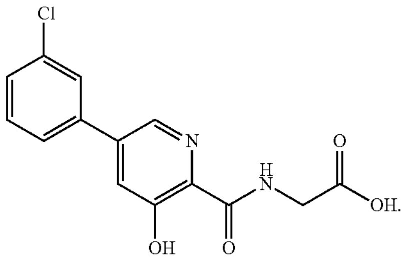

12. The process of claim 11, wherein compound of formula (a4) is a compound of formula (a4-2):

a4-2

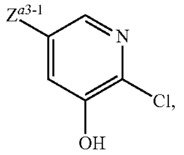

wherein $Z^{a3-1}$ is a bromine atom or an iodine atom, the compound of formula (a1-1-a) is a compound of formula (a1-4-a):

a1-4-a

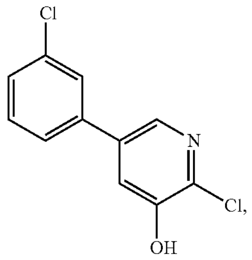

and the compound of formula (a3-1-a) is a compound of formula (a3-2-a):

a3-2-a

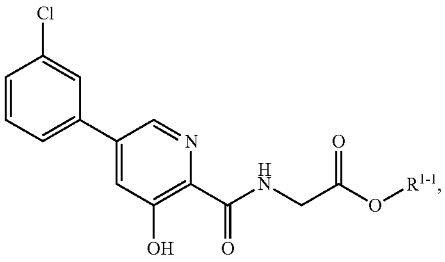

wherein $R^{1-1}$ is an optionally substituted alkyl group or a resin residue.

13. A process for preparing a compound of formula [I(A)]:

I(A)

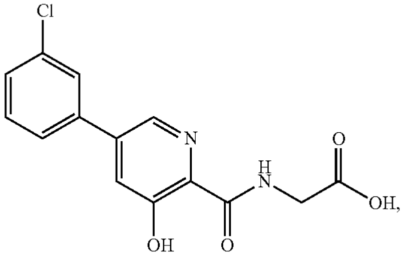

said process comprising:

(i) reacting a of compound of formula (a4-1):

a4-1

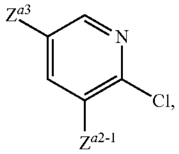

wherein $Z^{a2-1}$ is a substituent represented by formula:

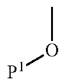

wherein $P^1$ is a protecting group for a hydroxy group, and $Z^{a3}$ is a bromine atom, an iodine atom, or a trifluoromethanesulfoxy group, with a compound of formula (a5):

a5

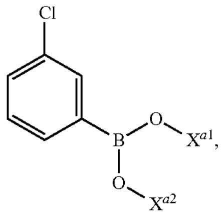

wherein $X^{a1}$ and $X^{a2}$ are each independently a hydrogen atom, or an alkyl group, or alternatively both of them bind to each other to form an alkylene group, in the presence of absence of a base, in the presence of absence of a palladium catalyst, in a solvent or in the absence of a solvent, to prepare a compound of formula (a1-3-a)

a1-3-a

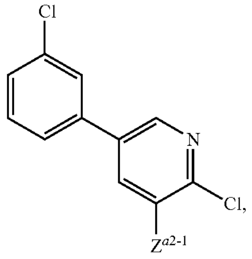

wherein $Z^{a2-1}$ is the same as defined above;

(ii) converting the compound of formula (a1-3-a) into the compound of formula (a1-4-a):

a1-4-a

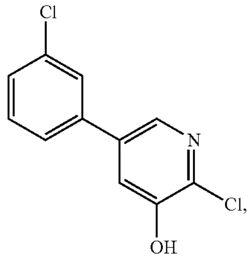

(iii) reacting the compound of formula (a1-4-a) with a compound of formula (2-1):

2-1

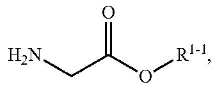

wherein $R^{1-1}$ is an optionally substituted alkyl group or a resin residue, or a salt thereof, and carbon monoxide in the presence or absence of a palladium catalyst, in the presence or absence of a ligand, in the presence or absence of a base, and in a solvent or in the absence of a solvent to prepare the compound of formula (a3-2-a):

a3-2-a

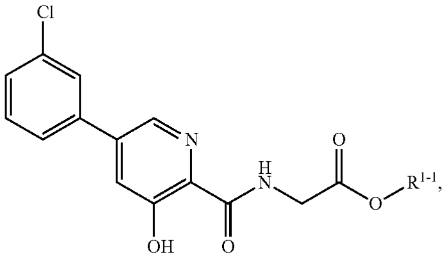

wherein $R^{1-1}$ is the same as defined above; and (iv) converting the compound of formula (a3-2-a) into the compound of formula (I(A)):

I(A)

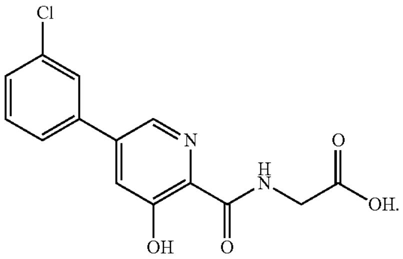

14. A process for preparing a compound of formula (b3-1):

b3-1

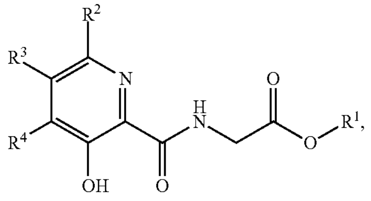

wherein $R^1$ is an optionally substituted alkyl group, a hydrogen atom, or a resin residue, $R^2$ is a hydrogen atom, or an optionally substituted methyl group, $R^3$ is a phenyl group which may be optionally substituted with halogen atom, a chlorine atom, a bromine atom, an iodine atom, or a trifluoromethanesulfoxy group, and $R^4$ is a hydrogen atom, or alternatively, $R^3$ and $R^4$ bind to each other and combine together with the pyridine group to which they are adjacent to form an isoquinoline group which may be optionally substituted with phenyloxy group, said process comprising:

(i) reacting a compound of formula (b1):

b1

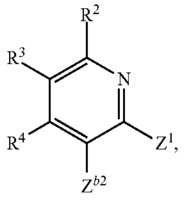

wherein $Z^1$ is a chlorine atom, a bromine atom, or an iodine atom, $Z^{b2}$ is a chlorine atom, a bromine atom or an iodine atom, and $R^2$, $R^3$, and $R^4$ are the same as defined above, with a compound of formula (2):

2

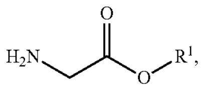

wherein $R^1$ is an optionally substituted alkyl group, a hydrogen atom, or a resin residue, or a salt thereof, and carbon monoxide, in the presence of a palladium catalyst, in the presence or absence of a ligand, in the presence of a base, in a solvent to obtain a compound of formula (b3):

b3

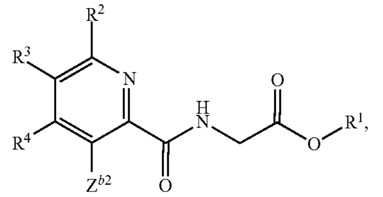

wherein the symbols are the same as defined above; and (ii) reacting the compound of formula (b3) with a compound of formula (b4):

b4

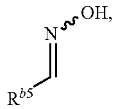

wherein $R^{b5}$ is an optionally substituted aryl group, or an optionally substituted alkyl group, in the presence of a palladium catalyst, in the presence or absence of a ligand, in the presence of a base, in a solvent to prepare a compound of formula (b3-1):

b3-1

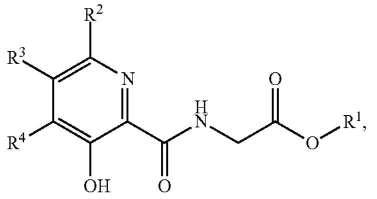

wherein the symbols are the same as defined above.

15. The process of claim 14, wherein a pressure of carbon monoxide during a reaction is between 0.01 MPa to 1 MPa.

16. The process of claim 14, wherein a molar ratio of the compound of formula (b1) used in the reaction to the compound of formula (2) used in the reaction is between 2:1 to 1:2.

17. The process of claim 14, wherein the reaction is conducted in nitriles as a solvent, and between 20° C. to 150° C. as a reaction temperature.

18. The process of claim 14, wherein the compound of formula (b3-1) is a compound of formula (b3-2-2):

b3-2-2

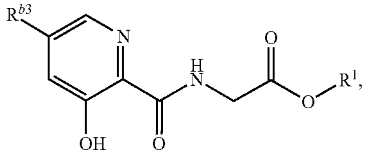

wherein:

$R^1$ is an optionally substituted alkyl group, a hydrogen atom, or a resin residue, $R^{b3}$ is a chlorine atom, a bromine atom, an iodine atom, or a trifluoromethanesulfoxy group, and wherein said process comprises reacting the compound of formula (b-3-2-2) with a compound of formula (b6):

b6

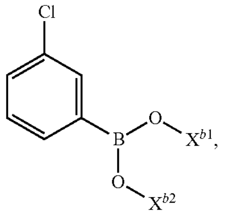

wherein:

$X^{b1}$ and $X^{b2}$ are each independently a hydrogen atom or an alkyl group, or alternatively, both of them bind to each other to form an alkylene group, in the presence or absence of a base, in the presence or absence of a palladium catalyst, in a solvent or in the absence of a solvent to obtain a compound of formula (b3-2-a):

b3-2-a

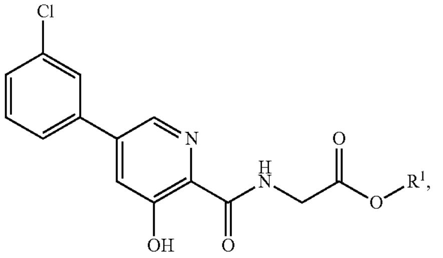

wherein the symbols are the same as defined above.

19. The process of claim 14, wherein the compound of formula (b3-1) is a compound of formula (b3-1-1):

b3-1-1

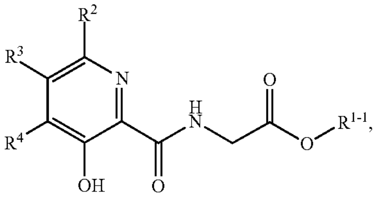

wherein:

$R^{1-1}$ is an optionally substituted alkyl group or a resin residue, $R^2$ is a hydrogen atom or an optionally substituted methyl group, $R^3$ is a phenyl group optionally substituted with halogen atom, a chlorine atom, a bromine atom, an iodine atom, or a trifluoromethanesulfoxy group, and $R^4$ is a hydrogen atom, or alternatively $R^3$ and $R^4$ bind to each other and combine together with the pyridine group to which they are adjacent to form an isoquinoline group optionally substituted with phenyloxy group, and converting the compound of formula (b3-1-1) into the compound of formula (I):

I

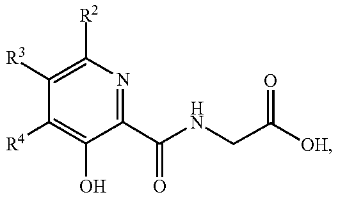

wherein the symbols are the same as defined above.

20. The process of claim 14, wherein:

(i) $R^2$ is a hydrogen atom, $R^3$ is a 3-chlorophenyl group, and $R^4$ is a hydrogen atom, or alternatively, (ii) $R^2$ is a methyl group, and $R^3$ and $R^4$ bind to each other and combine together with a pyridine group to which they are adjacent to form a 7-phenyloxy-isoquinoline group.

21. A process for preparing a compound of formula (bI-1):

bI-1

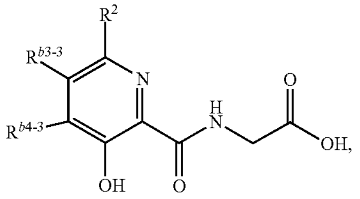

wherein $R^2$ is a hydrogen atom or an optionally substituted methyl group, $R^{b3-3}$ is a 3-chlorophenyl group, a chlorine atom, a bromine atom, an iodine atom, or a trifluoromethanesulfoxy group, $R^{b4-3}$ is a hydrogen atom, or alternatively $R^{b3-3}$ and $R^{b4-3}$ bind to each other and combine together with the pyridine group to which they are adjacent to form a 7-phenyloxy-isoquinoline group, said process comprising:

(i) reacting a compound of formula (b1-2):

b1-2

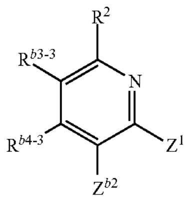

wherein:

$Z^1$ is a chlorine atom, a bromine atom, or an iodine atom, $Z^{b2}$ is a chlorine atom, a bromine atom, or an iodine atom, and $R^2$, $R^{b3-3}$ and $R^{b4-3}$ are the same as defined above, or a compound of formula (2-1):

2-1

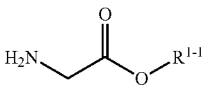

wherein $R^{1-1}$ is an optionally substituted alkyl group or a resin residue, or a salt thereof, and carbon monoxide, in the presence or absence of a palladium catalyst, in the presence or absence of a ligand, in the presence or absence of a base, and in a solvent or in the absence of a solvent to obtain a compound of formula (b3-4):

b3-4

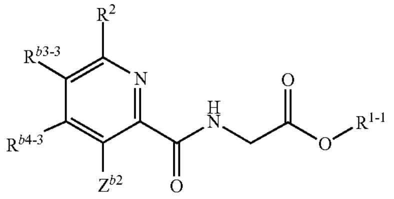

wherein the symbols are the same as defined above, and (ii) reacting the compound of formula (b3-4) and a compound of formula (b4):

b4

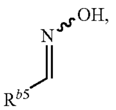

wherein $R^{b5}$ is an optionally substituted aryl group or an optionally substituted alkyl group, in the presence of a palladium catalyst, in the presence or absence of a ligand, in the presence of a base, in a solvent to obtain a compound of formula (b3-5):

b3-5

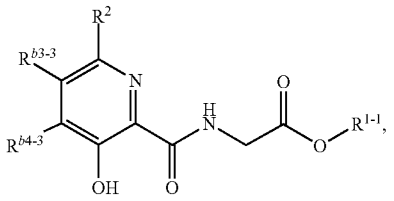

wherein the symbols are the same as defined above; and (iii) converting the compound of formula (b3-5) into a compound of formula (bI-1):

bI-1

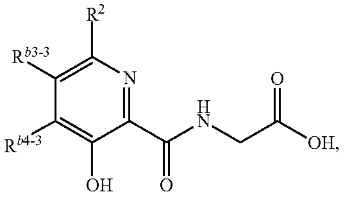

wherein the symbols are the same as defined above.

22. A compound of formula (a1-a):

a1-a

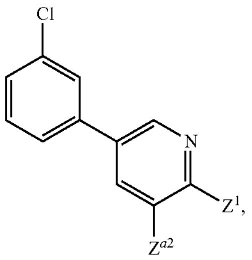

wherein:

$Z^1$ is a chlorine atom, a bromine atom, or an iodine atom, and $Z^{a2}$ is a hydroxy group, or a substituent represented by formula:

wherein $P^1$ is a protecting group for hydroxy group.

23. A crystal of the compound of formula (a3-1-A):

a3-1-A

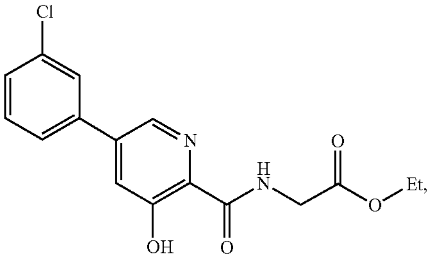

which has an X-ray powder diffraction pattern comprising peaks expressed in 20 angles at 7.96, 11.82, 14.14, 15.94, 24.68, or 39.22±0.2° 2θ.

24. A crystal of the compound of formula (a3-1-A)

a3-1-A

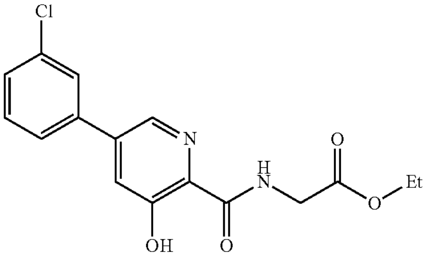

which has an X-ray powder diffraction pattern comprising peaks expressed in 20 angles at 8.52, 10.78, 20.16, 22.64, 23.56, or 34.4±0.2° 2θ.

* * * * *